(12) United States Patent
Graycar et al.

(10) Patent No.: US 10,865,398 B2
(45) Date of Patent: *Dec. 15, 2020

(54) COMPOSITIONS AND METHODS COMPRISING A LIPOLYTIC ENZYME VARIANT

(71) Applicant: DANISCO US INC, Palo Alto, CA (US)

(72) Inventors: Thomas P. Graycar, Pacifica, CA (US); David A. Estell, San Mateo, CA (US); Ayrookaran J. Poulose, Belmont, CA (US); Sina Pricelius, Leiden (NL)

(73) Assignee: DANISCO US INC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/155,034

(22) Filed: Oct. 9, 2018

(65) Prior Publication Data

US 2019/0024064 A1 Jan. 24, 2019

Related U.S. Application Data

(60) Continuation of application No. 16/006,999, filed on Jun. 13, 2018, which is a division of application No. 14/682,924, filed as application No. PCT/US2013/064672 on Oct. 11, 2013, now Pat. No. 10,023,851.

(60) Provisional application No. 61/713,436, filed on Oct. 12, 2012.

(51) Int. Cl.
*C12N 9/20* (2006.01)
*C11D 3/386* (2006.01)

(52) U.S. Cl.
CPC ............ *C12N 9/20* (2013.01); *C11D 3/38627* (2013.01); *C12Y 301/01003* (2013.01)

(58) Field of Classification Search
None
See application file for complete search history.

(56) References Cited

U.S. PATENT DOCUMENTS

| 10,023,851 B2 * | 7/2018 | Graycar .................. C12N 9/20 |
| 2003/0144165 A1 | 7/2003 | Roggen |
| 2005/0059130 A1 | 3/2005 | Bojsen |
| 2006/0229223 A1 | 10/2006 | Minning |

FOREIGN PATENT DOCUMENTS

| WO | WO97/04079 A1 | 2/1997 |
| WO | WO 2000/32758 A1 | 6/2000 |
| WO | WO 2000/60063 A1 | 10/2000 |
| WO | WO2004/099400 A2 | 11/2004 |
| WO | WO2008/008967 A2 | 1/2008 |
| WO | WO 2009/111258 A2 | 9/2009 |

OTHER PUBLICATIONS

International Search Report for PCT/US2013/064672 dated Feb. 26, 2014.
Romdhane et al. Gene cloning and molecular characterization of the Talaromyces thermophilus lipase Catalyzed efficient hydrolysis and synthesis of esters, Gene 494 (2012) 112-118, Epub Dec. 9, 2011.

* cited by examiner

*Primary Examiner* — Iqbal H Chowdhury

(57) ABSTRACT

The present invention provides lipolytic enzyme variants. Specifically, the present invention provides lipolytic enzyme variants having one or more modifications as compared to a parent lipolytic enzyme having at least one improved property. In addition, the present invention provides compositions comprising a lipolytic enzyme variant of the invention. The present invention also provides methods of cleaning using compositions comprising a lipolytic enzyme variant of the invention.

16 Claims, 2 Drawing Sheets

Specification includes a Sequence Listing.

US 10,865,398 B2

COMPOSITIONS AND METHODS COMPRISING A LIPOLYTIC ENZYME VARIANT

CROSS REFERENCE TO RELATED APPLICATIONS

This application is a Continuation of U.S. application Ser. No. 16/006,999, filed Jun. 13, 2018, which is a Divisional of U.S. application Ser. No. 14/682,924, filed Apr. 9, 2015, which is a 371 of International Application No. PCT/US13/64672, filed Oct. 11, 2013, issued as U.S. Pat. No. 10,023,857, which claims the benefit of U.S. Provisional Application No. 61/713,436, filed Oct. 12, 2012, all of which are hereby incorporated by reference in their entirety.

SEQUENCE LISTING

The sequence listing submitted via EFS, in compliance with 37 C.F.R. § 1.52(e), is incorporated herein by reference. The sequence listing text file submitted via EFS contains the file "20181008_NB40152USPCN_SequenceListing.txt" created on Oct. 8, 2018, which is 10,497 bytes in size.

BACKGROUND OF THE INVENTION

Lipolytic enzymes, including lipases and cutinases, have been employed in detergent cleaning compositions for the removal of oily stains. One mechanism by which lipolytic enzymes function is by hydrolyzing triglycerides to generate fatty acids. However, these enzymes are often inhibited by surfactants and other components present in cleaning composition, interfering with their ability to remove oily stains. Accordingly, the need exists for lipolytic enzymes that can function in the harsh environment of cleaning compositions.

SUMMARY OF THE INVENTION

The present invention provides improved lipolytic enzymes, especially enzymes useful for detergent compositions. Specifically, the present invention provides lipolytic enzyme variants having one or more modifications, such as a substitution, as compared to a parent lipolytic enzyme. This can be achieved by making improvements to the enzyme by improving wash performance in standard detergent formulations and low surfactant detergent formulations, stability of the enzyme in detergent compositions, thermostability of the enzyme, substrate hydrolysis, expression and/or modified charge/hydrophobicity profiles that improve effectiveness of the enzyme in a wash cycle. The present invention provides variant lipolytic enzymes, including, but not limited to, variant lipase lipolytic enzymes, that are particularly well suited to and useful in a variety of cleaning applications. The invention also provides methods of cleaning using lipolytic enzyme variants of the present invention.

In one embodiment, the invention is a lipolytic enzyme variant or an active fragment thereof comprising an amino acid modification to a parent lipolytic enzyme, wherein the modification is at a productive position of the lipolytic enzyme variant, wherein at least one modification of the modifications tested at the productive position meet at least one of the following criteria:
  a) a position wherein the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.9, and in addition have a PI for any one of these tests that is greater than or equal to 1.0;
  b) a position wherein the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.8, and in addition have a PI for any one of these tests that is greater than or equal to 1.2;
  c) a position wherein the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.5, and in addition have a PI for any one of these tests that is greater than or equal to 1.5;
and wherein the productive position is selected from the group consisting of 1, 2, 3, 4, 5, 6, 7, 8, 9, 11, 12, 13, 14, 15, 16, 17, 18, 19, 20, 22, 23, 24, 25, 26, 27, 28, 29, 30, 31, 32, 33, 34, 35, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 84, 85, 86, 87, 90, 91, 92, 93, 94, 95, 96, 97, 98, 99, 100, 101, 102, 103, 105, 106, 108, 109, 110, 111, 112, 114, 115, 117, 118, 119, 120, 121, 122, 123, 125, 126, 127, 128, 130, 131, 132, 133, 134, 135, 136, 137, 138, 139, 140, 142, 143, 149, 151, 152, 153, 154, 155, 156, 158, 159, 162, 163, 164, 165, 166, 167, 168, 169, 170, 176, 179, 180, 181, 183, 184, 187, 188, 189, 190, 191, 192, 193, 196, 198, 199, 200, 202, 205, 206, 208, 209, 210, 211, 212, 213, 214, 216, 217, 218, 221, 223, 224, 225, 226, 227, 228, 229, 230, 231, 232, 233, 236, 237, 238, 239, 242, 243, 244, 246, 248, 249, 250, 251, 252, 253, 254, 255, 256, 257, 259, 260, 262, 263, 264, 265, 266, 267, 268, and 269, wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 50% of the modifications tested at the productive position meet at least one of the criteria a, b, and c, listed above, and wherein the productive position is selected from the group consisting of 1, 2, 3, 4, 5, 6, 8, 9, 13, 23, 24, 25, 26, 27, 28, 29, 33, 37, 38, 39, 46, 51, 52, 54, 58, 64, 66, 68, 69, 71, 72, 75, 90, 93, 94, 111, 120, 122, 123, 130, 131, 137, 140, 162, 163, 189, 250, 252, and 264, wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 30% of the modifications tested at the productive position meet at least one of the criteria a, b, and c, listed above, and wherein the productive position is selected from the group consisting of 18, 19, 20, 30, 31, 32, 47, 48, 49, 50, 53, 56, 60, 73, 74, 85, 86, 91, 95, 96, 97, 98, 99, 101, 105, 108, 115, 125, 127, 128, 132, 133, 151, 159, 164, 179, 183, 187, 188, 190, 216, 223, 232, 237, 244, 251, 254, 263, 267, and 269, wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 15% of the modifications tested at the productive position meet at least one of the criteria a, b, and c, listed above, and wherein the productive position is selected from the group consisting of 7, 11, 12, 15, 22, 35, 40, 42, 43, 44, 45, 61, 63, 65, 67, 76, 77, 84, 87, 114, 117, 119, 121, 134, 135, 136, 143, 154, 155, 156, 158, 165, 166, 168, 176, 180, 191, 199, 200, 202, 209, 211, 214, 217, 221, 224, 225, 228, 229, 231, 233, 248, 249, 253, 255, 256, 265, and 268, wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein less than 15% of the modifications tested at the productive position meet at least one of the criteria a, b, and c, listed above, and wherein the productive position is selected from the group consisting of 14, 16, 17, 34, 41, 55, 57, 59, 62, 70, 79, 92, 100, 102, 103, 106, 109, 110, 112, 118, 126, 138, 139, 142, 149, 152, 153, 167, 169, 170, 181, 184, 192, 193, 196, 198, 205, 206, 208, 210, 212, 213, 218, 226, 227, 230, 236, 238, 239, 242, 243, 246, 257, 259, 260, 262, and 266, wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 50% of the modifications tested at the productive position meet at least one of the criteria a, b, and c, listed above, and wherein the productive modification is selected from the group consisting of 1(E,A,C,D,F,I,L,N,PQ,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S,W,Y); 5(D,H,I,K,L,S,T,V,W,Y); 6(L,A,E,H,I,K,M,Q,T,V,Y); 8(N,A,E,G,H,I,K,L,M,T,V,W,Y); 9(Q,A,D,E,G,H,I,K,N,R,W,Y); 13(F,A,H,K,M,N,Q,T,V,Y); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M,N,P,Q,R,S); 29(P,C,E,G,H,I,K,L,M,Q,R,S,T,V,W,Y); 33(N,D,E,F,K,L,M,Q,R,S); 37(T,A,C,D,E,F,G,H,I,K,L,M,P,Q,R,W,Y); 38(G,A,D,E,F,H,I,K,L,M,NT,V,W,Y); 39(N,C,E,H,I,L,P,Q,S,T,V,W,Y); 46(K,D,E,F,G,L,M,V,W); 51(F,A,D,E,G,I,L,M,N,P,R,S,T,Y); 52(L,A,E,G,I,M,R,T,V,W); 54(S,E,F,G,H,K,M,P,R,T,VW,Y); 58(S,D,G,H,I,K,M,Q,R,W); 64(T,C,D,E,G,I,K,L,N,R,V,Y); 66(F,A,G,H,I,L,M,N,Q,R,S,T,VW,Y); 68(A,C,G,I,S,T,V,W,Y); 69(L,A,D,G,H,I,K,N,S,T,W); 71(N,D,E,H,K,Q,R,S,T,V,W,Y); 72(T,A,D,E,F,H,I,K,L,N,P,R,S,V,Y); 75(L,A,D,E,G,H,I,M,N,Q,R,S,T,V,Y); 90(I,A,E,F,N,Q,T,V,Y); 93(L,D,H,I,K,N,P,Q,R,V,W); 94(N,D,G,K,M,P,R,S,T,V); 111(D,A,E,F,L,Q,T,V,W); 120(V,G,H,I,N,S,W,Y); 122(D,A,E,F,H,I,N,S,T,Y); 123(T,E,G,I,K,L,M,N,Q,W); 130(D,A,C,E,F,G,H,Q,R,T,V,W,Y); 131(A,C,H,I,K,N,Q,R,S,T,W,Y); 137(D,A,E,F,G,H,I,K,L,M,N,P,Q,R,S,T,V,W,Y); 140(V,C,E,F,I,L,M,N,Q,T); 162(N,D,E,F,G,H,I,K,M,P,Q,R,S,Y); 163(G,A,F,L,M,N,P,R,S,W,Y); 189(T,D,E,G,K,M,N,Q,R,S,V); 250(P,D,E,G,K,Q,R,S,T); 252(I,A,C,D,E,F,G,H,K,L,N,Q,R,S,T,W); and 264(L,C,E,G,H,M,N,P,Q,R,S,T), wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 30% of the modifications tested at the productive position meet at least one of the criteria a, b, and c, listed above, and wherein the productive modification is selected from the group consisting of 1(E,A,C,D,F,I,L,N,PQ,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S,W,Y); 5(D,H,I,K,L,S,T,V,W,Y); 6(L,A,E,H,I,K,M,Q,T,V,Y); 8(N,A,E,G,H,I,K,L,M,T,V,W,Y); 9(Q,A,D,E,G,H,I,K,N,R,W,Y); 13(F,A,H,K,M,N,Q,T,V,Y); 18(A,C,H,K,M,N,Q,S,W); 19(A,C,G,I,L,T,V,W); 20(A,G,I,P,Q,S,T); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M,N,P,Q,R,S); 29(P,C,E,G,H,I,K,L,M,Q,R,S,T,V,W,Y); 30(A,D,H,L,N,R,V,W); 31(G,D,E,H,M,P,Q,S,V); 32(T,A,I,M,Q,R,S); 33(N,D,E,F,K,L,M,Q,R,S); 37(T,A,C,D,E,F,G,H,I,K,L,M,P,Q,R,W,Y); 38(G,A,D,E,F,H,I,K,L,M,NT,V,W,Y); 39(N,C,E,H,I,L,P,Q,S,T,V,W,Y); 46(K,D,E,F,G,L,M,V,W); 47(A,D,E,F,H,M,T,W); 48(D,E,G,H,L,P,Q); 49(A,G,H,K,L,V,W); 50(T,A,D,F,K,L,R,S,W); 51(F,A,D,E,G,I,L,M,N,P,R,S,T,Y); 52(L,A,E,G,I,M,R,T,V,W); 53(Y,E,G,H,K,L,S,W); 54(S,E,F,G,H,K,M,P,R,T,VW,Y); 56(E,H,K,R,T,V); 58(S,D,G,H,I,K,M,Q,R,W); 60(V,G,K,L,Y); 64(T,C,D,E,G,I,K,L,N,R,V,Y); 66(F,A,G,H,I,L,M,N,Q,R,S,T,VW,Y); 68(A,C,G,I,S,T,V,W,Y); 69(L,A,D,G,H,I,K,N,S,T,W); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T,V,Y); 85(S,F,H,I,N,Q,T); 86(I,L,M,P,Q,T,V,Y); 90(I,A,E,F,N,Q,T,V,Y); 91(G,E,F,H,I,M,Q,R); 93(L,D,H,I,K,N,P,Q,R,V,W); 94(N,D,G,K,M,P,R,S,T,V); 95(F,G,H,K,L,Q,T,V,W); 96(D,A,K,P,R,V); 97(L,A,D,I,M,Q,T); 98(K,D,E,H,I,M,Q); 99(E,D,K,P,Q,S,T,W); 101(N,C,D,E,H,M,Y); 105(S,A,D,E,F,K,P,W); 108(R,E,F,K,M,Q,Y); 111(D,A,E,F,L,Q,T,V,W); 115(S,G,I,L,M,N,R,T,V); 120(V,G,H,I,N,S,W,Y); 122(D,A,E,F,H,I,N,S,T,Y); 123(T,E,G,I,K,L,M,N,Q,W); 125(R,C,G,I,N,Q,T,Y); 127(K,D,E,F,G,R,T); 128(V,C,H,I,L,N,S,W,Y); 130(D,A,C,E,F,G,H,Q,R,T,V,W,Y); 131(A,C,H,I,K,N,Q,R,S,T,W,Y); 132(V,C,D,H,I,K,Q,R,W); 133(R,E,F,I,N,Q,V); 137(D,A,E,F,G,H,I,K,L,M,N,P,Q,R,S,T,V,W,Y); 140(V,C,E,F,I,L,M,N,Q,T); 151(L,I,M,N,P,T,V,W); 159(L,E,M,Q,R,W); 162(N,D,E,F,G,H,I,K,M,P,Q,R,S,Y); 163(G,A,F,L,M,N,P,R,S,W,Y); 164(Y,D,N,R,S,V); 179(R,E,H,I,K,L,Q,V); 183(E,H,M,Q,S,T,V,Y); 187(V,G,H,L,N,Q,S,T,W); 188(Q,C,E,F,H,R,T); 189(T,D,E,G,K,M,N,Q,R,S,V); 190(G,D,H,R,S,Y); 216(S,D,G,N,Q,V,W); 223(K,A,H,L,M,Q,S,T,V); 232(R,C,D,I,L,M,P,T,W); 237(K,E,H,I,L,T,W,Y); 244(T,A,F,I,L,M,P,Q,S); 250(P,D,E,G,K,Q,R,S,T); 251(N,D,M,Q,S,T,W,Y); 252(I,A,C,D,E,F,G,H,K,L,N,Q,R,S,T,W); 254(D,A,H,K,N,P,T); 256(P,A,D,S,T); 263(G,C,H,I,K,M,V); 264(L,C,E,G,H,M,N,P,Q,R,S,T); 267(T,G,I,L,M,P,W); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least 15% of the modifications tested at the productive position meet at least one of the criteria a, b, and c, listed above, and wherein the productive modification is selected from the group consisting of 1(E, A,C,D,F,I,L,N,PQ,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S, W,Y); 5(D,H,I,K,L,S,T,V,W,Y); 6(L,A,E,H,I,K,M,Q,T,V, Y); 7(F,H,M,V,Y); 8(N,A,E,G,H,I,K,L,M,T,V,W,Y); 9(Q,A, D,E,G,H,I,K,N,R,W,Y); 11(N,H,K,V,Y); 12(L,F,H,V,W); 13(F,A,H,K,M,N,Q,T,V,Y); 15(Q,G,H,M,S); 18(A,C,H,K, M,N,Q,S,W); 19(A,C,G,I,L,T,V,W); 20(A,G,I,P,Q,S,T); 22(C,H,L,M); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G, H,I,K,L,S,T,V,W); 26(N,C,G,K,L,M,Q,S,T,V,W,Y); 27(D, A,E,F,G,H,I,N,Q,R,S,T,V,Y); 28(A,D,E,F,G,H,I,L,M,N,P,Q, R,S); 29(P,C,E,G,H,I,K,L,M,Q,R,S,T,V,W,Y); 30(A,D,H,L, N,R,V,W); 31(G,D,E,H,M,P,Q,S,V); 32(T,A,I,M,Q,R,S); 33(N,D,E,F,K,L,M,Q,R,S); 35(T,E,K,R); 37(T,A,C,D,E,F, G,H,I,K,L,M,P,Q,R,W,Y); 38(G,A,D,E,F,H,I,K,L,M,NT,V, W,Y); 39(N,C,E,H,I,L,P,Q,S,T,V,W,Y); 40(A,F,M,S,W); 42(P,C,G,I,V,W); 43(E,D,I,M,R,T); 44(V,H,I,T); 45(E,F,Q, V); 46(K,D,E,F,G,L,M,V,W); 47(A,D,E,F,H,M,T,W); 48(D, E,G,H,L,P,Q); 49(A,G,H,K,L,V,W); 50(T,A,D,F,K,L,R,S, W); 51(F,A,D,E,G,I,L,M,N,P,R,S,T,Y); 52(L,A,E,G,I,M,R, T,V,W); 53(Y,E,G,H,K,L,S,W); 54(S,E,F,G,H,K,M,P,R,T, VW,Y); 56(E,H,K,R,T,V); 58(S,D,G,H,I,K,M,Q,R,W); 60(V,G,K,L,Y); 61(G,A,D,L,R); 63(V,K,Q,T); 64(T,C,D,E, G,I,K,L,N,R,V,Y); 65(G,L,V,Y); 66(F,A,G,H,I,L,M,N,Q,R, S,T,VW,Y); 67(L,H,I,Q,V); 68(A,C,G,I,S,T,V,W,Y); 69(L, A,D,G,H,I,K,N,S,T,W); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T, V,Y); 76(I,H,S,V); 77(V,A,I,L,N,T); 84(R,H,Q,W); 85(S,F, H,I,N,Q,T); 86(I,L,M,P,Q,T,V,Y); 87(E,A,D,G,P,V); 90(I,A, E,F,N,Q,T,V,Y); 91(G,E,F,H,I,M,Q,R); 93(L,D,H,I,K,N,P, Q,R,V,W); 94(N,D,G,K,M,P,R,S,T,V); 95(F,G,H,K,L,Q,T, V,W); 96(D,A,K,P,R,V); 97(L,A,D,I,M,Q,T); 98(K,D,E,H, I,M,Q); 99(E,D,K,P,Q,S,T,W); 101(N,C,D,E,H,M,Y); 105 (S,A,D,E,F,K,P,W); 108(R,E,F,K,M,Q,Y); 111(D,A,E,F,L, Q,T,V,W); 114(T,F,I,M,V); 115(S,G,I,L,M,N,R,T,V); 117 (W,H,K,Q,V); 119(S,D,I,Q,T,V); 120(V,G,H,I,N,S,W,Y); 121(A,K,Q); 122(D,A,E,F,H,I,N,S,T,Y); 123(T,E,G,I,K,L, M,N,Q,W); 125(R,C,G,I,N,Q,T,Y); 127(K,D,E,F,G,R,T); 128(V,C,H,I,L,N,S,W,Y); 130(D,A,C,E,F,G,H,Q,R,T,V,W, Y); 131(A,C,H,I,K,N,Q,R,S,T,W,Y); 132(V,C,D,H,I,K,Q,R, W); 133(R,E,F,I,N,Q,V); 134(E,L,P,V); 135(H,F,K,T); 136 (P,D,Q,R); 137(D,A,E,F,G,H,I,K,L,M,N,P,Q,R,S,T,V,W,Y); 140(V,C,E,F,I,L,M,N,Q,T); 143(T,A,G,N,S); 151(L,I,M,N, P,T,V,W); 154(V,F,I,L,M,Y); 155(A,G,S,T); 156(G,F,M,T, W); 158(D,E,F,Y); 159(L,E,M,Q,R,W); 162(N,D,E,F,G,H, I,K,M,P,Q,R,S,Y); 163(G,A,F,L,M,N,P,R,S,W,Y); 164(Y,D, N,R,S,V); 165(D,I,P,Y); 166(I,D,G,W); 168(V,G,L,Q); 176 (V,F,I,L,N,W); 179(R,E,H,I,K,L,Q,V); 180(A,D,K,Q,T); 183(E,H,M,Q,S,T,V,Y); 187(V,G,H,L,N,Q,S,T,W); 188(Q, C,E,F,H,R,T); 189(T,D,E,G,K,M,N,Q,R,S,V); 190(G,D,H, R,S,Y); 191(G,F,L,V); 199(T,G,N,V); 200(N,A,P,S); 202(I, L,M,P,V); 209(R,H,S,T); 211(F,I,R,T,W); 214(S,A,D,M); 216(S,D,G,N,Q,V,W); 217(S,H,K,V); 221(W,F,G,Y); 223 (K,A,H,L,M,Q,S,T,V); 224(S,A,F,P); 225(G,C,E,K,R); 227 (L,C,H,M); 228(V,A,E,R); 229(P,I,K,M,S); 231(T,G,H,K,L, M); 232(R,C,D,I,L,M,P,T,W); 233(N,D,G,H,Q); 237(K,E, H,I,L,T,W,Y); 244(T,A,F,I,L,M,P,Q,S); 248(N,D,L,Y); 249 (Q,E,G,T); 250(P,D,E,G,K,Q,R,S,T); 251(N,D,M,Q,S,T,W, Y); 252(I,A,C,D,E,F,G,H,K,L,N,Q,R,S,T,W); 253(P,F,H,N, R); 254(D,A,H,K,N,P,T); 255(I,F,L,W); 256(P,A,D,S,T); 263(G,C,H,I,K,M,V); 264(L,C,E,G,H,M,N,P,Q,R,S,T); 265 (I,L,M,Q,R,W); 267(T,G,I,L,M,P,W); 268(C,D,H,N); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

In one embodiment, the invention is a lipolytic enzyme variant or an active fragment thereof comprising an amino acid modification to a parent lipolytic enzyme, wherein the modification is at a productive position of the lipolytic enzyme variant, wherein at least one of the modifications tested at the productive position meet at least one of the criteria a, b, and c, listed above, and wherein the productive modification is selected from the group consisting of 1(E, A,C,D,F,I,L,N,PQ,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S, W,Y); 5(D,H,I,K,L,S,T,V,W,Y); 6(L,A,E,H,I,K,M,Q,T,V, Y); 7(F,H,M,V,Y); 8(N,A,E,G,H,I,K,L,M,T,V,W,Y); 9(Q,A, D,E,G,H,I,K,N,R,W,Y); 11(N,H,K,V,Y); 12(L,F,H,V,W); 13(F,A,H,K,M,N,Q,T,V,Y); 14(A,S,V); 15(Q,G,H,M,S); 16(Y,H,W); 17(S,E); 18(A,C,H,K,M,N,Q,S,W); 19(A,C,G, I,L,T,V,W); 20(A,G,I,P,Q,S,T); 22(C,H,L,M); 23(G,C,D,E, F,H,I,K,L,M,N,P,Q,R,S,T,V,W); 24(K,A,D,E,F,H,I,L,M,N, P,R,T,V,W,Y); 25(N,A,C,D,E,G,H,I,K,L,S,T,V,W); 26(N,C, G,K,L,M,Q,S,T,V,W,Y); 27(D,A,E,F,G,H,I,N,Q,R,S,T,V, Y); 28(A,D,E,F,G,H,I,L,M,N,P,Q,R,S); 29(P,C,E,G,H,I,K, L,M,Q,R,S,T,V,W,Y); 30(A,D,H,L,N,R,V,W); 31(G,D,E,H, M,P,Q,S,V); 32(T,A,I,M,Q,R,S); 33(N,D,E,F,K,L,M,Q,R, S); 34(I,P); 35(T,E,K,R); 37(T,A,C,D,E,F,G,H,I,K,L,M,P,Q, R,W,Y); 38(G,A,D,E,F,H,I,K,L,M,NT,V,W,Y); 39(N,C,E,H, I,L,P,Q,S,T,V,W,Y); 40(A,F,M,S,W); 41(C,V); 42(P,C,G,I, V,W); 43(E,D,I,M,R,T); 44(V,H,I,T); 45(E,F,Q,V); 46(K,D, E,F,G,L,M,V,W); 47(A,D,E,F,H,M,T,W); 48(D,E,G,H,L,P, Q); 49(A,G,H,K,L,V,W); 50(T,A,D,F,K,L,R,S,W); 51(F,A, D,E,G,I,L,M,N,P,R,S,T,Y); 52(L,A,E,G,I,M,R,T,V,W); 53(Y,E,G,H,K,L,S,W); 54(S,E,F,G,H,K,M,P,R,T,VW,Y); 55(F,G,W); 56(E,H,K,R,T,V); 57(D,S); 58(S,D,G,H,I,K,M, Q,R,W); 59(G,D); 60(V,G,K,L,Y); 61(G,A,D,L,R); 62(D, N); 63(V,K,Q,T); 64(T,C,D,E,G,I,K,L,N,R,V,Y); 65(G,L,V, Y); 66(F,A,G,H,I,L,M,N,Q,R,S,T,VW,Y); 67(L,H,I,Q,V); 68(A,C,G,I,S,T,V,W,Y); 69(L,A,D,G,H,I,K,N,S,T,W); 70(D,S); 71(N,D,E,H,K,Q,R,S,T,V,W,Y); 72(T,A,D,E,F,H,I, K,L,N,P,R,S,V,Y); 73(N,E,G,H,K,R,S); 74(K,A,D,E,G,H,N, Q,S); 75(L,A,D,E,G,H,I,M,N,Q,R,S,T,V,Y); 76(I,H,S,V); 77(V,A,I,L,N,T); 79(S,A,M); 84(R,H,Q,W); 85(S,F,H,I,N, Q,T); 86(I,L,M,P,Q,T,V,Y); 87(E,A,D,G,P,V); 90(I,A,E,F,N, Q,T,V,Y); 91(G,E,F,H,I,M,Q,R); 92(N,A,T); 93(L,D,H,I,K, N,P,Q,R,V,W); 94(N,D,G,K,M,P,R,S,T,V); 95(F,G,H,K,L, Q,T,V,W); 96(D,A,K,P,R,V); 97(L,A,D,I,M,Q,T); 98(K,D, E,H,I,M,Q); 99(E,D,K,P,Q,S,T,W); 100(I,M); 101(N,C,D,E, H,M,Y); 102(D,H); 103(I,Y); 105(S,A,D,E,F,K,P,W); 106 (G,H); 108(R,E,F,K,M,Q,Y); 109(G,T); 110(H,N,S); 111(D, A,E,F,L,Q,T,V,W); 112(G,F,Q); 114(T,F,I,M,V); 115(S,G,I, L,M,N,R,T,V); 117(W,H,K,Q,V); 118(R,P); 119(S,D,I,Q,T, V); 120(V,G,H,I,N,S,W,Y); 121(A,K,Q); 122(D,A,E,F,H,I, N,S,T,Y); 123(T,E,G,I,K,L,M,N,Q,W); 125(R,C,G,I,N,Q,T, Y); 126(Q,I,M); 127(K,D,E,F,G,R,T); 128(V,C,H,I,L,N,S, W,Y); 130(D,A,C,E,F,G,H,Q,R,T,V,W,Y); 131(A,C,H,I,K, N,Q,R,S,T,W,Y); 132(V,C,D,H,I,K,Q,R,W); 133(R,E,F,I,N, Q,V); 134(E,L,P,V); 135(H,F,K,T); 136(P,D,Q,R); 137(D,A, E,F,G,H,I,K,L,M,N,P,Q,R,S,T,V,W,Y); 138(Y,F); 139(RLT); 140(V,C,E,F,I,L,M,N,Q,T); 142(F,H,Y); 143(T,A,G,N,S); 149(G,A); 151(L,I,M,N,P,T,V,W); 152(A,I,V); 153(T,S); 154(V,F,I,L,M,Y); 155(A,G,S,T); 156(G,F,M,T,W); 158(D, E,F,Y); 159(L,E,M,Q,R,W); 162(N,D,E,F,G,H,I,K,M,P,Q, R,S,Y); 163(G,A,F,L,M,N,P,R,S,W,Y); 164(Y,D,N,R,S,V); 165(D,I,P,Y); 166(I,D,G,W); 167(D,N); 168(V,G,L,Q); 169

(F,S,Y); 170(S,G); 176(V,F,I,L,N,W); 179(R,E,H,I,K,L,Q,V); 180(A,D,K,Q,T); 181(F,L); 183(E,H,M,Q,S,T,V,Y); 184(F,W,Y); 187(V,G,H,L,N,Q,S,T,W); 188(Q,C,E,F,H,R,T); 189(T,D,E,G,K,M,N,Q,R,S,V); 190(G,D,H,R,S,Y); 191(G,F,L,V); 192(T,N,P); 193(L,T); 196(I,V); 198(H,G,S); 199(T,G,N,V); 200(N,A,P,S); 202(I,L,M,P,V); 205(R,D); 206(L,N); 208(P,E,N); 209(R,H,S,T); 210(E,S); 211(F,I,R,T,W); 212(G,Q); 213(Y,S); 214(S,A,D,M); 216(S,D,G,N,Q,V,W); 217(S,H,K,V); 218(P,T); 221(W,F,G,Y); 223(K,A,H,L,M,Q,S,T,V); 224(S,A,F,P); 225(G,C,E,K,R); 226(T,D,N); 227(L,C,H,M); 228(V,A,E,R); 229(P,I,K,M,S); 230(V,W); 231(T,G,H,K,L,M); 232(R,C,D,I,L,M,P,T,W); 233(N,D,G,H,Q); 236(V,W); 237(K,E,H,I,L,T,W,Y); 238(I,V); 239(E,K); 242(D,T); 243(A,S); 244(T,A,F,I,L,M,P,Q,S); 246(G,I); 248(N,D,L,Y); 249(Q,E,G,T); 250(P,D,E,G,K,Q,R,S,T); 251(N,D,M,Q,S,T,W,Y); 252(I,A,C,D,E,F,G,H,K,L,N,Q,R,S,T,W); 253(P,F,H,N,R); 254(D,A,H,K,N,P,T); 255(I,F,L,W); 256(P,A,D,S,T); 257(A,W,Y); 259(L,W,Y); 260(W,P); 262(F,D,K); 263(G,C,H,I,K,M,V); 264(L,C,E,G,H,M,N,P,Q,R,S,T); 265(I,L,M,Q,R,W); 266(G,E); 267(T,G,I,L,M,P,W); 268(C,D,H,N); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

In one embodiment, the invention is a cleaning composition comprising at least one lipolytic enzyme variant as listed above. In some embodiments, the invention further includes an additional enzyme from the group consisting of hemicellulases, cellulases, peroxidases, lipolytic enzymes, metallolipolytic enzymes, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases.

In one embodiment, the invention is a method of cleaning, comprising contacting a surface or an item with a cleaning composition comprising at least one lipolytic enzyme variant listed above.

DESCRIPTION OF THE INVENTION

Figure 1:
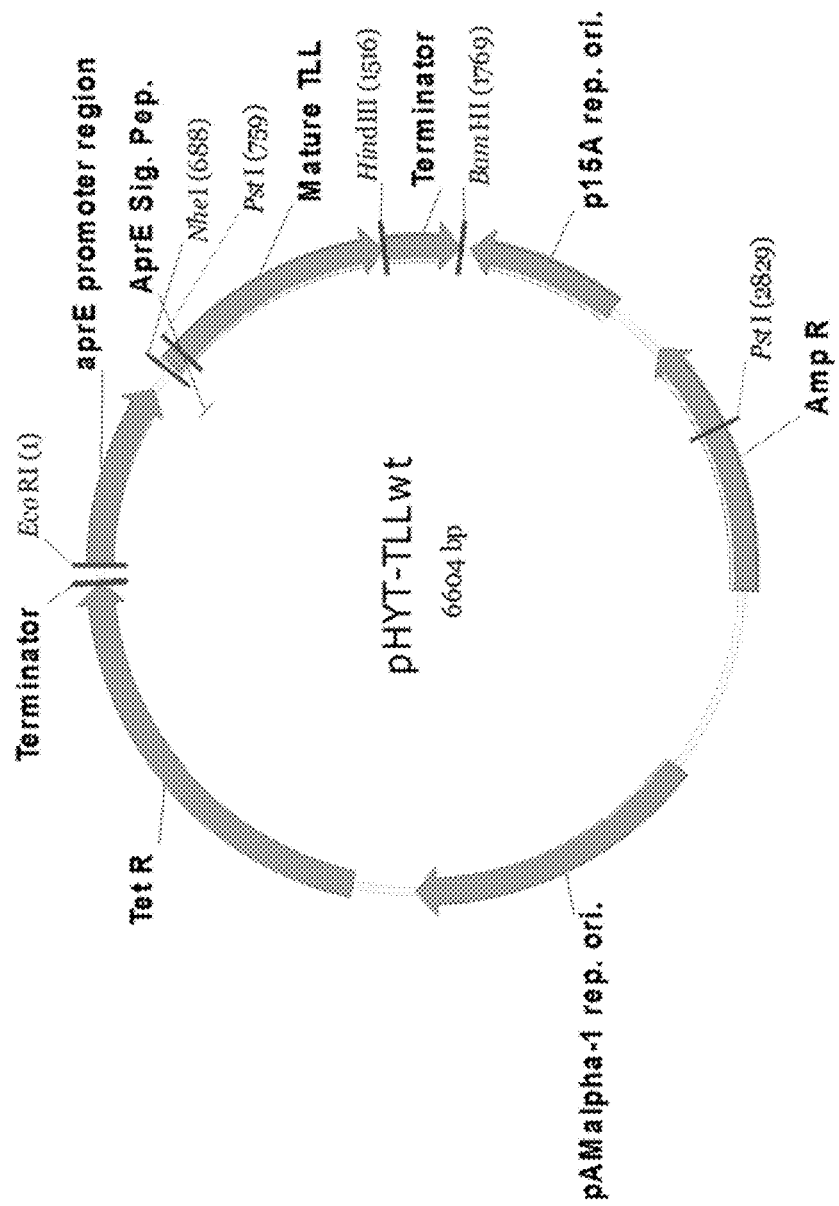
FIG. 1 is a plasmid map of pHYT-TLLwt.

The present invention provides improved lipolytic enzymes, especially enzymes useful for detergent compositions. Specifically, the present invention provides lipolytic enzyme variants having one or more modifications, such as a substitution, as compared to a parent lipolytic enzyme. This can be achieved by making improvements to the enzyme by improving wash performance, stability of the enzyme in detergent compositions, thermostability of the enzyme, and/or modified substrate hydrolysis, and/or charge/hydrophobicity profiles that improve effectiveness of the enzyme in a wash cycle. The present invention provides variant lipolytic enzymes, including, but not limited to, variant lipase lipolytic enzymes, that are particularly well suited to and useful in a variety of cleaning applications. The invention includes compositions comprising at least one of the variant lipolytic enzymes (e.g., variant lipases) set forth herein. Some such compositions comprise detergent compositions. The invention provides *Thermomyces* species variant lipolytic enzymes and compositions comprising one or more such variant lipases. The lipolytic enzyme variants of the present invention can be combined with other enzymes useful in detergent compositions. The invention also provides enzyme compositions having comparable or improved wash performance, as compared to known lipolytic enzymes, such as, known lipase lipolytic enzymes. The invention also provides methods of cleaning using lipolytic enzyme variants of the present invention.

The invention includes enzyme variants of lipolytic enzymes having one or more modifications from a parent lipolytic enzyme. The enzyme variants can be useful in a detergent composition by having a minimum performing index for wash performance, substrate hydrolysis, stability of the enzyme in detergent compositions and thermostability of the enzyme, while having at least one of these characteristics improved from a parent lipolytic enzyme.

Additionally, the invention provides modifications, such as a substitution, at one or more amino acid positions in a lipolytic enzyme which can be useful in a detergent composition where favorable modifications result in a minimum performing index for wash performance, substrate hydrolysis, stability of the enzyme in detergent compositions and thermostability of the enzyme, while having at least one of these characteristics improved from a parent lipolytic enzyme. These modifications are considered suitable modifications of the invention. These amino acid positions can be considered useful positions for combinatorial modifications to a parent lipolytic enzyme. Lipolytic enzyme amino acid positions found to be useful positions can be further characterized by having multiple modifications that are suitable for use in a detergent composition. For each position, greater numbers of possible suitable modifications denotes a higher productivity of a particular position.

Unless defined otherwise herein, all technical and scientific terms used herein have the same meaning as commonly understood by one of ordinary skill in the art to which this invention pertains. Although many methods and materials similar or equivalent to those described herein find use in the practice of the present invention, some methods and materials are described herein. Accordingly, the terms defined immediately below are more fully described by reference to the specification as a whole. All patents, patent applications, articles and publications mentioned herein, both supra and infra, are hereby expressly incorporated herein by reference.

Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context in which they are used by those of skill in the art.

It is intended that every maximum numerical limitation given throughout this specification include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

A "protein" or "polypeptide" comprises a polymeric sequence of amino acid residues. The terms "protein" and "polypeptide" are used interchangeably herein. The single and 3-letter code for amino acids as defined in conformity with the IUPAC-IUB Joint Commission on Biochemical Nomenclature (JCBN) is used through out this disclosure. It is also understood that a polypeptide can be coded for by more than one nucleotide sequence due to the degeneracy of the genetic code. Mutations can be named by the one letter code for the parent amino acid, followed by a number and then the one letter code for the variant amino acid. For example, mutating glycine (G) at position 87 to serine (S) can be represented as "G087S" or "G87S". Multiple mutations can be indicated by inserting a "−" between the mutations. For example, mutations at positions 87 and 90 can be represented as either "G087S−A090Y" or "G87S−A90Y" or "G87S+A90Y" or "G087S+A090Y".

The terms "derived from" and "obtained from" refer not only to a lipolytic enzyme produced or producible by a strain of the organism in question, but also a lipolytic enzyme encoded by a DNA sequence isolated from such strain and produced in a host organism containing such DNA sequence. Additionally, the term refers to a lipolytic enzyme which is encoded by a DNA sequence of synthetic and/or cDNA origin and which has the identifying characteristics of the lipolytic enzyme in question. To exemplify, "lipolytic enzymes derived from *Thermomyces*" refers to those enzymes having lipolytic activity which are naturally produced by *Thermomyces*, as well as to lipolytic enzymes like those produced by *Thermomyces* sources but which through the use of genetic engineering techniques are produced by non-*Thermomyces* organisms transformed with a nucleic acid encoding the lipolytic enzymes.

As used herein, "homology" refers to sequence similarity or identity, with identity being preferred. Homology may be determined using standard techniques known in the art (See e.g., Smith and Waterman, Adv. Appl. Math. 2:482 (1981); Needleman and Wunsch, J. Mol. Biol. 48:443 (1970); Pearson and Lipman, Proc. Natl. Acad. Sci. USA 85:2444 (1988); software programs such as GAP, BESTFIT, FASTA, and TFASTA in the Wisconsin Genetics Software Package (Genetics Computer Group, Madison, Wis.); and Devereux et al., Nucl. Acid Res. 12:387-395 (1984)). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (See, Feng and Doolittle, J. Mol. Evol. 35:351-360 (1987)). The method is similar to that described by Higgins and Sharp (See, Higgins and Sharp, CABIOS 5:151-153 (1989)). Useful PILEUP parameters including a default gap weight of 3.00, a default gap length weight of 0.10, and weighted end gaps. Another example of a useful algorithm is the BLAST algorithm, described by Altschul et al., (See, Altschul et al., J. Mol. Biol. 215:403-410 (1990); and Karlin and Altschul, Proc. Natl. Acad. Sci. USA 90:5873-5787 (1993)). A particularly useful BLAST program is the WU-BLAST-2 program (See, Altschul et al., Meth. Enzymol. 266:460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (See, Altschul, et al., J. Mol. Biol., 215:403-410 (1990)). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 (1992)) alignments (B) of 50, expectation (E) of 10, M'5, N'-4, and a comparison of both strands.

The BLAST algorithm then performs a statistical analysis of the similarity between two sequences (See e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a lipolytic enzyme nucleic acid of this invention if the smallest sum probability in a comparison of the test nucleic acid to a lipolytic enzyme nucleic acid is less than about 0.1, more preferably less than about 0.01, and most preferably less than about 0.001. Where the test nucleic acid encodes a lipolytic enzyme polypeptide, it is considered similar to a specified lipolytic enzyme nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference (i.e., query) amino acid sequence means that the subject amino acid sequence is identical (i.e., on an amino acid-by-amino acid basis) by a specified percentage to the query amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity or "% nucleotide sequence identity" of a subject nucleic acid sequence to a reference (i.e. query) nucleic acid sequence means that the subject nucleic acid sequence is identical (i.e., on a nucleotide-by-nucleotide basis for a polynucleotide sequence) by a specified percentage to the query sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

"Optimal alignment" or "optimally aligned" refers to the alignment of two (or more) sequences giving the highest percent identity score. For example, optimal alignment of two protein sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

In some embodiments, two polypeptide sequences are deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (See, Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to for example, the BLASTP program for amino acid sequences and the BLASTN program for nucleic acid sequences (See e.g., Altschul et al., Nucleic Acids Res. 25(17):3389-3402 (1997); See also, the National Center for Biotechnology Information (NCBI) website).

A polypeptide of interest may be said to be "substantially identical" to a parent polypeptide if the polypeptide of interest comprises an amino acid sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the parent polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative amino acid substitution or one or more conservative amino acid substitutions.

A nucleic acid of interest may be said to be "substantially identical" to a parent nucleic acid if the nucleic acid of interest comprises a nucleotide sequence having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the parent nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

A nucleic acid or polynucleotide is "isolated" when it is partially or completely separated from other components, including but not limited to for example, other proteins, nucleic acids, cells, etc. Similarly, a polypeptide, protein or peptide is "isolated" when it is partially or completely separated from other components, including but not limited to for example, other proteins, nucleic acids, cells, etc. On a molar basis, an isolated species is more abundant than are other species in a composition. For example, an isolated species may comprise at least about 50%, about 70%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a protein or nucleic acid sample, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide of the invention (e.g., substantially pure variant lipolytic enzyme or polynucleotide encoding a variant lipolytic enzyme of the invention, respectively) will typically comprise at least about 55%, about 60%, about 70%, about 80%, about 85%, about 90%, about 91%, about 92%, about 93%, about 94%, about 95%, about 96%, about 97%, about 98, about 99%, about 99.5% or more by weight (on a molar basis) of all macromolecular species in a particular composition.

The position of an amino acid residue in a given amino acid sequence is typically numbered herein using the numbering of the position of the corresponding amino acid residue of the *Thermomyces lanuginosus* lipase TLL amino acid sequence shown in SEQ ID NO:4. The *T lanuginosus* lipase TLL amino acid sequence of SEQ ID NO:4, thus serves as a reference parent sequence. A given amino acid sequence, such as a variant lipolytic enzyme amino acid sequence described herein, can be aligned with the TLL sequence (SEQ ID NO:4) using an alignment algorithm as described herein, and an amino acid residue in the given amino acid sequence that aligns (preferably optimally aligns) with an amino acid residue in the TLL sequence can be conveniently numbered by reference to the corresponding amino acid residue in the lipase TLL sequence.

Lipolytic Enzymes of the Invention

As used herein, a lipolytic enzyme includes an enzyme, polypeptide, or protein exhibiting a lipid degrading capability such as a capability of degrading a triglyceride or a phospholipid. The lipolytic enzyme can be, for example, a lipase, a phospholipase, an esterase or a cutinase. Lipolytic enzymes can be lipolytic enzymes having an α/β hydrolase fold. These enzymes typically have a catalytic triad of serine, aspartic acid and histidine residues. The α/β hydrolases include lipases and cutinases. Cutinases show little, if any, interfacial activation, where lipases often undergo a conformational change in the presence of a lipid-water interface (Longhi and Cambillau (1999) Biochimica et Biophysica Acta 1441:185-96). An active fragment of a lipolytic enzyme is a portion of a lipolytic enzyme that retains a lipid degrading capability. An active fragment retains the catalytic triad. As used herein, lipolytic activity can be determined according to any procedure known in the art (see, e.g., Gupta et al., *Biotechnol. Appl. Biochem.*, 37:63-71, 2003; U.S. Pat. No. 5,990,069; and International Patent Publication No. WO 96/1 8729A1).

In some embodiments, lipolytic enzymes of the present invention are α/β hydrolases. In some embodiments, lipolytic enzymes of the present invention are lipases. In some embodiments, lipolytic enzymes of the present invention are cutinases.

Productive Positions of Lipolytic Enzymes

The invention provides amino acid positions in a lipolytic enzyme which can be useful in a detergent composition where favorable modifications result in a minimum performing index for wash performance, substrate hydrolysis, stability of the enzyme in detergent compositions and thermostability of the enzyme, while having at least one of these characteristics improved from a parent lipolytic enzyme. These modifications are considered suitable modifications of the invention.

The stability of lipolytic enzymes of the present invention can be compared to the stability of a standard, for example, the *Thermomyces lanuginosus* lipase TLL of SEQ ID NO:3.

The terms "thermal stability" and "thermostability" refer to lipases of the present disclosure that retain a specified amount of enzymatic activity after exposure to an identified temperature, often over a given period of time under conditions prevailing during the lipolytic, hydrolyzing, cleaning or other process disclosed herein, for example while exposed to altered temperatures. Altered temperatures include increased or decreased temperatures. In some embodiments, the lipases retain at least about 50%, about 60%, about 70%, about 75%, about 80%, about 85%, about 90%, about 92%, about 95%, about 96%, about 97%, about 98%, or about 99% lipolytic activity after exposure to altered temperatures over a given time period, for example, at least about 60 minutes, about 120 minutes, about 180 minutes, about 240 minutes, about 300 minutes, etc.

As used herein, improved properties of a variant lipolytic enzyme includes a variant lipolytic enzyme with improved or enhanced wash or cleaning performance, and/or improved or enhanced stability optionally with retained wash or cleaning performance, relative to the corresponding parent lipolytic enzyme (e.g., wild-type or naturally-occurring lipolytic enzyme). The improved properties of a variant lipolytic enzyme may comprise improved wash or cleaning performance and/or improved stability and/or improved substrate hydrolysis and/or improved expression. In some embodiments, the invention provides variant lipolytic enzymes of the invention that exhibit one of more of the following properties: improved hand wash performance, improved hand or manual dishwashing performance, improved automatic dishwashing performance, improved laundry performance, and/or improved stability relative to a reference parent lipolytic enzyme (e.g., wild-type lipolytic enzyme, such as a wild-type lipase.

Lipolytic enzyme amino acid positions found to be useful positions can have different modifications that are suitable for use in a detergent composition. Modifications can include an insertion, deletion or substitution at the particular position. In one embodiment, a modification is a substitution. For each position, greater numbers of possible suitable modifications results in a higher productivity score for the position. For example, amino acid positions can have at least 50%, 30% or 15% of the modifications tested at a productive position as suitable modifications, wherein the modification meets at least one of the following suitability criteria:

a) a position wherein the minimum performance indices (PI) relative to TLL parent for expression, CS-61 microswatch activity at pH 8.2, activity on p-Nitrophenyl ester substrates at pH 6 or pH 8.2, and detergent stability, LAS stability or thermostability are greater than or equal to 0.9, and in addition have a PI for any one of these tests that is greater than or equal to 1.0;

b) a position wherein the minimum performance indices (PI) relative to TLL parent for expression, CS-61 microswatch activity at pH 8.2, activity on p-Nitrophenyl ester substrates at pH 6 or pH 8.2, and detergent stability, LAS stability or thermostability are greater than or equal to 0.8, and in addition have a PI for any one of these tests that is greater than or equal to 1.2; or c) a position wherein the minimum performance indices (PI) relative to TLL parent for expression, CS-61 microswatch activity at pH 8.2, activity on p-Nitrophenyl ester substrates at pH 6 or pH 8.2, and detergent stability, LAS stability or thermostability are greater than or equal to 0.5, and in addition have a PI for any one of these tests that is greater than or equal to 1.5.

Lipolytic enzymes positions of the present invention that have at least 50% of the modifications tested as suitable modifications include positions 1, 2, 3, 4, 5, 6, 8, 9, 13, 23, 24, 25, 26, 27, 28, 29, 33, 37, 38, 39, 46, 51, 52, 54, 58, 64, 66, 68, 69, 71, 72, 75, 90, 93, 94, 111, 120, 122, 123, 130, 131, 137, 140, 162, 163, 189, 250, 252, and 264, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least 50% of the modifications tested as suitable modifications include the modifications 1(E,A,C,D,F,I,L,N, P,Q,R,S,T,V,W,Y); 2(V,F,G,H,I,K,L,M,P,T); 3(S,A,D,E,G,H, K,Q,R,T,Y); 4(Q,A,D,F,G,I,K,L,M,N,P,R,S,W,Y); 5(D,H,I, K,L,S,T,V,W,Y); 6(L,A,E,H,I,K,M,Q,T,V,Y); 8(N,A,E,G,H, I,K,L,M,T,V,W,Y); 9(Q,A,D,E,G,H,I,K,N,R,W,Y); 13(F,A, H,K,M,N,Q,T,V,Y); 23(G,C,D,E,F,H,I,K,L,M,N,P,Q,R,S,T, V,W); 24(K,A,D,E,F,H,I,L,M,N,P,R,T,V,W,Y); 25(N,A,C,D, E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M, N,P,Q,R,S); 29(P,C,E,G,H,I,K,L,M,Q,R,S,T,V,W,Y); 33(N, D,E,F,K,L,M,Q,R,S); 37(T,A,C,D,E,F,G,H,I,K,L,M,P,Q,R, W,Y); 38(G,A,D,E,F,H,I,K,L,M,NT,V,W,Y); 39(N,C,E,H,I, L,P,Q,S,T,V,W,Y); 46(K,D,E,F,G,L,M,V,W); 51(F,A,D,E,G, I,L,M,N,P,R,S,T,Y); 52(L,A,E,G,I,M,R,T,V,W); 54(S,E,F, G,H,K,M,P,R,T,V,W,Y); 58(S,D,G,H,I,K,M,Q,R,W); 64(T, C,D,E,G,I,K,L,N,R,V,Y); 66(F,A,G,H,I,L,M,N,Q,R,S,T, V,W,Y); 68(A,C,G,I,S,T,V,W,Y); 69(L,A,D,G,H,I,K,N,S,T, W); 71(N,D,E,H,K,Q,R,S,T,V,W,Y); 72(T,A,D,E,F,H,I,K,L, N,P,R,S,V,Y); 75(L,A,D,E,G,H,I,M,N,Q,R,S,T,V,Y); 90(I, A,E,F,N,Q,T,V,Y); 93(L,D,H,I,K,N,P,Q,R,V,W); 94(N,D,G, K,M,P,R,S,T,V); 111(D,A,E,F,L,Q,T,V,W); 120(V,G,H,I,N, S,W,Y); 122(D,A,E,F,H,I,N,S,T,Y); 123(T,E,G,I,K,L,M,N, Q,W); 130(D,A,C,E,F,G,H,Q,R,T,V,W,Y); 131(A,C,H,I,K, N,Q,R,S,T,W,Y); 137(D,A,E,F,G,H,I,K,L,M,N,P,Q,R,S,T,V, W,Y); 140(V,C,E,F,I,L,M,N,Q,T); 162(N,D,E,F,G,H,I,K,M, P,Q,R,S,Y); 163(G,A,F,L,M,N,P,R,S,W,Y); 189(T,D,E,G,K, M,N,Q,R,S,V); 250(P,D,E,G,K,Q,R,S,T); 252(I,A,C,D,E,F, G,H,K,L,N,Q,R,S,T,W); and 264(L,C,E,G,H,M,N,P,Q,R,S, T), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have at least 30% but less than 50% of the modifications tested as suitable modifications include positions 18, 19, 20, 30, 31, 32, 47, 48, 49, 50, 53, 56, 60, 73, 74, 85, 86, 91, 95, 96, 97, 98, 99, 101, 105, 108, 115, 125, 127, 128, 132, 133, 151, 159, 164, 179, 183, 187, 188, 190, 216, 223, 232, 237, 244, 251, 254, 263, 267, and 269, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least 30% of the modifications tested as suitable modifications include the modifications 1(E,A,C,D,F,I,L,N, P,Q,R,S,T,V,W,Y); 2(V,F,G,H,I,K,L,M,P,T); 3(S,A,D,E,G,H, K,Q,R,T,Y); 4(Q,A,D,F,G,I,K,L,M,N,P,R,S,W,Y); 5(D,H,I, K,L,S,T,V,W,Y); 6(L,A,E,H,I,K,M,Q,T,V,Y); 8(N,A,E,G,H, I,K,L,M,T,V,W,Y); 9(Q,A,D,E,G,H,I,K,N,R,W,Y); 13(F,A, H,K,M,N,Q,T,V,Y); 18(A,C,H,K,M,N,Q,S,W); 19(A,C,G,I, L,T,V,W); 20(A,G,I,P,Q,S,T); 23(G,C,D,E,F,H,I,K,L,M,N,P, Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S, T,V,W,Y); 27(D,A,E,F,G,H,I,N,Q,R,S,T,V,Y); 28(A,D,E,F, G,H,I,L,M,N,P,Q,R,S); 29(P,C,E,G,H,I,K,L,M,Q,R,S,T,V, W,Y); 30(A,D,H,L,N,R,V,W); 31(G,D,E,H,M,P,Q,S,V); 32(T,A,I,M,Q,R,S); 33(N,D,E,F,K,L,M,Q,R,S); 37(T,A,C, D,E,F,G,H,I,K,L,M,P,Q,R,W,Y); 38(G,A,D,E,F,H,I,K,L,M, NT,V,W,Y); 39(N,C,E,H,I,L,P,Q,S,T,V,W,Y); 46(K,D,E,F, G,L,M,V,W); 47(A,D,E,F,H,M,T,W); 48(D,E,G,H,L,P,Q); 49(A,G,H,K,L,V,W); 50(T,A,D,F,K,L,R,S,W); 51(F,A,D,E, G,I,L,M,N,P,R,S,T,Y); 52(L,A,E,G,I,M,R,T,V,W); 53(Y,E, G,H,K,L,S,W); 54(S,E,F,G,H,K,M,P,R,T,V,W,Y); 56(E,H, K,R,T,V); 58(S,D,G,H,I,K,M,Q,R,W); 60(V,G,K,L,Y); 64(T,C,D,E,G,I,K,L,N,R,V,Y); 66(F,A,G,H,I,L,M,N,Q,R,S, T,V,W,Y); 68(A,C,G,I,S,T,V,W,Y); 69(L,A,D,G,H,I,K,N,S, T,W); 71(N,D,E,H,K,Q,R,S,T,V,W,Y); 72(T,A,D,E,F,H,I,K, L,N,P,R,S,V,Y); 73(N,E,G,H,K,R,S); 74(K,A,D,E,G,H,N,Q, S); 75(L,A,D,E,G,H,I,M,N,Q,R,S,T,V,Y); 85(S,F,H,I,N,Q, T); 86(I,L,M,P,Q,T,V,Y); 90(I,A,E,F,N,Q,T,V,Y); 91(G,E,F, H,I,M,Q,R); 93(L,D,H,I,K,N,P,Q,R,V,W); 94(N,D,G,K,M, P,R,S,T,V); 95(F,G,H,K,L,Q,T,V,W); 96(D,A,K,P,R,V); 97(L,A,D,I,M,Q,T); 98(K,D,E,H,I,M,Q); 99(E,D,K,P,Q,S, T,W); 101(N,C,D,E,H,M,Y); 105(S,A,D,E,F,K,P,W); 108 (R,E,F,K,M,Q,Y); 111(D,A,E,F,L,Q,T,V,W); 115(S,G,I,L, M,N,R,T,V); 120(V,G,H,I,N,S,W,Y); 122(D,A,E,F,H,I,N,S, T,Y); 123(T,E,G,I,K,L,M,N,Q,W); 125(R,C,G,I,N,Q,T,Y); 127(K,D,E,F,G,R,T); 128(V,C,H,I,L,N,S,W,Y); 130(D,A,C, E,F,G,H,Q,R,T,V,W,Y); 131(A,C,H,I,K,N,Q,R,S,T,W,Y); 132(V,C,D,H,I,K,Q,R,W); 133(R,E,F,I,N,Q,V); 137(D,A,E, F,G,H,I,K,L,M,N,P,Q,R,S,T,V,W,Y); 140(V,C,E,F,I,L,M,N, Q,T); 151(L,I,M,N,P,T,V,W); 159(L,E,M,Q,R,W); 162(N,D, E,F,G,H,I,K,M,P,Q,R,S,Y); 163(G,A,F,L,M,N,P,R,S,W,Y); 164(Y,D,N,R,S,V); 179(R,E,H,I,K,L,Q,V); 183(E,H,M,Q,S, T,V,Y); 187(V,G,H,L,N,Q,S,T,W); 188(Q,C,E,F,H,R,T); 189(T,D,E,G,K,M,N,Q,R,S,V); 190(G,D,H,R,S,Y); 216(S, D,G,N,Q,V,W); 223(K,A,H,L,M,Q,S,T,V); 232(R,C,D,I,L, M,P,T,W); 237(K,E,H,I,L,T,W,Y); 244(T,A,F,I,L,M,P,Q,S); 250(P,D,E,G,K,Q,R,S,T); 251(N,D,M,Q,S,T,W,Y); 252(I,A, C,D,E,F,G,H,K,L,N,Q,R,S,T,W); 254(D,A,H,K,N,P,T); 256 (P,A,D,S,T); 263(G,C,H,I,K,M,V); 264(L,C,E,G,H,M,N,P, Q,R,S,T); 267(T,G,I,L,M,P,W); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have at least 15% but less than 30% of the modifications tested as suitable modifications include positions 7, 11, 12, 15, 22, 35, 40, 42, 43, 44, 45, 61, 63, 65, 67, 76, 77, 84, 87, 114, 117, 119, 121, 134, 135, 136, 143, 154, 155, 156, 158, 165, 166, 168, 176, 180, 191, 199, 200, 202, 209, 211, 214, 217, 221, 224, 225, 228, 229, 231, 233, 248, 249, 253, 255, 256, 265, and 268, wherein the amino acid positions of the lipase variant are numbered by correspondence with the amino acid sequence of *Thermomyces lanuginosus* lipase TLL set forth in SEQ ID NO:4.

Lipolytic enzymes modificaitons of the present invention that have at least 15% of the modifications tested as suitable modifications include the modifications 1(E,A,C,D,F,I,L,N, P,Q,R,S,T,V,W,Y); 2(V,F,G,H,I,K,L,M,P,T); 3(S,A,D,E,G,H, K,Q,R,T,Y); 4(Q,A,D,F,G,I,K,L,M,N,P,R,S,W,Y); 5(D,H,I, K,L,S,T,V,W,Y); 6(L,A,E,H,I,K,M,Q,T,V,Y); 7(F,H,M,V, Y); 8(N,A,E,G,H,I,K,L,M,T,V,W,Y); 9(Q,A,D,E,G,H,I,K, N,R,W,Y); 11(N,H,K,V,Y); 12(L,F,H,V,W); 13(F,A,H,K,M, N,Q,T,V,Y); 15(Q,G,H,M,S); 18(A,C,H,K,M,N,Q,S,W); 19(A,C,G,I,L,T,V,W); 20(A,G,I,P,Q,S,T); 22(C,H,L,M); 23(G,C,D,E,F,H,I,K,L,M,N,P,Q,R,S,T,V,W); 24(K,A,D,E,F, H,I,L,M,N,P,R,T,V,W,Y); 25(N,A,C,D,E,G,H,I,K,L,S,T,V, W); 26(N,C,G,K,L,M,Q,S,T,V,W,Y); 27(D,A,E,F,G,H,I,N, Q,R,S,T,V,Y); 28(A,D,E,F,G,H,I,L,M,N,P,Q,R,S); 29(P,C,E, G,H,I,K,L,M,Q,R,S,T,V,W,Y); 30(A,D,H,L,N,R,V,W); 31(G,D,E,H,M,P,Q,S,V); 32(T,A,I,M,Q,R,S); 33(N,D,E,F, K,L,M,Q,R,S); 35(T,E,K,R); 37(T,A,C,D,E,F,G,H,I,K,L,M, P,Q,R,W,Y); 38(G,A,D,E,F,H,I,K,L,M,NT,V,W,Y); 39(N,C, E,H,I,L,P,Q,S,T,V,W,Y); 40(A,F,M,S,W); 42(P,C,G,I,V,W); 43(E,D,I,M,R,T); 44(V,H,I,T); 45(E,F,Q,V); 46(K,D,E,F,G,L,M,V,W); 47(A,D,E,F,H,M,T,W); 48(D,E,G,H,L,P,Q); 49(A,G,H,K,L,V,W); 50(T,A,D,F,K,L,R,S,W); 51(F,A,D,E,G,I,L,M,N,P,R,S,T,Y); 52(L,A,E,G,I,M,R,T,V,W); 53(Y,E,G,H,K,L,S,W); 54(S,E,F,G,H,K,M,P,R,T,VW,Y); 56(E,H,K,R,T,V); 58(S,D,G,H,I,K,M,Q,R,W); 60(V,G,K,L,Y); 61(G,A,D,L,R); 63(V,K,Q,T); 64(T,C,D,E,G,I,K,L,N,R,V,Y); 65(G,L,V,Y); 66(F,A,G,H,I,L,M,N,Q,R,S,T,VW,Y); 67(L,H,I,Q,V); 68(A,C,G,I,S,T,V,W,Y); 69(L,A,D,G,H,I,K,N,S,T,W); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T,V,Y); 76(I,H,S,V); 77(V,A,I,L,N,T); 84(R,H,Q,W); 85(S,F,H,I,N,Q,T); 86(I,L,M,P,Q,T,V,Y); 87(E,A,D,G,P,V); 90(I,A,E,F,N,Q,T,V,Y); 91(G,E,F,H,I,M,Q,R); 93(L,D,H,I,K,N,P,Q,R,V,W); 94(N,D,G,K,M,P,R,S,T,V); 95(F,G,H,K,L,Q,T,V,W); 96(D,A,K,P,R,V); 97(L,A,D,I,M,Q,T); 98(K,D,E,H,I,M,Q); 99(E,D,K,P,Q,S,T,W); 101(N,C,D,E,H,M,Y); 105(S,A,D,E,F,K,P,W); 108(R,E,F,K,M,Q,Y); 111(D,A,E,F,L,Q,T,V,W); 114(T,F,I,M,V); 115(S,G,I,L,M,N,R,T,V); 117(W,H,K,Q,V); 119(S,D,I,Q,T,V); 120(V,G,H,I,N,S,W,Y); 121(A,K,Q); 122(D,A,E,F,H,I,N,S,T,Y); 123(T,E,G,I,K,L,M,N,Q,W); 125(R,C,G,I,N,Q,T,Y); 127(K,D,E,F,G,R,T); 128(V,C,H,I,L,N,S,W,Y); 130(D,A,C,E,F,G,H,Q,R,T,V,W,Y); 131(A,C,H,I,K,N,Q,R,S,T,W,Y); 132(V,C,D,H,I,K,Q,R,W); 133(R,E,F,I,N,Q,V); 134(E,L,P,V); 135(H,F,K,T); 136(P,D,Q,R); 137(D,A,E,F,G,H,I,K,L,M,N,P,Q,R,S,T,V,W,Y); 140(V,C,E,F,I,L,M,N,Q,T); 143(T,A,G,N,S); 151(L,I,M,N,P,T,V,W); 154(V,F,I,L,M,Y); 155(A,G,S,T); 156(G,F,M,T,W); 158(D,E,F,Y); 159(L,E,M,Q,R,W); 162(N,D,E,F,G,H,I,K,M,P,Q,R,S,Y); 163(G,A,F,L,M,N,P,R,S,W,Y); 164(Y,D,N,R,S,V); 165(D,I,P,Y); 166(I,D,G,W); 168(V,G,L,Q); 176(V,F,I,L,N,W); 179(R,E,H,I,K,L,Q,V); 180(A,D,K,Q,T); 183(E,H,M,Q,S,T,V,Y); 187(V,G,H,L,N,Q,S,T,W); 188(Q,C,E,F,H,R,T); 189(T,D,E,G,K,M,N,Q,R,S,V); 190(G,D,H,R,S,Y); 191(G,F,L,V); 199 (T,G,N,V); 200(N,A,P,S); 202(I,L,M,P,V); 209(R,H,S,T); 211(F,I,R,T,W); 214(S,A,D,M); 216(S,D,G,N,Q,V,W); 217 (S,H,K,V); 221(W,F,G,Y); 223(K,A,H,L,M,Q,S,T,V); 224 (S,A,F,P); 225(G,C,E,K,R); 227(L,C,H,M); 228(V,A,E,R); 229(P,I,K,M,S); 231(T,G,H,K,L,M); 232(R,C,D,I,L,M,P,T,W); 233(N,D,G,H,Q); 237(K,E,H,I,L,T,W,Y); 244(T,A,F,I,L,M,P,Q,S); 248(N,D,L,Y); 249(Q,E,G,T); 250(P,D,E,G,K,Q,R,S,T); 251(N,D,M,Q,S,T,W,Y); 252(I,A,C,D,E,F,G,H,K,L,N,Q,R,S,T,W); 253(P,F,H,N,R); 254(D,A,H,K,N,P,T); 255(I,F,L,W); 256(P,A,D,S,T); 263(G,C,H,I,K,M,V); 264 (L,C,E,G,H,M,N,P,Q,R,S,T); 265(I,L,M,Q,R,W); 267(T,G,I,L,M,P,W); 268(C,D,H,N); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have at least one modification but less than 15% of the modifications tested as suitable modifications include positions 14, 16, 17, 34, 41, 55, 57, 59, 62, 70, 79, 92, 100, 102, 103, 106, 109, 110, 112, 118, 126, 138, 139, 142, 149, 152, 153, 167, 169, 170, 181, 184, 192, 193, 196, 198, 205, 206, 208, 210, 212, 213, 218, 226, 227, 230, 236, 238, 239, 242, 243, 246, 257, 259, 260, 262, and 266, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least one modification tested as a suitable modification include the modifications 1(E,A,C,D,F,I,L,N,P,Q,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S,W,Y); 5(D,H,I,K,L,S,T,V,W,Y); 6(L,A,E,H,I,K,M,Q,T,V,Y); 7(F,H,M,V,Y); 8(N,A,E,G,H,I,K,L,M,T,V,W,Y); 9(Q,A,D,E,G,H,I,K,N,R,W,Y); 11(N,H,K,V,Y); 12(L,F,H,V,W); 13(F,A,H,K,M,N,Q,T,V,Y); 14(A,S,V); 15(Q,G,H,M,S); 16(Y,H,W); 17(S,E); 18(A,C,H,K,M,N,Q,S,W); 19(A,C,G,I,L,T,V,W); 20(A,G,I,P,Q,S,T); 22(C,H,L,M); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M,N,P,Q,R,S); 29(P,C,E,G,H,I,K,L,M,Q,R,S,T,V,W,Y); 30(A,D,H,L,N,R,V,W); 31(G,D,E,H,M,P,Q,S,V); 32(T,A,I,M,Q,R,S); 33(N,D,E,F,K,L,M,Q,R,S); 34(I,P); 35(T,E,K,R); 37(T,A,C,D,E,F,G,H,I,K,L,M,P,Q,R,W,Y); 38(G,A,D,E,F,H,I,K,L,M,NT,V,W,Y); 39(N,C,E,H,I,L,P,Q,S,T,V,W,Y); 40(A,F,M,S,W); 41(C,V); 42(P,C,G,I,V,W); 43(E,D,I,M,R,T); 44(V,H,I,T); 45(E,F,Q,V); 46(K,D,E,F,G,L,M,V,W); 47(A,D,E,F,H,M,T,W); 48(D,E,G,H,L,P,Q); 49(A,G,H,K,L,V,W); 50(T,A,D,F,K,L,R,S,W); 51(F,A,D,E,G,I,L,M,N,P,R,S,T,Y); 52(L,A,E,G,I,M,R,T,V,W); 53(Y,E,G,H,K,L,S,W); 54(S,E,F,G,H,K,M,P,R,T,VW,Y); 55(F,G,W); 56(E,H,K,R,T,V); 57(D,S); 58(S,D,G,H,I,K,M,Q,R,W); 59(G,D); 60(V,G,K,L,Y); 61(G,A,D,L,R); 62(D,N); 63(V,K,Q,T); 64(T,C,D,E,G,I,K,L,N,R,V,Y); 65(G,L,V,Y); 66(F,A,G,H,I,L,M,N,Q,R,S,T,VW,Y); 67(L,H,I,Q,V); 68(A,C,G,I,S,T,V,W,Y); 69(L,A,D,G,H,I,K,N,S,T,W); 70(D,S); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T,V,Y); 76(I,H,S,V); 77(V,A,I,L,N,T); 79(S,A,M); 84(R,H,Q,W); 85(S,F,H,I,N,Q,T); 86(I,L,M,P,Q,T,V,Y); 87(E,A,D,G,P,V); 90(I,A,E,F,N,Q,T,V,Y); 91(G,E,F,H,I,M,Q,R); 92(N,A,T); 93(L,D,H,I,K,N,P,Q,R,V,W); 94(N,D,G,K,M,P,R,S,T,V); 95(F,G,H,K,L,Q,T,V,W); 96(D,A,K,P,R,V); 97(L,A,D,I,M,Q,T); 98(K,D,E,H,I,M,Q); 99(E,D,K,P,Q,S,T,W); 100(I,M); 101(N,C,D,E,H,M,Y); 102 (D,H); 103(I,Y); 105(S,A,D,E,F,K,P,W); 106(G,H); 108(R,E,F,K,M,Q,Y); 109(G,T); 110(H,N,S); 111(D,A,E,F,L,Q,T,V,W); 112(G,F,Q); 114(T,F,I,M,V); 115(S,G,I,L,M,N,R,T,V); 117(W,H,K,Q,V); 118(R,P); 119(S,D,I,Q,T,V); 120(V,G,H,I,N,S,W,Y); 121(A,K,Q); 122(D,A,E,F,H,I,N,S,T,Y); 123(T,E,G,I,K,L,M,N,Q,W); 125(R,C,G,I,N,Q,T,Y); 126(Q,I,M); 127(K,D,E,F,G,R,T); 128(V,C,H,I,L,N,S,W,Y); 130 (D,A,C,E,F,G,H,Q,R,T,V,W,Y); 131(A,C,H,I,K,N,Q,R,S,T,W,Y); 132(V,C,D,H,I,K,Q,R,W); 133(R,E,F,I,N,Q,V); 134 (E,L,P,V); 135(H,F,K,T); 136(P,D,Q,R); 137(D,A,E,F,G,H,I,K,L,M,N,P,Q,R,S,T,V,W,Y); 138(Y,F); 139(RLT); 140(V,C,E,F,I,L,M,N,Q,T); 142(F,H,Y); 143(T,A,G,N,S); 149(G,A); 151(L,I,M,N,P,T,V,W); 152(A,I,V); 153(T,S); 154(V,F,I,L,M,Y); 155(A,G,S,T); 156(G,F,M,T,W); 158(D,E,F,Y); 159(L,E,M,Q,R,W); 162(N,D,E,F,G,H,I,K,M,P,Q,R,S,Y); 163(G,A,F,L,M,N,P,R,S,W,Y); 164(Y,D,N,R,S,V); 165(D,I,P,Y); 166(I,D,G,W); 167(D,N); 168(V,G,L,Q); 169(F,S,Y); 170(S,G); 176(V,F,I,L,N,W); 179(R,E,H,I,K,L,Q,V); 180 (A,D,K,Q,T); 181(F,L); 183(E,H,M,Q,S,T,V,Y); 184(F,W,Y); 187(V,G,H,L,N,Q,S,T,W); 188(Q,C,E,F,H,R,T); 189(T,D,E,G,K,M,N,Q,R,S,V); 190(G,D,H,R,S,Y); 191(G,F,L,V); 192(T,N,P); 193(L,T); 196(I,V); 198(H,G,S); 199(T,G,N,V); 200(N,A,P,S); 202(I,L,M,P,V); 205(R,D); 206(L,N); 208(P,E,N); 209(R,H,S,T); 210(E,S); 211(F,I,R,T,W); 212 (G,Q); 213(Y,S); 214(S,A,D,M); 216(S,D,G,N,Q,V,W); 217 (S,H,K,V); 218(P,T); 221(W,F,G,Y); 223(K,A,H,L,M,Q,S,T,V); 224(S,A,F,P); 225(G,C,E,K,R); 226(T,D,N); 227(L,C,H,M); 228(V,A,E,R); 229(P,I,K,M,S); 230(V,W); 231(T,G,H,K,L,M); 232(R,C,D,I,L,M,P,T,W); 233(N,D,G,H,Q); 236 (V,W); 237(K,E,H,I,L,T,W,Y); 238(I,V); 239(E,K); 242(D,T); 243(A,S); 244(T,A,F,I,L,M,P,Q,S); 246(G,I); 248(N,D,L,Y); 249(Q,E,G,T); 250(P,D,E,G,K,Q,R,S,T); 251(N,D,M, Q,S,T,W,Y); 252(I,A,C,D,E,F,G,H,K,L,N,Q,R,S,T,W); 253 (P,F,H,N,R); 254(D,A,H,K,N,P,T); 255(I,F,L,W); 256(P,A,D,S,T); 257(A,W,Y); 259(L,W,Y); 260(W,P); 262(F,D,K); 263(G,C,H,I,K,M,V); 264(L,C,E,G,H,M,N,P,Q,R,S,T); 265 (I,L,M,Q,R,W); 266(G,E); 267(T,G,I,L,M,P,W); 268(C,D,H,N); and 269(L,D,F,M,Q,V,W), wherein the amino acid positions of the lipase variant are numbered by correspondence with the amino acid sequence of *Thermomyces lanuginosus* lipase TLL set forth in SEQ ID NO:4.

Additional lipolytic enzymes modifications of the present invention that have a suitable modification include the modifications 11(A,E,I), 23(A), 24(Q,S), 27(K,L), 29(N), 30(E,G,I,S,Y), 31(T), 33(C,I,P,T,V), 45(A,G,S,T), 48(N,R,T,V), 49(C,Y), 50(M), 51(H,V), 56(A,M,N,S), 58(A,F), 71(C,F,P), 73(Q,T), 74(I,M,T,W), 75(K), 91(K,N,Y), 94(A,H), 101(A), 108(A), 111(G,H,I,K,M,S,Y), 122(K,L,Q), 128 (T,V), 130(K,M), 133(D,H,L,W), 135(A,D,M,N,Y), 140(Y), 159(G), 163(Q), 183(C), 187(C,I), 188(A,M,W), 190(W), 227(A,I,S), 233(F,I,V), 251(V), and 252(M,V).

These amino acid positions can be considered useful positions for combinatorial modifications to a parent lipolytic enzyme. Thus, the invention includes lipolytic enzymes having one or more modifications at any of the above positions.

Suitable Modifications of Lipolytic Enzymes

The invention includes enzyme variants of lipolytic enzymes having one or more modifications from a parent lipolytic enzyme. The enzyme variants can be useful in a detergent composition by having a minimum performing index for wash performance, stability of the enzyme in detergent compositions and thermostability of the enzyme, while having at least one of these characteristics improved from a parent lipolytic enzyme.

Lipolytic enzymes modifications of the present invention that meet all three of the suitability criteria include 1 (A,D,F,I,N,P,S,W,Y), 2 (I,L), 3 (D,G,Y), 4 (D,F,W), 5 (H,I,L,S,T,V,Y), 6 (I,T), 7 (Y), 8 (G,H,I,L,M,T,V,W,Y), 9 (H,K), 11 (V), 13 (H,N), 14 (S), 16 (W), 17 (E), 18 (K), 19 (G), 20 (T), 23 (D,E,H,I,K,N,Q,T,V), 24 (A,D,E,H,I,L,N,P,T,V,W), 25 (I,L,T), 26 (G,K,M,S,T,V,W,Y), 27 (A,E,G,H,I,N,Q,R,S,T,V,Y), 28 (D,E,I,N,S), 29 (E,H,K,L,M,R,T,V), 31 (D,H,S), 33 (D,E,F,L,Q,R,S), 34 (P), 37 (D,E,G,I,K,P,Q,W), 38 (D,F,H,I,K,L,M,N,Y), 39 (E,H,I,L,S,V), 40 (M,S), 42 (G,I,W), 43 (R,T), 44 (I), 45 (F,V), 46 (D,L,M), 47 (H), 48 (E,H,P,Q), 49 (V), 50 (L,R,S), 51 (A,E,G,I,L,M,S), 52 (A,G,I,V), 54 (P,T,V), 56 (H,K,R,T), 58 (M), 60 (G), 63 (T), 64 (G), 66 (H,M,W), 67 (I,V), 68 (G,I,S,T,V), 69 (I,K,S,T), 70 (S), 71 (D,H,K,Q,R,S,T), 72 (A,D,E,F,H,I,L,N,R,S,V,Y), 73 (H,R,S), 74 (H,S), 75 (A,E,G,H,I,Q,S,T,V), 79 (A), 85 (T), 86 (P,T), 87 (G), 90 (A,E,F,N), 91 (E,H,I,M,Q,R), 92 (T), 94 (R), 95 (G,Q,V,W), 96 (A,K), 97 (D,T), 98 (Q), 99 (D,S,T,W), 101 (D,H,Y), 105 (K), 108 (K,Q,Y), 111 (A,E,L,Q,T,V), 114 (F,I,M,V), 115 (T), 118 (P), 119 (T), 120 (Y), 121 (K), 122 (H,I), 123 (G,M,N,W), 125 (G,Q), 127 (G,T), 130 (A,G,H,T), 131 (H,I,Q), 132 (H,R), 134 (L,V), 135 (K), 137 (E,G,H,K,Q,T,Y), 139 (T), 151 (I,T,V), 154 (I,L), 155 (G,S), 158 (E,F), 162 (G,R), 163 (N,P,Y), 164 (V), 166 (G), 176 (I,L), 179 (L,Q,V), 180 (K), 181 (L), 187 (G,H,L,N,Q,S,T,W), 188 (C,T), 189 (D,G,N,Q,R,S), 191 (F,L,V), 196 (V), 199 (G), 202 (P,V), 208 (E), 211 (I,W), 216 (N,W), 217 (K), 223 (Q,S,T,V), 225 (E,K,R), 227 (M), 228 (R), 232 (I,M,T), 233 (D,G,H,Q), 237 (I,L,Y), 242 (T), 244 (I), 250 (Q,R), 251 (D,W), 252 (A,D,G,H,Q,R,S,T), 255 (L), 256 (A,S), 257 (Y), 262 (D), 264 (E,M,N,P,Q,R), 265 (M,Q), 267 (L,W), and 269 (D,M,Q,V,W), wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that meet both a) and b), but not c) of the suitability criteria include 1 (Q,T), 2 (F,G,M,P), 3 (K,T), 4 (A,G,I,K,L,M,N,R,S), 5 (K,W), 6 (E,M), 8 (A,E), 9 (E,G,N,R), 11 (H,K,Y), 12 (F,H,V), 13 (Q), 15 (S), 18 (Q), 19 (C), 20 (G,S), 23 (C,F,L,M,S,W), 24 (Y), 25 (C,H,K), 26 (C), 27 (F), 28 (H,M,P,Q,R), 29 (Q,W,Y), 30 (D,V), 31 (E,Q), 32 (A,I,M,R,S), 35 (K), 37 (C), 38 (V,W), 39 (P,T,Y), 40 (W), 42 (V), 43 (D,M), 45 (Q), 46 (F,G,V,W), 47 (T), 50 (A), 51 (N,R,T), 52 (E,R,W), 53 (E,G,H,K,S), 54 (R,Y), 55 (G), 56 (V), 64 (C,E,N,V), 66 (N,Q,R), 67 (Q), 69 (A,G,H,N,W), 71 (V,W,Y), 72 (P), 73 (E,G,K), 74 (N,Q), 75 (D,N,R,Y), 76 (H), 77 (I,L,N,T), 86 (L,M), 87 (P,V), 90 (Q,T), 91 (F), 94 (D), 97 (Q), 98 (D,E,I), 99 (K), 105 (A,D,E,P), 108 (E,M), 122 (E,N), 123 (E,L,Q), 125 (N,T), 126 (I), 127 (E,F,R), 128 (H,S), 130 (F,Q), 131 (R,W,Y), 132 (D,K,W), 133 (E,Q), 135 (F,T), 136 (D,Q), 137 (S,V), 139 (L), 140 (F,M,Q,T), 143 (A,G,S), 149 (A), 151 (N), 154 (F), 156 (F,W), 158 (Y), 159 (E), 163 (S,W), 164 (N,S), 165 (I), 166 (D,W), 167 (N), 168 (L), 179 (E,I), 183 (V), 188 (H), 189 (K,V), 200 (A), 205 (D), 209 (S,T), 214 (D), 216 (G,Q), 217 (H), 218 (T), 223 (M), 226 (N), 228 (E), 229 (K), 231 (K,L,M), 252 (K,L,N), 254 (H), 255 (F), 256 (T), 263 (I,V), 264 (H,S,T), 267 (P), and 269 (F), wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that meet a) or both b) and c), but not all three of the suitability criteria include 1 (E,R,V), 2 (V,H,T), 3 (S,E,Q), 4 (Q,Y), 5 (D), 6 (L,Q,V), 7 (F), 8 (N), 9 (Q,A,I), 11 (N), 12 (L), 13 (F), 14 (A), 15 (Q), 16 (Y), 17 (S), 18 (A,C,H,S), 19 (A,T), 20 (A,P), 22 (C), 23 (G,P), 24 (K,F), 25 (N,A,D,G,V,W), 26 (N,L,Q), 27 (D), 28 (A,F,G,L), 29 (P,C,I), 30 (A,H,R,W), 31 (G), 32 (T,Q), 33 (N,K), 34 (I), 35 (T,E,R), 37 (T,A,F,L,M), 38 (G,T), 39 (N), 40 (A), 41 (C), 42 (P), 43 (E,I), 44 (V,H,T), 45 (E), 46 (K,E), 47 (A,D,E,F,M), 48 (D), 49 (A,H,K), 50 (T,D,W), 51 (F), 52 (L,T), 53 (Y,L,W), 54 (S), 55 (F), 56 (E), 57 (D), 58 (S,G,H,K,Q,W), 59 (G), 60 (V), 61 (G,L), 62 (D), 63 (V), 64 (T,D,I,L), 65 (G,V), 66 (F,I,L,V), 67 (L), 68 (A,C,W), 69 (L), 70 (D), 71 (N,E), 72 (T,K), 73 (N), 74 (K,A,D,G), 75 (L), 76 (I,V), 77 (V,A), 79 (S), 84 (R), 85 (S,H,N,Q), 86 (I,V,Y), 87 (E,D), 90 (I,V), 91 (G), 92 (N), 93 (L,D,K,Q,R), 94 (N,G,T,V), 95 (F,K,L), 96 (D), 97 (L,A,M), 98 (K,H), 99 (E), 100 (I), 101 (N), 102 (D), 103 (I), 105 (S,W), 106 (G), 108 (R,F), 109 (G), 110 (H,S), 111 (D), 112 (G), 114 (T), 115 (S,G,M,R,V), 117 (W,H,V), 118 (R), 119 (S,D,I), 120 (V,G,H,N,S,W), 121 (A), 122 (D,A,F), 123 (T), 125 (R,Y), 126 (Q), 127 (K), 128 (V,C,I), 130 (D,V,W,Y), 131 (A,K,S,T), 132 (V,Q), 133 (R,I), 134 (E), 135 (H), 136 (P), 137 (D,I,R,W), 138 (Y), 139 (R), 140 (V), 142 (F,H,Y), 143 (T), 149 (G), 151 (L,M,W), 152 (A), 153 (T,S), 154 (V), 155 (A), 156 (G,M), 158 (D), 159 (L,Q,R), 162 (N,D,E,F,H,I,K,Q,S), 163 (G,F,L), 164 (Y), 165 (D), 166 (I), 167 (D), 168 (V,G), 169 (F,S), 170 (S), 176 (V), 179 (R,H,K), 180 (A,T), 181 (F), 183 (E), 184 (F,Y), 187 (V), 188 (Q), 189 (T), 190 (G), 191 (G), 192 (T), 193 (L,T), 196 (I), 198 (H,G,S), 199 (T), 200 (N,S), 202 (I,L), 205 (R), 206 (L), 208 (P), 209 (R,H), 210 (E), 211 (F,R,T), 212 (G), 213 (Y), 214 (S,A), 216 (S,V), 217 (S,V), 218 (P), 221 (W), 223 (K,A), 224 (S), 225 (G), 226 (T), 227 (L,H), 228 (V), 229 (P), 230 (V,W), 231 (T,H), 232 (R,P), 233 (N), 236 (V), 237 (K,H,T,W), 238 (I), 239 (E), 242 (D), 243 (A), 244 (T,Q,S), 246 (G), 248 (N), 249 (Q), 250 (P,S), 251 (N), 252 (I,C,E), 253 (P,R), 254 (D,T), 255 (I), 256 (P), 257 (A), 259 (L), 260 (W), 262 (F), 263 (G,K), 264 (L,C,G), 265 (I), 266 (G), 267 (T,G,M), 268 (C,H), and 269 (L), wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that meet b) only (meets b) but not a) or c)) of the suitability criteria include 2 (K), 3 (A,H), 4 (P), 6 (K,Y), 7 (H), 9 (D,W), 12 (W), 13 (A,M,Y), 15 (M), 16 (H), 20 (Q), 22 (H), 23 (R), 25 (S), 29 (G,S), 30 (L,N), 33 (M), 37 (H), 39 (Q), 40 (F), 47 (W), 48 (G), 50 (F,K), 51 (D,P,Y), 52 (M), 54 (F,G,K,W), 55 (W), 58 (I), 60 (L), 64 (K,R,Y), 65 (L), 66 (G,Y), 67 (H), 68 (Y), 69 (D), 75 (M), 84 (H), 86 (Q), 90 (Y), 92 (A), 93 (I,P,V), 94 (S), 95 (H,T), 96 (V), 98 (M), 100 (M), 115 (N), 117 (Q), 122 (S,T,Y), 125 (I), 126 (M), 127 (D), 128 (Y), 130 (C,R), 132 (I), 134 (P), 140 (C), 151 (P), 152 (V), 156 (T), 164 (D,R), 165 (Y), 188 (F), 208 (N), 213 (S), 216 (D), 227 (C), 229 (I), 232 (C,L), 237 (E), 249 (E), 250 (E), 252 (F), 254 (A,K), 257 (W), and 267 (I), wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that meet c) only (meets c) but not a) or b)) of the suitability criteria include 1 (C,L), 3 (R), 6 (A,H), 7 (M,V), 8 (K), 9 (Y), 13 (K,T,V), 14 (V), 15 (G,H), 18 (M,N,W), 19 (I,L,V, W), 20 (I), 22 (L,M), 24 (M,R), 25 (E), 31 (M,P,V), 37 (R,Y), 38 (A,E), 39 (C,W), 41 (V), 42 (C), 48 (L), 49 (G,L,W), 54 (E,H,M), 57 (S), 58 (D,R), 59 (D), 60 (K,Y), 61 (A,D,R), 62 (N), 63 (K,Q), 65 (Y), 66 (A,S,T), 74 (E), 76 (S), 79 (M), 84 (Q,W), 85 (F,I), 87 (A), 93 (H,N,W), 94 (K,M,P), 96 (P,R), 97 (I), 99 (P,Q), 101 (C,E,M), 102 (H), 103 (Y), 105 (F), 106 (H), 109 (T), 110 (N), 111 (F,W), 112 (F,Q), 115 (I,L), 117 (K), 119 (Q,V), 120 (I), 121 (Q), 123 (I,K), 125 (C), 128 (L,N,W), 130 (E), 131 (C,N), 132 (C), 133 (F,N,V), 136 (R), 137 (A,F,L,M,N,P), 138 (F), 140 (E,I,L,N), 143 (N), 152 (I), 154 (M,Y), 155 (T), 159 (M,W), 162 (M,P,Y), 163 (A,M,R), 165 (P), 168 (Q), 169 (Y), 170 (G), 176 (F,N,W), 180 (D,Q), 183 (H,M,Q,S,T,Y), 184 (W), 188 (E,R), 189 (E,M), 190 (D,H,R,S,Y), 192 (N,P), 199 (N,V), 200 (P), 202 (M), 206 (N), 210 (S), 212 (Q), 214 (M), 221 (F,G,Y), 223 (H,L), 224 (A,F,P), 225 (C), 226 (D), 228 (A), 229 (M,S), 231 (G), 232 (D,W), 236 (W), 238 (V), 239 (K), 243 (S), 244 (A,F,L,M,P), 246 (I), 248 (D,L,Y), 249 (G,T), 250 (D,G,K,T), 251 (M,Q,S,T,Y), 252 (W), 253 (F,H,N), 254 (N,P), 255 (W), 256 (D), 259 (W,Y), 260 (P), 262 (K), 263 (C,H,M), 265 (L,R,W), 266 (E), and 268 (D,N), wherein the amino acid positions of the lipase variant are numbered by correspondence with the amino acid sequence of *Thermomyces lanuginosus* lipase TLL set forth in SEQ ID NO:4.

Surface Modifications

The invention includes enzyme variants of lipolytic enzymes having one or more modifications at a surface exposed amino acid. Surface modifications in the enzyme variants can be useful in a detergent composition by having a minimum performing index for wash performance, stability of the enzyme in detergent compositions and thermostability of the enzyme, while having at least one of these characteristics improved from a parent lipolytic enzyme. In some embodiments, the surface modification changes the hydrophobicity and/or charge of the amino acid at that position. Hydrophobicity can be determined using techniques known in the art, such as those described in White and Wimley (White, S. H. and Wimley, W. C. (1999) Annu. Rev. Biophys. Biomol. Struct. 28:319-65.

As used herein, "surface property" can be used in reference to electrostatic charge, as well as properties such as the hydrophobicity and hydrophilicity exhibited by the surface of a protein.

Lipolytic enzymes positions of the present invention that have at least one of the surface modifications as suitable modifications include positions 18, 27, 29, 33, 51, 58, 72, 75, 101, 108, 114, 121, 135, 137, 156, 163, 187, 250, 252, and 264, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least one of the surface modifications as suitable modifications include the modifications A018K, D027N, D027S, D027T, D027V, P029E, N033D, N033E, N033R, F051T, S058M, T072R, L075Q, N101D, R108K, R108Q, R108Y, T114F, T114I, A121K, H135F, D137V, G156W, G163Y, V187N, V187W, P250E, I252A, I252T, or L264P, wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have at least one of the surface modifications as suitable modifications where the change is a change in hydrophobicity (but not charge) include positions 18, 27, 29, 33, 51, 58, 72, 75, 101, 108, 114, 121, 135, 137, 156, 163, 187, 250, 252, and 264, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least one of the surface modifications as suitable modifications where the change is a change in hydrophobicity (but not charge) include the modifications A018K, D027N, D027S, D027T, D027V, P029E, N033D, N033E, N033R, F051T, S058M, T072R, L075Q, N101D, R108K, R108Q, R108Y, T114F, T114I, A121K, H135F, D137V, G156W, G163Y, V187N, V187W, P250E, I252A, I252T, or L264P, wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have at least one of the surface modifications as suitable modifications where the change is a change in charge (but not hydrophobicity) include position 18, 27, 29, 33, 72, 101, 108, 121, 137, and 250, wherein the amino acid positions of the lipase variant are numbered by correspondence with the amino acid sequence of *Thermomyces lanuginosus* lipase TLL set forth in SEQ ID NO:4.

Lipolytic enzymes modifications of the present invention that have at least one of the surface modifications as suitable modifications where the change is a change in charge (but not hydrophobicity) include the modifications A018K, D027N, D027S, D027T, D027V, P029E, N033D, N033E, N033R, T072R, N101D, R108Q, R108Y, A121K, D137V, or P250E, wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and detergent stability is greater than or equal to 0.8, and wherein the minimum performance indices (PI) relative to TLL parent for detergent performance at half dose is greater than or equal to 1.1, and wherein the productive modification is selected from the group consisting of 1 (S), 5 (H, I, S, T), 8 (H), 9 (K, N), 11 (H, K), 13 (N), 19 (G), 23 (K, N, Q R), 27 (Q, R), 29 (K, R), 32 (A), 33 (D), 37 (G, H, Q), 38 (F, L, M, W, Y), 39 (I, L), 42 (W), 43 (D, I, R, T), 45 (F, Q, V), 51 (M), 53 (E), 54 (P), 56 (H, K, R), 58 (H, K, Q, W), 69 (R), 73 (R), 75 (A, R), 75 (T), 77 (I, L, T), 90 (F,T), 91 (I,Q), 94 (R), 105 (P), 108 (K), 122 (F), 125 (T), 130 (A, R), 132 (K,R), 134 (L), 137 (R), 151 (T), 155 (S), 156 (W), 163 (F, P), 164 (R), 180 (K), 183 (V), 184 (Y), 187 (G, H, N, Q, S, T, W), 189 (G, Q), 211 (I), 214 (A), 228 (R), 232 (P), 233 (Q), 244 (I), 252 (N), and 265 (Q), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and detergent stability is greater than or equal to 0.8, and wherein the minimum performance indices (PI) relative to TLL parent for detergent performance at half dose with adjuvant is greater than or equal to 1.1, and wherein the productive modification is selected from the group consisting of 1 (S), 3 (T), 4 (F), 5 (H, I, S, T), 8 (H, T, V), 9 (G, H, K), 11 (K), 12 (V, W), 18 (K), 19 (G), 23 (K, Q, R), 27 (R, S), 32 (I), 38 (F, L, M, W, Y), 39 (I, P), 43 (I, R, T), 45 (F, Q), 53 (K), 54 (P), 56 (K, R), 58 (H, Q), 75 (G, Q, R), 77 (I), 90 (T), 91 (I, Q), 105 (P), 123 (N), 127 (F), 130 (A, F, H, Q, R), 131 (R), 136 (Q), 137 (R, S), 143 (S), 156 (T), 162 (G), 163 (S), 164 (R, V), 166 (G), 180 (K), 187 (G, H, N, Q, S, T, W), 188 (F), 189 (D, G), 199 (G), 228 (R), 252 (N), 264 (R), and 265 (Q), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and detergent stability is greater than or equal to 0.8, and wherein the minimum performance indices (PI) relative to TLL parent for detergent performance at full dose is greater than or equal to 1.1, and wherein the productive modification is selected from the group consisting of 1 (S), 5 (H, I, T), 23 (E, Q), 29 (H, I, R, T), 39 (H, I), 43 (R, T), 54 (T), 58 (Q), 115 (T), 130 (A, R), 154 (L), 158 (E), 180 (K), 187 (T), 228 (R), and 269 (W), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and hydrolysis of pNPO substrate at pH 8 is greater than or equal to 0.8, and wherein the minimum performance indices (PI) relative to TLL parent for theromostability is greater than or equal to 1.1, and wherein the productive modification is selected from the group consisting of 2 (I), 11 (K), 15 (S), 18 (K), 23 (C,D,E,F,H,I,K,M, N,Q,S,T,V), 24 (H), 26 (T), 27 (A,G,H, N,Q,R,S,T,V), 29 (E), 37 (P), 48 (E, Q), 50 (S), 51 (A,I,L, S,T), 56 (K,V), 58 (M), 66 (N, Q), 75 (A, G, Q, R), 77 (I, T), 91 (E, Q), 94 (R), 96 (K), 99 (D, S), 101 (D, H), 108 (K, M, Y), 111 (A, E, Q), 114 (F, I, V), 117 (Q), 120 (N), 121 (K), 135 (F), 137 (I, Q, R), 154 (F, I, L), 155 (G, S), 156 (W), 163 (F), 169 (S), 176 (I), 187 (H, N, W), 226 (N), 250 (E), 252 (A), 256 (T), 264 (C, H, M, P, Q, S), 265 (M), and 269 (Q), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and hydrolysis of pNPO substrate at pH 8 is greater than or equal to 0.8, and wherein the minimum performance indices (PI) relative to TLL parent for detergent stability is greater than or equal to 1.1, and wherein the productive modification is selected from the group consisting of 12 (F), 13 (Q), 15 (S), 19 (C, G), 20 (P), 23 (D, E, F, I, V), 24 (W), 26 (C, T, W, Y), 28 (D, P), 31 (E), 34 (P), 37 (C, D), 39 (E, L, P), 42 (I, V), 45 (F, V), 46 (F, G, L, W), 47 (F, M, T, W), 49 (H, V), 51 (A, G, I, L, M, S, T), 60 (L), 64 (V), 66 (Q), 68 (S, T, V), 73 (E, G, R, S), 75 (E, G, Q, R), 77 (A, L, N, T), 91 (E, Q), 94 (D), 108 (E, F, M, Q, Y), 114 (F, I, V), 127 (T), 128 (H, S, Y), 131 (R, W, Y), 132 (D), 133 (E, Q), 136 (D, Q), 139 (M), 140 (F, M, Q), 142 (Y), 154 (I), 155 (S), 156 (W), 159 (E, R), 163 (F, L, P, Y), 168 (G, L), 179 (L), 187 (H, N, Q, T), 188 (F), 189 (D), 205 (D), 208 (E), 209 (S), 214 (D), 223 (T), 225 (E), 228 (E), 237 (L, Y), 250 (E), 251 (D), 252 (A), 256 (T), 264 (C, H, P, Q, S), and 265 (M), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and hydrolysis of pNPO substrate at pH 8 is greater than or equal to 0.8, and wherein the minimum performance indices (PI) relative to TLL parent for LAS stability is greater than or equal to 1.1, and wherein the productive modification is selected from the group consisting of 1 (F, R), 4 (K, L, N, W), 5 (K), 11 (K), 23 (K), 27 (A, H, N, R, S, T, V), 37 (P), 38 (H, K, L, W, Y), 42 (V), 43 (I, R), 45 (F, Q, V), 47 (T), 49 (V), 51 (I, M, S), 56 (H, K, S, T), 58 (M, Q), 73 (S), 75 (D, E, G, Q, R), 91 (Q), 94 (R), 101 (D), 108 (K), 111 (A), 119 (D, T), 120 (Y), 154 (I), 179 (L), 187 (T), 189 (D, Q), 200 (A), 209 (S), 211 (W), 226 (N), 250 (E, Q), 251 (W), 252 (A), and 256 (T), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPB hydrolysis is greater than or equal to 1.1, and wherein the productive modification is selected from the group consisting of 2 (I,L), 3 (D), 4 (D,I,L,W), 5 (H,Y), 8 (H,M), 9 (K), 11 (H,K), 18 (K), 23 (K), 24 (A,T), 26 (K,T), 27 (A,I,Q,T), 29 (H,I,K,R,T,V), 30 (R,V), 32 (S), 35 (K), 37 (G), 40 (M), 54 (V), 69 (A,K), 71 (R), 72 (L), 74 (A), 75 (M,S), 91 (I), 94 (R), 101 (Y), 108 (K,Y), 111 (L,T,V), 114 (I), 122 (T,Y), 123 (Q), 125 (Q), 130 (F,H), 132 (H,W), 134 (L,V), 137 (H,K,S,T,W,Y), 151

(T,W), 155 (G), 156 (W), 162 (G), 163 (Y), 166 (G), 176 (I), 180 (K), 187 (H,S,T,W), 189 (K), 232 (L,P), 233 (D,H), 237 (L,Y), 244 (I), 252 (L,T), 255 (L), 263 (I,V), 265 (M), and 269 (M), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPO hydrolysis is greater than or equal to 1.1, and wherein the productive modification is selected from the group consisting of 1 (D), 2 (L), 3 (D,T), 4 (A,D,L,M), 5 (H,Y), 8 (A,E,M), 9 (R), 18 (K), 23 (D,E,F,N,Q), 24 (A,D,E,H,N,T), 26 (G,K), 27 (A,E,I,N,Q,T), 29 (E,Q,R), 33 (D,E,F,M,Q,R,S), 37 (D,E,P,Q), 38 (D,N), 40 (M), 48 (E,Q), 49 (V), 50 (E,F), 51 (I,L,T), 54 (F,R), 56 (H,K,R,T), 58 (M,Q), 64 (N), 66 (Q), 74 (Q), 75 (E,M,N,Q,R), 77 (A,I,L,T), 87 (P), 90 (E,F,Q), 101 (D), 105 (D,P), 108 (K,Q,Y), 111 (A,E,L,Q,T), 114 (F,M), 115 (R), 117 (Q), 120 (N), 122 (Y), 123 (E,L,M,N,Q), 125 (Q), 127 (E,F,R), 130 (A,F,H,Q), 132 (K,Q,R), 134 (L), 137 (E,G,H,I,K,Q,R,S,T,V,W,Y), 154 (F,L), 155 (G,S), 156 (F,W), 158 (E,F,Y), 162 (G,R), 163 (F,P,S,W,Y), 169 (S), 176 (I), 180 (K), 187 (H,N,Q,S,T,W), 189 (D,Q,R), 225 (E), 227 (M), 228 (E), 232 (P), 233 (D,G,Q), 264 (E,M,N,P,Q,R,S,T), 265 (M), and 269 (M,Q), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPP hydrolysis is greater than or equal to 1.1, and wherein the productive modification is selected from the group consisting of 1 (Q,S), 3 (D,T), 4 (A,D,L,M), 5 (H,S,Y), 9 (M), 11 (K), 12 (F), 15 (S), 23 (F), 27 (E,N,Q,T), 29 (R), 32 (A,Q,S), 33 (D,Q), 35 (E,K,R), 40 (M), 48 (Q), 51 (I,L,M,T), 56 (H,K,R,T), 58 (M,Q), 71 (E), 75 (R), 77 (I,T), 87 (P), 105 (A), 108 (K), 111 (A,L), 114 (M), 115 (R), 127 (E,F), 130 (A), 132 (Q,R,W), 134 (L), 137 (E,G,H,I,K,Q,R,S,Y), 143 (A), 155 (S), 162 (G), 163 (F,P,S,W,Y), 164 (D,R), 165 (I,Y), 187 (H,N,Q,S,W), 189 (R), 225 (E), 227 (A,M), 232 (P), 233 (Q), 244 (I), 252 (A,K,L,R), 263 (I,V), 264 (H,R,T), and 269 (V), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPB and pNPO hydrolysis is greater than or equal to 1.1, and wherein the productive modification is selected from the group consisting of 2 (L), 3 (D), 4 (D,L), 5 (H,Y), 8 (M), 18 (K), 24 (A,T), 26 (K), 27 (A,I,Q,T), 29 (R), 40 (M), 75 (M), 108 (K,Y), 111 (L,T), 122 (Y), 123 (Q), 125 (Q), 130 (F,H), 134 (L), 137 (H,K,S,T,W,Y), 155 (G), 156 (W), 162 (G), 163 (Y), 176 (I), 180 (K), 187 (H,S,T,W), 232 (P), 233 (D), 265 (M), and 269 (M), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPO and pNPP hydrolysis is greater than or equal to 1.1, and wherein the productive modification is selected from the group consisting of 3 (D,T), 4 (A,D,L,M), 5 (H,Y), 23 (F), 27 (E,N,Q,T), 29 (R), 33 (D,Q), 40 (M), 48 (Q), 51 (I,L,T), 56 (H,K,R,T), 58 (M,Q), 75 (R), 77 (I,T), 87 (P), 108 (K), 111 (A,L), 114 (M), 115 (R), 127 (E,F), 130 (A), 132 (Q,R), 134 (L), 137 (E,G,H,I,K,Q,R,S,Y), 155 (S), 162 (G), 163 (F,P,S,W,Y), 187 (H,N,Q,S,W), 189 (R), 225 (E), 227 (M), 232 (P), 233 (Q), and 264 (R,T), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPB, pNPO, and pNPP hydrolysis is greater than or equal to 1.1, and wherein the productive modification is selected from the group consisting of 3 (D), 4 (D,L), 5 (H), 5 (Y), 27 (Q,T), 29 (R), 40 (M), 108 (K), 111 (L), 134 (L), 137 (H,K,S,Y), 162 (G), 163 (Y), 187 (H,S,W), and 232 (P), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, the minimum performance indices (PI) relative to TLL parent for pNPB hydrolysis is less than or equal to 0.8, and wherein the minimum performance indices (PI) relative to TLL parent for pNPP hydrolysis is greater than or equal to 1, and wherein the productive modification is selected from the group consisting of 1 (Q), 9 (M), 12 (F), 15 (S), 23 (F), 27 (E), 32 (Q), 35 (E), 48 (Q), 58 (M, Q), 71 (E), 75 (R), 115 (R), 130 (A), 132 (Q, R), 137 (E, I, Q, R), 143 (A), 155 (S), 163 (F, P, S), 164 (D), 165 (I, Y), 187 (Q), 225 (E), 227 (A, M), 233 (Q), 252 (A, K,R), 264 (H, R, T), and 269 (V), wherein the amino acid positions of the lipase variant are numbered by correspondence with the amino acid sequence of *Thermomyces lanuginosus* lipase TLL set forth in SEQ ID NO:4.

Lipolytic enzymes positions of the present invention that have an amino acid modification to a parent lipolytic enzyme, wherein the modification is a modification wherein the minimum performance indices (PI) relative to TLL parent for expression and thermostability is greater than or equal to 0.8, and wherein the minimum performance indices (PI) relative to TLL parent for pNPO hydrolysis at pH 6 is greater than or equal to 1.1, and wherein the productive modification is selected from the group consisting of 1

(Q,S), 2 (L), 3 (T), 4 (A, D, L, M), 5 (H, Y), 9 (K), 11 (K), 12 (F), 15 (S), 24 (A, D, E, H, N), 27 (A, E, Q, T), 29 (R), 32 (A), 33 (D, F, Q), 38 (D), 40 (M), 48 (Q), 49 (V), 51 (I, L, M, T), 56 (H, K, T), 58 (M, Q), 69 (A), 75 (R), 77 (T), 91 (Q), 94 (R), 98 (I), 105 (A), 108 (K, Y), 111 (A, L), 114 (I, M, V), 121 (K), 123 (E, L, M, N, Q), 125 (Q), 127 (E, F), 130 (A, H), 132 (R), 134 (L), 137 (E, G, H, I, K, Q, R, S, V, Y), 143 (A), 151 (P), 154 (F, I, L), 155 (S), 156 (W), 158 (Y), 162 (G), 163 (F, P, W, Y), 164 (D, R), 165 (I, Y), 180 (K), 187 (H, N, Q, S, T, W), 189 (R), 227 (M), 228 (R), 232 (P), 252 (L), 263 (I, V), 265 (M), and 269 (M), wherein the amino acid positions of the lipase variant are numbered by correspondence with the amino acid sequence of *Thermomyces lanuginosus* lipase TLL set forth in SEQ ID NO:4.

Polypeptides of the Invention

The present invention provides novel polypeptides, which may be collectively referred to as "polypeptides of the invention." Polypeptides of the invention include isolated, recombinant, substantially pure, or non-naturally occurring variant lipolytic enzyme polypeptides, including for example, variant lipolytic enzyme polypeptides, having enzymatic activity (e.g., lipolytic activity). In some embodiments, polypeptides of the invention are useful in cleaning applications and can be incorporated into cleaning compositions that are useful in methods of cleaning an item or a surface (e.g., of surface of an item) in need of cleaning.

In some embodiments, the lipolytic enzyme variant can be a variant of a parent lipolytic enzyme from the Genus *Thermomyces*. Various lipolytic enzymes have been found in the genus *Thermomyces* that have a high identity to each other and to the lipolytic enzyme from *Thermomyces lanuginosus* (TLL) as shown in SEQ ID NO:4. All of the lipolytic enzyme variants described in the section above can be a variant of a parent lipolytic enzyme from the Genus *Thermomyces*, and more specifically a variant of the lipolytic enzyme from *Thermomyces lanuginosus* (TLL) as shown in SEQ ID NO:4.

In some embodiments, the lipolytic enzyme variant can be a variant having 50, 60, 70, 80, 90, 95, 96, 97, 98, 99 or 100% identity to a lipolytic enzyme from the genus *Thermomyces*. In various embodiments, the lipolytic enzyme variant can be a variant having 50, 60, 70, 80, 90, 95, 96, 97, 98, 99 or 100% identity to the lipolytic enzyme from *Thermomyces lanuginosus* (TLL) as shown in SEQ ID NO:4.

Described are compositions and methods relating to lipase cloned from *Thermomyces lanuginosus* (TLL). The compositions and methods are based, in part, on the observation that cloned and expressed TLL has carboxylic ester hydrolase activity (acts on carboxylic acid esters) in the presence of a detergent composition. These features of TLL makes it well suited for use in a variety of cleaning applications, where the enzyme can hydrolyze lipids in the presence of surfactants and other components found in detergent compositions.

While TLL shows activity against a variety of natural and synthetic substrates, the enzyme has shown a preference for C4-C16 substrates, with peak activity against C8 substrates. This specificity profile makes TLL well suited for hydrolysis of short, medium and long chain triglycerides and for performing transesterification reactions involving short medium and long chain fatty acids esters In one aspect, the present compositions and methods provide a variant TLL polypeptide. The parent TLL polypeptide was isolated from *Thermomyces lanuginosus* (from the family abH23.01, *Rhfaomucor mihei* lipase like (Lipase Engineering Database) with the amino acid sequence of the mature lipase set forth as PDB: 1DT3). The mature TLL polypeptide has the amino acid sequence of SEQ ID NO: 3. Similar, substantially identical TLL polypeptides may occur in nature, e.g., in other strains or isolates of T *lanuginosus*. These and other recombinant TLL polypeptides are encompassed by the present compositions and methods.

In some embodiments, the invention includes an isolated, recombinant, substantially pure, or non-naturally occurring variant lipolytic enzyme having lipolytic activity, which polypeptide comprises a polypeptide sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.5%, or 100% sequence identity to a parent lipolytic enzyme as provided herein.

In some embodiments, the variant polypeptide is a variant having a specified degree of amino acid sequence homology to the exemplified TLL polypeptide, e.g., at least 70%, at least 75%, at least 80%, at least 85%, at least 90%, at least 91%, at least 92%, at least 93%, at least 94%, at least 95%, at least 96%, at least 97%, at least 98%, or even at least 99% sequence homology to the amino acid sequence of SEQ ID NO: 3 or 4. Homology can be determined by amino acid sequence alignment, e.g., using a program such as BLAST, ALIGN, or CLUSTAL, as described herein.

Also provided is an isolated, recombinant, substantially pure, or non-naturally occurring sequence which encodes a variant lipolytic enzyme having lipolytic activity, said variant lipolytic enzyme (e.g., variant lipase) comprising an amino acid sequence which differs from the amino acid sequence of SEQ ID NO:4 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant lipase are numbered according to the numbering of corresponding amino acid positions in the amino acid sequence of *Thermomyces lanuginosus* lipase TLL shown in SEQ ID NO:4 as determined by alignment of the variant lipolytic enzyme amino acid sequence with the *Thermomyces lanuginosus* lipase TLL amino acid sequence.

As noted above, the variant lipolytic enzyme polypeptides of the invention have enzymatic activities (e.g., lipolytic activities) and thus are useful in cleaning applications, including but not limited to, methods for cleaning dishware items, tableware items, fabrics, and items having hard surfaces (e.g., the hard surface of a table, table top, wall, furniture item, floor, ceiling, etc.). Exemplary cleaning compositions comprising one or more variant lipolytic enzyme polypeptides of the invention are described infra. The enzymatic activity (e.g., lipolytic enzyme activity) of a variant lipolytic enzyme polypeptide of the invention can be determined readily using procedures well known to those of ordinary skill in the art. The Examples presented infra describe methods for evaluating the enzymatic activity, cleaning performance, detergent stability and/or thermostability. The performance of variant lipolytic enzymes of the invention in removing stains (e.g., a lipid stain), cleaning hard surfaces, or cleaning laundry, dishware or tableware item(s) can be readily determined using procedures well known in the art and/or by using procedures set forth in the Examples.

A polypeptide of the invention can be subject to various changes, such as one or more amino acid insertions, deletions, and/or substitutions, either conservative or non-conservative, including where such changes do not substantially alter the enzymatic activity of the polypeptide. Similarly, a nucleic acid of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, for example when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, and/or cleavage of or one or more truncations of one or more nucleic acids (or codons) in the sequence. Many such changes in the nucleic acid sequence may not substantially alter the enzymatic activity of the resulting encoded variant lipolytic enzyme compared to the variant lipolytic enzyme encoded by the original nucleic acid sequence. A nucleic acid of the invention can also be modified to include one or more codons that provide for optimum expression in an expression system (e.g., bacterial expression system), while, if desired, said one or more codons still encode the same amino acid(s).

In some embodiments, the present invention provides a genus of polypeptides comprising variant lipolytic enzyme polypeptides having the desired enzymatic activity (e.g., lipolytic enzyme activity or cleaning performance activity) which comprise sequences having the amino acid substitutions described herein and also which comprise one or more additional amino acid substitutions, such as conservative and non-conservative substitutions, wherein the polypeptide exhibits, maintains, or approximately maintains the desired enzymatic activity (e.g., lipolytic enzyme activity or lipase activity, as reflected in the cleaning activity or performance of the variant lipolytic enzyme). Amino acid substitutions in accordance with the invention may include, but are not limited to, one or more non-conservative substitutions and/or one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). A conservative amino acid substitution typically involves the substitution of an amino acid in an amino acid sequence with a functionally similar amino acid. For example, alanine, glycine, serine, and threonine are functionally similar and thus may serve as conservative amino acid substitutions for one another. Aspartic acid and glutamic acid may serve as conservative substitutions for one another. Asparagine and glutamine may serve as conservative substitutions for one another. Arginine, lysine, and histidine may serve as conservative substitutions for one another. Isoleucine, leucine, methionine, and valine may serve as conservative substitutions for one another. Phenylalanine, tyrosine, and tryptophan may serve as conservative substitutions for one another.

Other conservative amino acid substitution groups can be envisioned. For example, amino acids can be grouped by similar function or chemical structure or composition (e.g., acidic, basic, aliphatic, aromatic, sulfur-containing). For instance, an aliphatic grouping may comprise: Glycine (G), Alanine (A), Valine (V), Leucine (L), Isoleucine (I). Other groups containing amino acids that are considered conservative substitutions for one another include: aromatic: Phenylalanine (F), Tyrosine (Y), Tryptophan (W); sulfur-containing: Methionine (M), Cysteine (C); Basic: Arginine (R), Lysine (K), Histidine (H); Acidic: Aspartic acid (D), Glutamic acid (E); non-polar uncharged residues, Cysteine (C), Methionine (M), and Proline (P); hydrophilic uncharged residues: Serine (S), Threonine (T), Asparagine (N), and Glutamine (Q). Additional groupings of amino acids are well-known to those of skill in the art and described in various standard textbooks. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, in some embodiments, the invention provides an isolated or recombinant variant lipolytic enzyme polypeptide (e.g., variant lipase) having lipolytic activity, said variant lipolytic enzyme polypeptide comprising an amino acid sequence having at least about 90%, about 95%, about 96%, about 97%, about 98%, about 99%, or about 99.5% sequence identity to the amino acid sequence of SEQ ID NO:4. A conservative substitution of one amino acid for another in a variant lipolytic enzyme of the invention is not expected to alter significantly the enzymatic activity or cleaning performance activity of the variant lipolytic enzyme. Enzymatic activity or cleaning performance activity of the resultant lipolytic enzyme can be readily determined using the standard assays and the assays described herein.

Conservatively substituted variations of a polypeptide sequence of the invention (e.g., variant lipolytic enzymes of the invention) include substitutions of a small percentage, sometimes less than about 25%, about 20%, about 15%, about 14%, about 13%, about 12%, about 11%, about 10%, about 9%, about 8%, about 7%, or about 6% of the amino acids of the polypeptide sequence, or less than about 5%, about 4%, about 3%, about 2%, or about 1%, of the amino acids of the polypeptide sequence, with a conservatively selected amino acid of the same conservative substitution group.

Nucleic Acids of the Invention

The invention provides isolated, non-naturally occurring, or recombinant nucleic acids (also referred to herein as "polynucleotides"), which may be collectively referred to as "nucleic acids of the invention" or "polynucleotides of the invention", which encode polypeptides of the invention. Nucleic acids of the invention, including all described below, are useful in recombinant production (e.g., expression) of polypeptides of the invention, typically through expression of a plasmid expression vector comprising a sequence encoding the polypeptide of interest or fragment thereof. As discussed above, polypeptides include variant lipolytic enzyme polypeptides, including variant lipase polypeptides having enzymatic activity (e.g., lipolytic activity) which are useful in cleaning applications and cleaning compositions for cleaning an item or a surface (e.g., surface of an item) in need of cleaning.

In some embodiments, the invention provides an isolated, recombinant, substantially pure, or non-naturally occurring nucleic acid comprising a nucleotide sequence encoding any polypeptide (including any fusion protein, etc.) of the invention described above in the section entitled "Polypeptides of the Invention" and elsewhere herein. The invention also provides an isolated, recombinant, substantially pure, or non-naturally-occurring nucleic acid comprising a nucleotide sequence encoding a combination of two or more of any polypeptides of the invention described above and elsewhere herein.

Also provided is an isolated, recombinant, substantially pure, or non-naturally occurring nucleic acid comprising a polynucleotide sequence which encodes a variant lipolytic enzyme having lipolytic activity, said variant lipolytic enzyme (e.g., variant lipase) comprising an amino acid sequence which differs from the amino acid sequence of SEQ ID NO:4 by no more than 50, no more than 40, no more than 30, no more than 35, no more than 25, no more than 20, no more than 19, no more than 18, no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, or no more than 1 amino acid residue(s), wherein amino acid positions of the variant lipase are numbered according to the numbering of corresponding amino acid positions in the amino acid sequence of *Thermomyces lanuginosus* lipase TLL shown in SEQ ID NO:1 as determined by alignment of the variant lipolytic enzyme amino acid sequence with the *Thermomyces lanuginosus* lipase TLL amino acid sequence.

The present invention provides nucleic acids encoding a lipase variant of *Thermomyces* lipase, as described previously, wherein the amino acid positions of the lipase variant are numbered by correspondence with the amino acid sequence of *T. lanuginosus* lipase TLL set forth as SEQ ID NO:4.

Nucleic acids of the invention can be generated by using any suitable synthesis, manipulation, and/or isolation techniques, or combinations thereof. For example, a polynucleotide of the invention may be produced using standard nucleic acid synthesis techniques, such as solid-phase synthesis techniques that are well-known to those skilled in the art. The synthesis of the nucleic acids of the invention can be also facilitated (or alternatively accomplished) by any suitable method known in the art, including but not limited to chemical synthesis using the classical phosphoramidite method (See e.g., Beaucage et al. Tetrahedron Letters 22:1859-69 (1981)); or the method described by Matthes et al. (See, Matthes et al., EMBO J. 3:801-805 (1984), as is typically practiced in automated synthetic methods. Nucleic acids of the invention also can be produced by using an automatic DNA synthesizer. Customized nucleic acids can be ordered from a variety of commercial sources (e.g., The Midland Certified Reagent Company, the Great American Gene Company, Operon Technologies Inc., and DNA2.0). Other techniques for synthesizing nucleic acids and related principles are known in the art (See e.g., Itakura et al., Ann. Rev. Biochem. 53:323 (1984); and Itakura et al., Science 198:1056 (1984)).

Methods for Making Modified Variant Lipolytic Enzymes of the Invention

A variety of methods are known in the art that are suitable for generating modified polynucleotides of the invention that encode variant lipolytic enzymes of the invention, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches. Methods for making modified polynucleotides and proteins (e.g., variant lipolytic enzymes) include DNA shuffling methodologies, methods based on non-homologous recombination of genes, such as ITCHY (See, Ostermeier et al., 7:2139-44 (1999)), SCRACHY (See, Lutz et al. 98:11248-53 (2001)), SHIPREC (See, Sieber et al., 19:456-60 (2001)), and NRR (See, Bittker et al., 20:1024-9 (2001); Bittker et al., 101:7011-6 (2004)), and methods that rely on the use of oligonucleotides to insert random and targeted mutations, deletions and/or insertions (See, Ness et al., 20:1251-5 (2002); Coco et al., 20:1246-50 (2002); Zha et al., 4:34-9 (2003); Glaser et al., 149:3903-13 (1992)).

Vectors, Cells, and Methods for Producing Variant Lipolytic Enzymes of the Invention The present invention provides isolated or recombinant vectors comprising at least one polynucleotide of the invention described herein (e.g., a polynucleotide encoding a variant lipolytic enzyme of the invention described herein), isolated or recombinant expression vectors or expression cassettes comprising at least one nucleic acid or polynucleotide of the invention, isolated, substantially pure, or recombinant DNA constructs comprising at least one nucleic acid or polynucleotide of the invention, isolated or recombinant cells comprising at least one polynucleotide of the invention, cell cultures comprising cells comprising at least one polynucleotide of the invention, cell cultures comprising at least one nucleic acid or polynucleotide of the invention, and compositions comprising one or more such vectors, nucleic acids, expression vectors, expression cassettes, DNA constructs, cells, cell cultures, or any combination or mixtures thereof.

In some embodiments, the invention provides recombinant cells comprising at least one vector (e.g., expression vector or DNA construct) of the invention which comprises at least one nucleic acid or polynucleotide of the invention. Some such recombinant cells are transformed or transfected with such at least one vector. Such cells are typically referred to as host cells. Some such cells comprise bacterial cells, including, but are not limited to *Bacillus* sp. cells, such as *B. subtilis* cells. The invention also provides recombinant cells (e.g., recombinant host cells) comprising at least one variant lipolytic enzyme of the invention.

In some embodiments, the invention provides a vector comprising a nucleic acid or polynucleotide of the invention. In some embodiments, the vector is an expression vector or expression cassette in which a polynucleotide sequence of the invention which encodes a variant lipolytic enzyme of the invention is operably linked to one or additional nucleic acid segments required for efficient gene expression (e.g., a promoter operably linked to the polynucleotide of the invention which encodes a variant lipolytic enzyme of the invention). A vector may include a transcription terminator and/or a selection gene, such as an antibiotic resistance gene that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pXX, pC194, pJH101, pE194, pHP13 (See, Harwood and Cutting [eds.], Chapter 3, Molecular Biological Methods for *Bacillus*, John Wiley & Sons [1990]; suitable replicating plasmids for *B. subtilis* include those listed on p. 92; See also, Perego, Integrational Vectors for Genetic Manipulations in *Bacillus subtilis*, in Sonenshein et al., [eds.] *Bacillus subtilis* and Other Gram-Positive Bacteria: Biochemistry, Physiology and Molecular Genetics, American Society for Microbiology, Washington, D.C. [1993], pp. 615-624).

For expression and production of a protein of interest (e.g., variant lipolytic enzyme) in a cell, at least one expression vector comprising at least one copy of a polynucleotide encoding the modified lipolytic enzyme, and preferably comprising multiple copies, is transformed into the cell under conditions suitable for expression of the lipolytic enzyme. In some embodiments of the present invention, a polynucleotide sequence encoding the variant lipolytic enzyme (as well as other sequences included in the vector) is integrated into the genome of the host cell, while in other embodiments, a plasmid vector comprising a polynucleotide sequence encoding the variant lipolytic enzyme remains as autonomous extra-chromosomal element within the cell. The invention provides both extrachromosomal nucleic acid elements as well as incoming nucleotide sequences that are integrated into the host cell genome. The vectors described herein are useful for production of the variant lipolytic enzymes of the invention. In some embodiments, a polynucleotide construct encoding the variant lipolytic enzyme is present on an integrating vector that enables the integration and optionally the amplification of the polynucleotide encoding the variant lipolytic enzyme into the bacterial chromosome. Examples of sites for integration are well known to those skilled in the art. In some embodiments, transcription of a polynucleotide encoding a variant lipolytic enzyme of the invention is effectuated by a promoter that is the wild-type promoter for the selected precursor lipolytic enzyme. In some other embodiments, the promoter is heterologous to the precursor lipolytic enzyme, but is functional in the host cell. Specifically, examples of suitable promoters for use in bacterial host cells include, but are not limited to, for example, the amyE, amyQ, amyL, pstS, sacB, pSPAC, pAprE, pVeg, pHpall promoters, the promoter of the B. stearothermophilus maltogenic amylase gene, the B. amyloliquefaciens (BAN) amylase gene, the B. subtilis alkaline lipolytic enzyme gene, the B. clausii alkaline lipolytic enzyme gene the B. pumilis xylosidase gene, the B. thuringiensis cryIIIA, and the B. licheniformis alpha-amylase gene. Additional promoters include, but are not limited to the A4 promoter, as well as phage Lambda $P_R$ or $P_L$ promoters, and the E. coli lac, trp or tac promoters.

Variant lipolytic enzymes of the present invention can be produced in host cells of any suitable Gram-positive microorganism, including bacteria and fungi. For example, in some embodiments, the variant lipolytic enzyme is produced in host cells of fungal and/or bacterial origin. In some embodiments, the host cells are Bacillus sp., Streptomyces sp., Escherichia sp. or Aspergillus sp. In some embodiments, the variant lipolytic enzymes are produced by Bacillus sp. host cells. Examples of Bacillus sp. host cells that find use in the production of the variant lipolytic enzymes of the invention include, but are not limited to B. licheniformis, B. lentus, B. subtilis, T lanuginosus, B. lentus, B. brevis, B. stearothermophilus, B. alkalophilus, B. coagulans, B. circulars, B. pumilis, B. thuringiensis, B. clausii, and B. megaterium, as well as other organisms within the genus Bacillus. In some embodiments, B. subtilis host cells are used for production of variant lipolytic enzymes. U.S. Pat. Nos. 5,264,366 and 4,760,025 (RE 34,606) describe various Bacillus host strains that can be used for producing variant lipolytic enzymes of the invention, although other suitable strains can be used.

Several industrial bacterial strains that can be used to produce variant lipolytic enzymes of the invention include non-recombinant (i.e., wild-type) Bacillus sp. strains, as well as variants of naturally-occurring strains and/or recombinant strains. In some embodiments, the host strain is a recombinant strain, wherein a polynucleotide encoding a polypeptide of interest has been introduced into the host. In some embodiments, the host strain is a B. subtilis host strain and particularly a recombinant Bacillus subtilis host strain. Numerous B. subtilis strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; See also, U.S. Pat. Nos. 4,450,235 and 4,302,544, and EP 0134048, each of which is incorporated by reference in its entirety). The use of B. subtilis as an expression host cells is well known in the art (See e.g., Palva et al., Gene 19:81-87 [1982]; Fahnestock and Fischer, J. Bacteriol., 165:796-804 [1986]; and Wang et al., Gene 69:39-47 [1988]).

In some embodiments, the Bacillus host cell is a Bacillus sp. that includes a mutation or deletion in at least one of the following genes, degU, degS, degR and degQ. Preferably the mutation is in a degU gene, and more preferably the mutation is degU(Hy)32 (See e.g., Msadek et al., J. Bacteriol. 172:824-834 [1990]; and Olmos et al., Mol. Gen. Genet. 253:562-567 [1997]). One suitable host strain is a Bacillus subtilis carrying a degU32(Hy) mutation. In some embodiments, the Bacillus host comprises a mutation or deletion in scoC4 (See e.g., Caldwell et al., J. Bacteriol. 183:7329-7340 [2001]); spoIIE (See e.g., Arigoni et al., Mol. Microbiol. 31:1407-1415 [1999]); and/or oppA or other genes of the opp operon (See e.g., Perego et al., Mol. Microbiol. 5:173-185 [1991]). Indeed, it is contemplated that any mutation in the opp operon that causes the same phenotype as a mutation in the oppA gene will find use in some embodiments of the altered Bacillus strain of the invention. In some embodiments, these mutations occur alone, while in other embodiments, combinations of mutations are present. In some embodiments, an altered Bacillus host cell strain that can be used to produce a variant lipolytic enzyme of the invention is a Bacillus host strain that already includes a mutation in one or more of the above-mentioned genes. In addition, Bacillus sp. host cells that comprise mutation(s) and/or deletions of endogenous lipolytic enzyme genes find use. In some embodiments, the Bacillus host cell comprises a deletion of the aprE and the nprE genes. In other embodiments, the Bacillus sp. host cell comprises a deletion of 5 lipolytic enzyme genes, while in other embodiments, the Bacillus sp. host cell comprises a deletion of 9 lipolytic enzyme genes (See e.g., U.S. Pat. Appln. Pub. No. 2005/0202535, incorporated herein by reference).

Host cells are transformed with at least one nucleic acid encoding at least one variant lipolytic enzyme of the invention using any suitable method known in the art. Whether the nucleic acid is incorporated into a vector or is used without the presence of plasmid DNA, it is typically introduced into a microorganism, in some embodiments, preferably an E. coli cell or a competent Bacillus cell. Methods for introducing a nucleic acid (e.g., DNA) into Bacillus cells or E. coli cells utilizing plasmid DNA constructs or vectors and transforming such plasmid DNA constructs or vectors into such cells are well known. In some embodiments, the plasmids are subsequently isolated from E. coli cells and transformed into Bacillus cells. However, it is not essential to use intervening microorganisms such as *E. coli*, and in some embodiments, a DNA construct or vector is directly introduced into a *Bacillus* host.

Those of skill in the art are well aware of suitable methods for introducing nucleic acid or polynucleotide sequences of the invention into *Bacillus* cells (See e.g., Ferrari et al., "Genetics," in Harwood et al. [eds.], *Bacillus*, Plenum Publishing Corp. [1989], pp. 57-72; Saunders et al., J. Bacteriol. 157:718-726 [1984]; Hoch et al., J. Bacteriol. 93:1925-1937 [1967]; Mann et al., Current Microbiol. 13:131-135 [1986]; Holubova, Folia Microbiol. 30:97 [1985]; Chang et al., Mol. Gen. Genet. 168:11-115 [1979]; Vorobjeva et al., FEMS Microbiol. Lett. 7:261-263 [1980]; Smith et al., Appl. Env. Microbiol. 51:634 [1986]; Fisher et al., Arch. Microbiol. 139:213-217 [1981]; and McDonald, J. Gen. Microbiol. 130:203 [1984]). Indeed, such methods as transformation, including protoplast transformation and congression, transduction, and protoplast fusion are well known and suited for use in the present invention. Methods of transformation are used to introduce a DNA construct or vector comprising a nucleic acid encoding a variant lipolytic enzyme of the present invention into a host cell. Methods known in the art to transform *Bacillus* cells include such methods as plasmid marker rescue transformation, which involves the uptake of a donor plasmid by competent cells carrying a partially homologous resident plasmid (See, Contente et al., Plasmid 2:555-571 [1979]; Haima et al., Mol. Gen. Genet. 223:185-191 [1990]; Weinrauch et al., J. Bacteriol. 154:1077-1087 [1983]; and Weinrauch et al., J. Bacteriol. 169:1205-1211 [1987]). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding a variant lipolytic enzyme of the invention (i.e., an intermediate cell is not used to amplify, or otherwise process, the DNA construct or vector prior to introduction into the host cell). Introduction of the DNA construct or vector of the invention into the host cell includes those physical and chemical methods known in the art to introduce a nucleic acid sequence (e.g., DNA sequence) into a host cell without insertion into a plasmid or vector. Such methods include, but are not limited to calcium chloride precipitation, electroporation, naked DNA, liposomes and the like. In additional embodiments, DNA constructs or vector are co-transformed with a plasmid, without being inserted into the plasmid. In further embodiments, a selective marker is deleted from the altered *Bacillus* strain by methods known in the art (See, Stahl et al., J. Bacteriol. 158:411-418 [1984]; and Palmeros et al., Gene 247:255-264 [2000]).

In some embodiments, the transformed cells of the present invention are cultured in conventional nutrient media. The suitable specific culture conditions, such as temperature, pH and the like are known to those skilled in the art and are well described in the scientific literature. In some embodiments, the invention provides a culture (e.g., cell culture) comprising at least one variant lipolytic enzyme or at least one nucleic acid of the invention. Also provided are compositions comprising at least one nucleic acid, vector, or DNA construct of the invention.

In some embodiments, host cells transformed with at least one polynucleotide sequence encoding at least one variant lipolytic enzyme of the invention are cultured in a suitable nutrient medium under conditions permitting the expression of the present lipolytic enzyme, after which the resulting lipolytic enzyme is recovered from the culture. The medium used to culture the cells comprises any conventional medium suitable for growing the host cells, such as minimal or complex media containing appropriate supplements. Suitable media are available from commercial suppliers or may be prepared according to published recipes (See e.g., the catalogues of the American Type Culture Collection). In some embodiments, the lipolytic enzyme produced by the cells is recovered from the culture medium by conventional procedures, including, but not limited to for example, separating the host cells from the medium by centrifugation or filtration, precipitating the proteinaceous components of the supernatant or filtrate by means of a salt (e.g., ammonium sulfate), chromatographic purification (e.g., ion exchange, gel filtration, affinity, etc.). Any method suitable for recovering or purifying a variant lipolytic enzyme finds use in the present invention.

In some embodiments, a variant lipolytic enzyme produced by a recombinant host cell is secreted into the culture medium. A nucleic acid sequence that encodes a purification facilitating domain may be used to facilitate purification of soluble proteins. A vector or DNA construct comprising a polynucleotide sequence encoding a variant lipolytic enzyme may further comprise a nucleic acid sequence encoding a purification facilitating domain to facilitate purification of the variant lipolytic enzyme (See e.g., Kroll et al., DNA Cell Biol. 12:441-53 [1993]). Such purification facilitating domains include, but are not limited to, for example, metal chelating peptides such as histidine-tryptophan modules that allow purification on immobilized metals (See, Porath, Protein Expr. Purif. 3:263-281 [1992]), protein A domains that allow purification on immobilized immunoglobulin, and the domain utilized in the FLAGS extension/affinity purification system (e.g., protein A domains available from Immunex Corp., Seattle, Wash.). The inclusion of a cleavable linker sequence such as Factor XA or enterokinase (e.g., sequences available from Invitrogen, San Diego, Calif.) between the purification domain and the heterologous protein also find use to facilitate purification.

Assays for detecting and measuring the enzymatic activity of an enzyme, such as a variant lipolytic enzyme of the invention, are well known. Various assays for detecting and measuring activity of lipolytic enzymes (e.g., variant lipolytic enzymes of the invention), are also known to those of ordinary skill in the art. In particular, assays are available for measuring lipolytic enzyme activity that are based on(Add references for lipase assays) A variety of methods can be used to determine the level of production of a mature lipolytic enzyme (e.g., mature variant lipolytic enzymes of the present invention) in a host cell. Such methods include, but are not limited to, for example, methods that utilize either polyclonal or monoclonal antibodies specific for the lipolytic enzyme. Exemplary methods include, but are not limited to enzyme-linked immunosorbent assays (ELISA), radioimmunoassays (RIA), fluorescent immunoassays (FIA), and fluorescent activated cell sorting (FACS). These and other assays are well known in the art (See e.g., Maddox et al., J. Exp. Med. 158:1211 [1983]).

In some other embodiments, the invention provides methods for making or producing a mature variant lipolytic enzyme of the invention. A mature variant lipolytic enzyme does not include a signal peptide or a propeptide sequence. Some methods comprise making or producing a variant lipolytic enzyme of the invention in a recombinant bacterial host cell, such as for example, a *Bacillus* sp. cell (e.g., a *B. subtilis* cell). In some embodiments, the invention provides a method of producing a variant lipolytic enzyme of the invention, the method comprising cultivating a recombinant host cell comprising a recombinant expression vector comprising a nucleic acid encoding a variant lipolytic enzyme of the invention under conditions conducive to the production of the variant lipolytic enzyme. Some such methods further comprise recovering the variant lipolytic enzyme from the culture.

In some embodiments the invention provides methods of producing a variant lipolytic enzyme of the invention, the methods comprising: (a) introducing a recombinant expression vector comprising a nucleic acid encoding a variant lipolytic enzyme of the invention into a population of cells (e.g., bacterial cells, such as *B. subtilis* cells); and (b) culturing the cells in a culture medium under conditions conducive to produce the variant lipolytic enzyme encoded by the expression vector. Some such methods further comprise: (c) isolating the variant lipolytic enzyme from the cells or from the culture medium.

Fabric and Home Care Products

In some embodiments, the lipolytic enzyme variants of the present invention can be used in compositions comprising an adjunct material and a lipolytic enzyme variant, wherein the composition is a fabric and home care product. Examples of suitable compositions are described in Example 1.

In some embodiments, the fabric and home care product compositions comprising at least one lipolytic enzyme variant comprise one or more of the following ingredients (based on total composition weight): from about 0.0005 wt % to about 0.5 wt %, from about 0.001 wt % to about 0.1 wt %, or even from about 0.002 wt % to about 0.05 wt % of said lipolytic enzyme variant; and one or more of the following: from about 0.00003 wt % to about 0.1 wt % fabric hueing agent; from about 0.001 wt % to about 5 wt %, perfume capsules; from about 0.001 wt % to about 1 wt %, cold-water soluble brighteners; from about 0.00003 wt % to about 0.1 wt % bleach catalysts; from about 0.00003 wt % to about 0.1 wt % bacterial cleaning cellulases; and/or from about 0.05 wt % to about 20 wt % Guerbet nonionic surfactants.

As used herein, "wash performance" of a lipolytic enzyme (e.g., a variant lipolytic enzyme of the invention) refers to the contribution of the lipolytic enzyme to washing that provides additional cleaning performance to the detergent as compared to the detergent without the addition of the variant lipolytic enzyme to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

In some embodiments, the fabric and home care product composition is a granular or powder laundry detergent.

In some embodiments, the fabric and home care product composition is a liquid laundry detergent or a dish washing detergent.

It is intended that the fabric and home care product is provided in any suitable form, including a fluid or solid. The fabric and home care product can be in the form of a unit dose pouch, especially when in the form of a liquid, and typically the fabric and home care product is at least partially, or even completely, enclosed by a water-soluble pouch. In addition, in some embodiments of the fabric and home care products comprising at least one lipolytic enzyme variant, the fabric and home care product may have any combination of parameters and/or characteristics detailed above.

Cleaning Compositions

Cleaning compositions and cleaning formulations include any composition that is suited for cleaning, bleaching, disinfecting, and/or sterilizing any object, item, and/or surface. Such compositions and formulations include, but are not limited to for example, liquid and/or solid compositions, including cleaning or detergent compositions (e.g., liquid, tablet, gel, bar, granule, and/or solid laundry cleaning or detergent compositions and fine fabric detergent compositions; hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwash compositions (e.g., "hand" or "manual" dishwashing detergents) and automatic dishwashing compositions (e.g., "automatic dishwashing detergents").

Cleaning composition or cleaning formulations, as used herein, include, unless otherwise indicated, granular or powder-form all-purpose or heavy-duty washing agents, especially cleaning detergents; liquid, granular, gel, solid, tablet, or paste-form all-purpose washing agents, especially the so-called heavy-duty liquid (HDL) detergent or heavy-duty powder detergent (HDD) types; liquid fine-fabric detergents; hand or manual dishwashing agents, including those of the high-foaming type; hand or manual dishwashing, automatic dishwashing, or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

As used herein, the term "detergent composition" or "detergent formulation" is used in reference to a composition intended for use in a wash medium for the cleaning of soiled or dirty objects, including particular fabric and/or non-fabric objects or items. Such compositions of the present invention are not limited to any particular detergent composition or formulation. Indeed, in some embodiments, the detergents of the invention comprise at least one variant lipolytic enzyme of the invention and, in addition, one or more surfactants, transferase(s), hydrolytic enzymes, oxido reductases, builders (e.g., a builder salt), bleaching agents, bleach activators, bluing agents, fluorescent dyes, caking inhibitors, masking agents, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some compositions of the invention, such as, but not limited to, cleaning compositions or detergent compositions, do not contain any phosphate (e.g., phosphate salt or phosphate builder).

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

As indicated herein, in some embodiments, the cleaning compositions of the present invention further comprise adjunct materials including, but not limited to, surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant lipolytic enzymes of the present invention in the cleaning compositions, then suitable methods of keeping the cleaning adjunct materials and the lipolytic enzyme(s) separated (i.e., not in contact with each other) until combination of the two components is appropriate are used. Such separation methods include any suitable method known in the art (e.g., gelcaps, encapsulation, tablets, physical separation, etc.).

Lipase Containing Detergent Compositions

The detergent compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations and dishwashing operations.

The detergent composition according to the invention can be in liquid, paste, gels, bars or granular forms. The pH (measured in aqueous solution at use concentration) will usually be neutral or alkaline, e.g. in the range of 7-11, particularly 9-11. Granular compositions according to the present invention can also be in "compact form", i.e. they may have a relatively higher density than conventional granular detergents, i.e. from 550 to 950 g/l.

The present compositions can include one or more adjuvants (for example, surfactants that are efficient in removal of fatty acids from the fabric) and one or more lipolytic enzymes. In some embodiments, the adjuvant and lipolytic enzyme are present in a single composition. In other embodiments, the adjuvant and lipolytic enzyme are present in separate compositions that are combined before contacting an oil stain on fabric, or combined on the oil stain.

The present cleaning compositions can include one or more adjuvants (surfactants) for use in combination with a lypolytic enzyme. Suitable adjuvants can have a relatively small hydrophilic portion with no net charge and hydrophobic portion that is linear or saturated. In some embodiments, the hydrophobic portion includes at least, six, seven, eight, or nine adjacent aliphatic carbons. In some embodiments, the hydrophobic portion is cyclic. In some embodiments, the hydrophobic portion is not branched. Suitable surfactants include sugar-based compounds and zwitterionic compounds. Suitable adjuvants are disclosed, and hereby incorporated by reference in its entirety, in WO2011078949.

Sugar-based surfactants include maltopyranosides, thio-maltopyransodies, glucopyranosides, and their derivatives. Maltose-based surfactants were generally more effective than glucose-based surfactants. In some embodiments, a preferred sugar-based surfactant has a hydrophobic tail chain length of at least 4, at least 5, at least 6, and even at least 7 carbons. The tail can be aliphatic or cyclic. The tail can be unbranched, although branching is acceptable with sufficient chain length.

Particular examples of sugar-based surfactants include nonyl-β-D-maltopyranoside, decyl-β-D-maltopyranoside, undecyl-β-D-maltopyranoside, dodecyl-β-D-maltopyranoside, tridecyl-β-D-maltopyranoside, tetradecyl-β-D-maltopyranoside, hexaecyl-β-D-maltopyranoside, n-dodecyl-β-D-maltopyranoside and the like, 2,6-dimethyl-4-heptyl-β-D-maltopyranoside, 2-propyl-1-pentyl-β-D-maltopyranoside, nonyl-β-D-glucopyranoside, nonyl-β-D-glucopyranoside, decyl-β-D-glucopyranoside, dodecyl-β-D-glucopyranoside, sucrose monododecanoate, certain cyclohexylalkyl-β-D-maltosides (e.g., the CYMAL®s and CYGLAs), and the MEGA™ surfactants.

The adjuvant can be a non-sugar, non-ionic surfactant. Exemplary surfactants include Tritons with an ethoxylate repeat of nine or less. Particular Tritons are ANAPOE®-X-100 and ANAPOE®-X-114. In some embodiments, the adjuvant is a non-ionic phosphine oxide surfactant, having a hydrophobic tail of at least about 9 carbons. Exemplary surfactants include dimethyldecylphoshine oxide and dimethyldodecylphoshine oxide.

The adjuvant can be a zwitterionic surfactant, such as a FOS-choline. In some embodiments, the FOS-choline has a hydrophobic tail with a chain length of 12 or greater. The hydrophobic tail can be saturated and unsaturated and can be cyclic. Exemplary FOS-choline surfactants include FOS-CHOLINE®-12, FOS-CHOLINE®-13, FOS-CHOLINE®-14, LYSOFOS-CHOLINE®-14, FOS-CHOLINE®-15, FOS-CHOLINE®-16, FOS-MEA®-12, DODECAFOS, ISO unsat 11-10, ISO 11-6, CYOFO, NOPOL-FOS, CYCLOFOS® (CYMAL®)-5, -6. -7, -8, etc., and the like.

In some cases, the adjuvant can be a sulfobetaine zwitterionic surfactant. Preferred sulfobetaine surfactants have a hydrophobic tail having at least 12 carbons, e.g., ANZERGENT® 3-12 and ANZERGENT® 3-14. The zwitterionic oxides and CHAPS-based surfactants (e.g. CHAPS and CHAPSO) are also effective, typically at higher doses than the sulfobetaines.

In some cases, the adjuvant can be an anionic detergent, for example, a sarcosine. Preferred sarcosines have a hydrophobic tail having at least 10 carbons. In some cases, the adjuvant can also be deoxycholate.

The adjuvant can be present in a composition in an amount of at least 0.001%, at least 0.005%, at least 0.01%, at least 0.05%, at least 0.1%, or more, or at least 0.01 ppm, at least 0.05 ppm, at least 0.1 ppm, at least 0.5 ppm, at least 1 ppm, at least 5 ppm, at least 10 ppm, or more. In some cases, the adjuvant may be present in a preselected range, e.g., about 0.001-0.01%, about 0.01-0.1%, about 0.1-1%, or about 0.01-1 ppm, about 0.1-1 ppm, or about 1-10 ppm. In some cases, optimum activity is observed over a range, above and below which activity is reduced.

The surfactant system of the detergent can comprise nonionic, anionic, cationic, ampholytic, and/or zwitterionic surfactants. The surfactant is typically present at a level from 0.1% to 60% by weight, e.g. 1% to 40%, particularly 10-40% preferably from about 3% to about 20% by weight. The detergent will usually contain 0-50% of anionic surfactant such as linear alkylbenzenesulfonate (LAS), alpha-olefin sulfonate (AOS), alkyl sulfate (fatty alcohol sulfate) (AS), alcohol ethoxysulfate (AEOS or AES), secondary alkane sulfonates (SAS), alpha-sulfo fatty acid methyl esters, alkyl- or alkenylsuccinic acid or soap.

The detergent can comprise 0-40% of nonionic surfactant polyalkylene oxide (e.g. polyethylene oxide) condensates of alkyl phenols. Preferred nonionic surfactants are alcohol ethoxylate (AEO or AE), carboxylated alcohol ethoxylates, nonylphenol ethoxylate, alkylpolyglycoside, alkyldimethyl-amineoxide, ethoxylated fatty acid monoethanolamide, fatty acid monoethanolamide, alkyl(N-methyl)-glucoseamide or polyhydroxy alkyl fatty acid amide (e.g. as described in WO 92106154).

Semi-polar nonionic surfactants are another category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety from about 10 no to about 18 carbon atoms and a moiety selected from the group consisting of alkyl and hydroxyalkyl moieties of from about 1 to about 3 carbon atoms. The amine oxide surfactants in particular include $C_{10}$-$C_{18}$ alkyl dimethyl amine oxides and $C_8$-$C_{12}$ alkoxy ethyl dihydroxy ethyl amine oxides.

The detergent composition can further comprise cationic surfactants. Cationic detersive surfactants used are those having one long-chain hydrocarbyl group. Examples of such cationic surfactants include the ammonium surfactants such as alkyl trimethyl ammonium halogenides. Highly preferred cationic surfactants are the water soluble quaternary ammonium compounds. Examples of suitable quaternary ammonium compounds include coconut trimethyl ammonium chloride or bromide; coconut methyl dihydroxy ethyl ammonium chloride or bromide; decyl triethyl ammonium chloride; decyl dimethyl hydroxyl ethyl ammonium chloride or bromide; C12-15 dimethyl hydroxyl ethyl ammonium chloride or bromide; coconut dimethyl hydroxyl ethyl ammonium chloride or bromide; myristyl trimethyl ammonium methyl sulphate; lauryl dimethyl benzyl ammonium chloride or bromide; lauryl dimethyl (ethenoxy)$_4$ ammonium chloride or bromide; choline esters, dialkyl imidazolines.

The detergent composition can further comprise ampholytic surfactants. These surfactants can be broadly described as aliphatic derivatives of secondary or tertiary amines, or aliphatic derivatives of heterocyclic secondary and tertiary amines in which the aliphatic radical can be straight-, or branched-chain. One of the aliphatic substituent contains at least about 8 carbon atoms, typically from about 8 to about 18 carbon atoms, and at least one contains an anionic water-solubilizing group, e.g. carboxy, sulfonate, sulfate. Examples of compounds falling within this definition are sodium 3-(dodecylamino) propionate, sodium 3-(dodecylamino)-propane-1-sulfonate, sodium 2-(dodecylamino) ethyl sulfate, sodium 2-(dimethylamino)octadecanoate, di-sodium 3-(N-carboxymethyldodecylamino)propane-1-sulfonate, disodium octadecyl-iminodiacetate, sodium 1-carboxymethyl-2-undecylimidazole, and sodium N,N-bis (2-hydroxyethyl)-2-sulfato-3-dodecoxy-propylamine. Sodium 3-(dodecylamino)propane-1-sulfonate is preferred.

Zwitterionic surfactants are also used in detergent compositions especially within laundry. These surfactants can be broadly described as derivatives of secondary and tertiary amines, derivatives of heterocyclic secondary and tertiary amines, or derivatives of quaternary ammonium, quaternary phosphonium or tertiary sulfonium compounds. The cationic atom in the quaternary compound can be part of a heterocyclic ring. In all of these compounds, there is at least one aliphatic group, straight chain or branched, containing from about 3 to 18 carbon atoms and at least one aliphatic substituent containing an anionic water solubilizing group, e.g. carboxy, sulfonate, sulfate, phosphate or phosphonate. Ethoxylated zwitterionic compounds in combination with zwitterionic surfactants have been particularly used for clay soil removal in laundry applications.

The detergent may contain 1-65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt i.e. essentially free of detergent builder.

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water soluble alkali metal carbonates, borates and silicates as well as layered disilicates and the various types of water insoluble crystalline or amorphous alumino silicates of which zeolites is the best known representative. Examples of suitable organic builders include alkali metal, ammonium or substituted ammonium salts of succinates, malonates, fatty acid malonates, fatty acid sulphonates, carboxymethoxy succinates, poly acetates, carboxylates, polycarboxylates, aminopolycarboxylates and polyacetyl carboxylates.

A suitable chelant for inclusion in the detergent compositions is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include Na2EDDS and Na4EDDS. Examples of such preferred magnesium salts of EDDS include MgEDDS and Mg2EDDS. The magnesium salts are the most preferred for inclusion in compositions.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent composition may contain bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate. The bleaching system may also comprise a hydrogen peroxide source such as perborate or percarbonate which may be combined with a peracid-forming bleach activator such as tetraacetyl-ethylenediamine (TAED) or nonanoyloxybenzenesulfonate (NOBS). Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are tetraacetylethylenediamine (TAED), nonanoyloxybenzenesulfonate (NOBS), 3,5-trimethyl-hexsanoloxybenzenesulfonate (ISONOBS) or pentaacetylglucose (PAG).

The lipase of the invention, or optionally another enzyme incorporated in the detergent composition, is normally incorporated in the detergent composition at a level from 0.00001% to 3% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition. The amount of lipase protein may be 0.001-30 mg per gram of detergent or 0.001-100 mg per liter of wash liquor. The lipase variants of the invention are particularly suited for detergents comprising of a combination of anionic and nonionic surfactant with 70-100% by weight of anionic surfactant and 0-30% by weight of nonionic, particularly 80-100% of anionic surfactant, and 0-20% nonionic surfactant. As further described, some preferred lipases of the invention are also suited for detergents comprising 40-70% anionic and 30-60% non-ionic surfactant. The detergent composition may, in addition to the lipase of the invention, comprise other enzyme(s) providing cleaning performance and/or fabric care benefits, e.g. proteases, additional lipases, cutinases, amylases, cellulases, peroxidases, oxidases (e.g. laccases), mannanases, oxidoreductases, and/or pectate lyases.

The enzymes of the detergent composition may be stabilized using conventional stabilizing agents (e.g. a polyol such as propylene glycol or glycerol, a sugar or sugar alcohol, lactic acid, boric acid, or a boric acid derivative as e.g. an aromatic borate ester). Boronic acid or borinic acid derivatives as enzyme stabilizers include Boric acid, Thiophene-3-boronic acid, Thiophene-2-boronic acid, 4-Methylthiophene-2-boronic acid, 5-Ethylthiophene-2-boronic acid, 5-Methylthiophene-2-boronic acid, 5-Bromothiophene-2-boronic acid, 5-Chlorothiophene-2-boronic acid, Dibenzothiophene-1-boronic acid, Dibenzofuran-1-boronic acid, Dibenzofnran-4-boronic acid, Picoline-2-boronic acid, Diphenylborinic acid (ethanolamine complex), 5-Methoxythio-phene-2-boronic acid, Thionaphthrene-1-boronic acid, Furan-2-boronic acid, Furan-3-boronic acid, 2,5-dimethylthiophene-3-boronic acid, Benzofuran-1-boronic acid, 3-Methoxythio-phene-2-boronic acid, 5-n-Propyl-thiophene-2-boronic acid, 5-Methoxyfuran-2-boronic acid, 3-Bromothiophene-2-boronic acid, 5-Ethylfuran-2-boronic acid, 4-Carbazole ethyl boronic acid.

An optional ingredient is a suds suppressor (e.g. exemplified by silicones-alkylated polysiloxane materials, and silica-silicone mixtures, where the silica is in the form of silica aerogels and xerogels and hydrophobic silicas of various types. The suds suppressor can be incorporated as particulates, in which the suds suppressor is advantageously releasable incorporated in a water-soluble or water dispersible, substantially non surface-active detergent impermeable carrier. Alternatively the suds suppressor can be dissolved or dispersed in a liquid carrier and applied by spraying on to one or more of the other components.

The detergent may also contain inorganic or organic softening agents. Inorganic softening agents are exemplified by the smectite clays (5% to 15%). Organic fabric softening agents (0.5% to 5%) include the water insoluble tertiary amines and their combination with mono $C_{12}$-$C_{14}$ quaternary ammonium salts and di-long-chain amides, or high molecular weight polyethylene oxide materials.

The detergent may also contain other conventional detergent ingredients such as, e.g., fabric conditioners including clays, deflocculant material, foam boosters/foam depressors (in dishwashing detergents foam depressors), anti-corrosion agents, soil-suspending or dispersing agents (0 to 10%), anti-soil-redeposition agents, dyes, dehydrating agents, bactericides, optical brighteners, abrasives, tarnish inhibitors, coloring agents, and/or encapsulated or non-encapsulated perfumes.

| Liquid detergent formulation | |
|---|---|
| Nonionic (Neodol 25-7) AE | 25% |
| Anionic (Vista C-S50) LAS | 5% |
| Triethanolamine | 5% |
| Ethanol | 10% |
| Stabilizer | 0.5, 2.5, 5% |
| Protease | 1% |
| Amylase | 0.3% |
| Water | up to 100% |
| Adjust to pH = 9.0 | |
| Lipase insert after amylase | 0.001-1% |

| | Detergent formulations | | | | | |
|---|---|---|---|---|---|---|
| | I | II | III | IV | | |
| | (%) | (%) | (%) | (%) | V | VI |
| | pow- | pow- | pow- | pow- | (%) | (%) |
| Ingredients | der | der | der | der | liquid | liquid |
| Linear alkylbenzenesulfonate (calculated as acid) or slkyl sulfate, alpha olefin sulfonate, alpha-sulfo fatty acid methyl esters, alkanesulfonates, soap | 7-12 | 6-11 | 5-9 | 8-12 | 15-21 | 15-21 |
| Alcohol ethoxysulfate (e.g. $C_{12-18}$ alcohol 1-2 EO) or alkyl sulfate (e.g. $C_{16-18}$) | 1-4 | 1-3 | — | | | |
| soap as fatty acid (e.g. $C_{16-22}$ or oleic acid) | — | — | 1-3 | | 3-13 | 3-10 |
| Alcohol ethoxylate (e.g. $C_{14-15}$ or $C_{12-15}$ 7EO or 5EO) | 5-9 | 5-9 | 7-14 | 10-25 | 12-18 | 3-9 |
| Alkenylsuccinic acid ($C_{12-14}$) | | | | | 0-13 | |
| Aminoethanol | | | | | | 8-18 |
| sodium carbonate ($Na_2CO_3$) | 14-20 | 15-21 | 10-17 | 14-22 | | |
| soluble silicate (as $Na_2O$, $2SiO_2$) | 2-6 | 1-4 | 3-9 | 1-5 | | |
| zeolite (as $NaAlSiO_4$) | 15-22 | 24-34 | 23-33 | 25-35 | | 14-22 |
| sodium sulfate (as $Na_2SO_4$) | 0-6 | 4-10 | 0-4 | 0-10 | | |

| Detergent formulations | | | | | | |
|---|---|---|---|---|---|---|
| Ingredients | I (%) powder | II (%) powder | III (%) powder | IV (%) powder | V (%) liquid | VI (%) liquid |
| sodium citrate/citric acid ($C_6H_5Na_3O_7/C_6H_8O_7$) or potassium citrate | 0-15 | 0-15 | — | | 2-8 | 9-18 |
| sodium perborate (as $NaBO_3.H_2O$) or borate (as $B_4O_7$) | 11-18 | — | 8-16 | | 0-2 | 0-2 |
| TAED | 2-6 | — | 2-8 | | | |
| Phosphonate (e.g. EDTMPA) | — | — | 0-1 | | 0-3 | |
| Ethanol | | | | | 0-3 | |
| carboxymethylcellulose | 0-2 | 0-2 | 0-2 | 0-2 | | 0-2 |
| Polymers (PEG, PVP) | | | | | 0-3 | 0-3 |
| Anchoring polymers (e.g. maleic/acrylic acid copolymer PVP, PEG) | 0-3 | 1-6 | 1-3 | 1-3 | | 0-3 |
| Propylene glycol | | | | | 8-14 | |
| Glycerol | | | | | | 0-5 |
| Enzymes (alkaline lipases) | 0-5 | 0-5 | 0-5 | 0-5 | 0-5 | 0-5 |
| minor ingredients (e.g. suds, supressors, perfume, optical brightener, photobleach) | 0-5 | 0-5 | 0-5 | 0-5 | 0-5 | 0-5 |

| Detergent formulations | | | | | | |
|---|---|---|---|---|---|---|
| Ingredients | VII (%) powder | VIII (%) powder | IX (%) powder | X (%) liquid | XI (%) liquid | XII (%) powder |
| Linear alkylbenzenesulfonate (calculated as acid) or slkyl sulfate, alpha olefin sulfonate, alpha-sulfo fatty acid methyl esters, alkanesulfonates, soap | 8-14 | 6-12 | | 15-23 | 20-32 | 25-40 |
| Fatty alcohol sulfate | 5-10 | | | | | |
| Ethoxylated fatty acid monoethanolamide | 3-9 | 5-11 | | | | |
| Alcohol ethoxy sulfate (e.g. $C_{12-18}$ alcohol 1-2 EO, or $C_{12-15}$ 2-3 EO) or alkyl sulfate (e.g. $C_{16-18}$) | | | | 8-15 | | |
| soap as fatty acid (e.g. $C_{16-22}$ or oleic acid or lauric acid) | 0-3 | 0-3 | | 2-6 | 0-3 | |
| Alcohol ethoxylate (e.g. $C_{14-15}$ or $C_{12-15}$ 7EO or 5EO) | | | 1-4 | 3-9 | 6-12 | 1-10 |
| Alkenylsuccinic acid ($C_{12-14}$) Aminoethanol | | | | 1-5 | 2-6 | |
| sodium carbonate ($Na_2CO_3$) | 5-10 | 4-10 | 14-22 | | | 8-25 |
| soluble silicate (as $Na_2O$, $2SiO_2$) | 1-4 | 1-4 | | | | 5-15 |
| zeolite (as $NaAlSiO_4$) | 20-40 | 30-50 | 18-32 | | | 15-28 |
| sodium sulfate (as $Na_2SO_4$) | 2-8 | 3-11 | 5-20 | | | 0-5 |
| sodium citrate/citric acid ($C_6H_5Na_3O_7/C_6H_8O_7$) or potassium citrate | | 5-12 | 3-8 | 5-10 | 8-14 | |
| Hydrotrope (eg sodium toluenesulfonate) | | | | 2-6 | | |
| sodium perborate (as $NaBO_3$, $H_2O$, or $NaBO_3$, $4H_2O$) or borate (as $B_4O_7$) | 12-18 | | 4-9 | 0-2 | 1-3 | 0-20 |
| TAED (or NOBS) | 2-7 | | 1-5 | | | 0-5 |
| Phosphonate (e.g. EDTMPA) | | | | | | |
| Ethanol | | | | 1-3 | | |
| carboxymethylcellulose | | | 0-2 | 0-1 | | |
| Polymers (PEG, PVP) | | | | | | |
| Anchoring polymers (e.g. maleic/acrylic acid copolymer PVP, PEG) | 1-5 | 1-5 | 1-5 | | 0-3 | |
| Propylene glycol | | | | 2-5 | | |
| Glycerol | | | | | 3-8 | |
| Enzymes (alkaline lipases) | 0-5 | 0-5 | 0-5 | 0-5 | 0-5 | 0-5 |
| minor ingredients (e.g. suds, supressors, perfume, optical brightener, photobleach) | 0-5 | 0-5 | 0-5 | 0-5 | 0-5 | 0-3 |

Anionic Model Detergent A

A model granular detergent (90% anionic out of total surfactants, pH in solution 10.2) is made by mixing the following ingredients (% by weight):

8.7% anionic surfactant: LAS ($C_{10}$-$C_{13}$)
    7.4% anionic surfactant: AS ($C_{12}$)
    1.8% Nonionic surfactant: alcohol ethoxylate ($C_{12}$-$C_{15}$ 7EO)
    30% Zeolite P (Wessalite P)
    18% Sodium Carbonate
    5% Sodium Citrate
    17% Sodium sulfate
    0.3% Carboxy-Methyl-Cellulose
    6.5% Sodium-percarbonate monohydrate
    2.1% NOBS Anionic Model Detergent B A second model granular detergent (79% anionic out of total surfactants, pH in solution 10.2) is made by mixing the following ingredients (% by weight):

27% anionic surfactant: AS ($C_{12}$)
    7% Nonionic surfactant ($C_{12-15}$, 7EO)
    60% Zeolite P (Wessalite P)
    5% Sodium Carbonate
    0.6% Sokalan CP5
    1.5% Carboxy-Methyl-Cellulose Anionic/Non-Ionic Model Detergent A model detergent solution (32% anionic out of total surfactant, pH 10.2) is made by adding the following ingredients to 3.2 mM Ca2+/Mg2+(5:1) in pure water:

0.300 g/l of alkyl sulphate (AS; $C_{14-16}$);
    0.650 g/l of alcohol ethoxylate (AEO; $C_{12-14}$, 6EO);
    1.750 g/l of Zeolite P
    0.145 g/l of $Na_2CO_3$
    0.020 g/l of Sokalan CP5
    0.050 g/l of CMC (carboxy-methyl cellulose)

Low Detergent Compositions

European laundry powder detergent

15% of surfactant of which 6% was LAS, 3% was AES and 6% was non ionic surfactants. It further contained 47% builder comprising fatty acid, zeolite A, carbonate and silicate.

15% of surfactant of which 3% was AES, 6% was LAS and 6% was non ionic surfactants. It further comprised 47% builder comprising fatty acid, zeolite A, carbonate, silicate, and it comprised 5% polycarboxylate polymers.

15% of surfactant of which 3% was AES, 6% was LAS and 6% was non ionic surfactants. It further contained 47% builder comprising fatty acid, zeolite A, carbonate, silicate, and it comprised 5% polycarboxylate polymers.

15% of surfactant of which 6% was LAS, 3% was AES and 6% was nonionic surfactants. It further contained 47% builder consisting of fatty acid, zeolite A, carbonate & silicate, 5% polycarboxylate dispersing polymers, 15% sodium perborate, and 4% tetraacetyl-ethylene-diamine (TAEO).

15% of surfactant of which 6% was LAS, 3% was AES and 6% was non ionic surfactants. It further contained 47% builder consisting of fatty acid, 22% zeolite A, carbonate and silicate, and 5% polycarboxylate dispersing polymers.

15% of surfactant of which 6% was LAS, 3% was AES and 6% was non ionic surfactants. It further contained 47% builder consisting of fatty acid, 22% zeolite A, carbonate and silicate, and 5% polycarboxylate dispersing polymers 15% of surfactant of which 6% was LAS, 3% was AES and 6% was nonionic surfactants. It further contained 47% builder consisting of fatty acid, 22% zeolite A, carbonate and silicate, and 5% polycarboxylate dispersing polymers.

21% of surfactant of which 8.1% was LAS, 6.5% was AS, 4.0% was non ionic surfactants, and 2.5% was cationic surfactants (DSDMAC). It further contained 64% builder consisting of fatty acid, carbonate, zeolite A, silicates, and citrate, and also contained 2.7% of dispersing polymers.

16.9% surfactants including soap of which 11% was LAS and 5.9% non-ionic and 4.1% soap, and 63% builders.
European Liquid Laundry Detergent 27% of surfactant of which 16.9% was AS, 6.7% was nonionic surfactants, and 3.5% was cationic surfactants (DSDMAC). It further contained 18.7% builder consisting of fatty acid, carbonate, citrate, and boric acid.
North American Laundry Liquid Detergent 23% of surfactant of which 16% was AES, 5% was LAS and 2% was non ionic surfactants. It further contained 6% builder comprising soap, citric acid, DTPA and calcium formate Reducing the level of surfactant in the detergent composition to 50% of normal level, and replacing it with 0.1% Lipase protein gave better performance 23% of surfactant of which 16% was AES, 5% was LAS and 2% was non ionic surfactants. It further contained 6% builder consisting of soap, citric acid, DTPA and calcium formate, and 5% poly-carboxylate dispersing polymers.
North American Laundry Powder detergent 16.3% of surfactant of which 7.8% was LAS, 6.7% was AS and 1.8% was nonionic surfactants, and 60% builder comprising fatty acid, zeolite A, carbonate and silicate.

14.9% of surfactant of which 11.5% was LAS and 3.4% was non ionic surfactants, and 55% builder comprising fatty acid, zeolite A, carbonate and silicate.

19.5% of surfactant of which 4.5% was LAS, 13% was AS and 2% was non ionic surfactants, and 61% builder comprising fatty acid, zeolite A, carbonate and silicate.
Japanese Laundry Powder Detergent 24.3% of surfactant of which 11.1% was LAS, 11.6% was ester sulfonate and 1.6% was nonionic surfactants, and 60% builder comprising fatty acid, zeolite A, carbonate and silicate.

27.9% of surfactant of which 15 27.5% was LAS and 0.4% was nonionic surfactants, and 64% builder comprising zeolite A, carbonate, citrate, phosphates and silicate.
European Color Compact Laundry Powder 21.1% of a surfactant system, of which 8.1% was LAS, 6.5% was AS, 2.5% was Arguat 2T-70, and 4% was non-ionic surfactants, and 64% builder comprising fatty acid, zeolite A, carbonate, citric acid and silicate. The surfactant system was prepared separately from the builder. The surfactant system was prepared either Neodo125-7 or Lutensol ON60 as nonionic surfactant.

| Detergent composition | | | | |
|---|---|---|---|---|
| Ingredients Material | Ex. 1 Level (parts as is) | Ex. 2 Level (parts as is) | Ex. 3 Level (parts as is) | Ex. 4 Level (parts as is) |
| Glycerol | 3.17 | 3.17 | 3.17 | 3.17 |
| MPG | 5.7 | 5.7 | 5.7 | 5.7 |
| NaOH | 2.13 | 2.13 | 2.13 | 2.13 |
| TEA | 2.05 | 2.05 | 2.05 | 2.05 |
| Neodol 25-7 | 12.74 | 12.74 | 12.74 | 12.74 |
| F-Dye | 0.18 | 0.18 | 0.18 | 0.18 |
| Citric Acid | 1.71 | 1.71 | 1.71 | 1.71 |
| LAS (as LAS Acid) | 8.49 | 8.49 | 8.49 | 8.49 |
| Fatty acid | 3.03 | 3.03 | 3.03 | 3.03 |
| Empigen BB | 1.5 | 1.5 | 1.5 | 1.5 |
| SLES | 4.24 | 4.24 | 4.24 | 4.24 |
| Dequest 2066 | 0.875 | 0.875 | 0.875 | 0.875 |
| Patent Blue | 0.00036 | 0.00036 | 0.00036 | 0.00036 |
| Acid Yellow | 0.00005 | 0.00005 | 0.00005 | 0.00005 |
| Opacifier | 0.0512 | 0.0512 | 0.0512 | 0.0512 |
| Perfume | 0.734 | 0.734 | 0.734 | 0.734 |
| Borax | 10 | 10 | 10 | 10 |
| Savinase | 2.362 | 2.362 | 2.362 | 2.362 |
| Stainzyme | 0.945 | 0.945 | 0.945 | 0.945 |
| Soap | 3.03 | 3.03 | 3.03 | 3.03 |
| EPEI 20E0 (ex Nippon Shokubai) polyethyleneimine having a weight average molecular weight of about 600, and wherein the polyethyleneimine has been modified by alkoxylation with an average 20 ethylene oxide moieties | 5.5 | 5.5 | 5.5 | 9 |
| LIPASE | 3 | 3 | 3 | 3 |
| Texcare SRN170 (ex Clariant) soil release polymer | 0 | 7.5 | 0 | 0 |
| Sokolan CP5 (ex BASF) Soil-release polymer | 0 | 0 | 20 | 0 |

| Enzymatic detergent and bleaching composition | |
|---|---|
| Ingredients | % by weight |
| Sodium dodecyl benzene sulphonate | 6.5 |
| C14-C15 primary alcohol, condensed with 11 moles of ethylene oxide | 2 |
| Sodium stearate | 1 |
| Sodium silicate | 7 |
| Sodium carboxymethyl cellulose | 0.5 |
| $Na_2SO_4$ | 37 |
| Pentasodium triphosphate | 15 |
| Trisodium orthophosphate | 5 |
| Fluorescer | 0.2 |
| Ethylene diamine tetraacetic acid | 0.5 |
| Water | 6.2 |
| Dyes | 0.01 |
| Lipase | 0.001-1 |
| bleach systems | sodium perborate + SNOBS, sodium perborate + TAED, DPDA, MPS All generating 1.5 mmol peracid in solution |

| Enzymatic detergent and bleaching composition | |
| --- | --- |
| Ingredients | % by weight |
| Sodium dodecyl benzene sulphonate | 8.5 |
| C14-C15 primary alcohol, condensed with 11 moles of ethylene oxide | 4 |
| sodium hardened rapeseed oil soap | 1.5 |
| sodium triphosphate | 33 |
| sodium carbonate | 5 |
| sodium silicate | 6 |
| sodium sulphate | 20 |
| water | 9 |
| fluorescers, soil-suspending agents, dyes, perfumes | minor amount |
| anti-foam granules | 1.2 |
| Dequest R 2047 (34% pure) | 0.3 |
| Lipase | 0.001-1 |

| Detergent compositions | | |
| --- | --- | --- |
| Ingredients | % wt | % wt |
| sodium alkylbenzenesulphonate | 24 | 28 |
| pentasodium tripolyphosphate | 15 | 2.1 |
| alkaline sodium silicate sodium | 10 | 12 |
| carboxymethylcellulose sodium | 0.6 | 0.6 |
| sulphate | 32.5 | 15.4 |
| fluorescer | 0.4 | 0.4 |
| sodium carbonate | 10 | 35 |
| miscellaneous + water | to 100% | to 100% |
| Lipase | 0.001-1 | 0.001-1 |

| Enzymatic Detergent composition | |
| --- | --- |
| Ingredients | % by weight |
| sodium linear dodecylbenzenesulphonate | 13.35 |
| sodium $C_{12}$-$C_{13}$ alcohol (6.5 EO) sulphate | 6.67 |
| sodium carbonate | 54.2 |
| sodium tripolyphosphate | 9.01 |
| sodium silicate | 4.6 |
| sodium hydroxide | 1.66 |
| sodium carboxymethylcellulose | 0.5 |
| Dequest 2006 | 1.9 |
| perfume, dye, water | q.s. |
| Lipase | 0.001-1 |
| Protease (Alcalase) | 20 GU/mL |

| Liquid laundry detergent formulation | |
| --- | --- |
| Ingredients | Parts by weight |
| Sodium dodecyl benzene sulphonate | 8.5 |
| C12-C15 primary alcohol, condensed with 7 moles of ethylene oxide | 4 |
| Sodium-hardened rapeseed oil soap | 1.5 |
| Sodium triphosphate | 33 |
| Sodium carbonate | 5 |
| Sodium silicate | 6 |
| Sodium sulphate | 20 |
| Water | 9 |
| Fluorescers, soil-suspending agents, dyes, perfumes | minor amount |
| Sodium perborate | 12 |
| Tetraacetyl ethylene diamine (TAED) (granules) | 2 |
| Proteolytic enzyme (Savinase ex NOVO) | 0.4 |
| Lipase | 0.001-1 |
| Protease (Alcalase) | 20 GU/mL |

| Liquid detergent compositions | | | | |
| --- | --- | --- | --- | --- |
| | A | B | C | D |
| sodium dodecylbenzene sulphonate | 9 | 9 | 9 | 9 |
| C13-C15 linear primary alcohol, condensed with 7 moles of ethylene oxide (e.g. Synperonic A7) | 1 | 4 | 4 | 1 |
| C13-C15 linear primary alcohol, condensed with 3 moles of ethylene oxide (e.g. Synperonic A3) | 3 | 0 | 0 | 3 |
| sodium tripolyphosphate | 23 | 23 | 0 | 0 |
| zeolite type 4A | 0 | 0 | 24 | 24 |
| copolymer of acrylic acid with maleic anhydride | 0 | 0 | 4 | 4 |
| sodium polyacrylate | 2 | 2 | 0 | 0 |
| alkaline silicate | 5 | 5 | | |
| fluorescer | 0.25 | 0.25 | 0.16 | 0.16 |
| EDTA | 0.15 | 0.15 | 0.18 | 0.18 |
| SCMC | 0.5 | 0.5 | 0.55 | 0.55 |
| salt | 2 | 2 | 0 | 0 |
| sodium sulphate | 26.8 | 26.8 | 22.31 | 22.31 |
| sodium carbonate | 0 | 0 | 10.3 | 10.3 |
| moisture | 10 | 10 | 11 | 11 |
| TAED | 3 | 3 | 3.3 | 3.3 |
| sodium perborate monohydrate | 10 | 10 | 8 | 8 |
| calcium Dequest ®$^{2047}$ | 0.7 | 0.7 | 0.3 | 0.3 |
| foam depressor | 3 | 3 | 2.5 | 2.5 |
| perfume | 0.2 | 0.2 | 0 | 0 |
| alkaline protease (Savinase (A) 6T) | 0.4 | 0.4 | 0.4 | 0.4 |
| Lipase | 0.001-1 | | | |

| Dishwashing composition | |
| --- | --- |
| Ingredients | % by weight |
| sodium tripolyphosphate | 24 |
| soda ash | 20 |
| sodium disilicate | 11 |
| linear C10 alcohol, condensed with 6 moles of ethylene oxide and 24 moles of propylene oxide | 2.5 |
| sodium sulphate | 44 |
| water | to 100 |
| Lipase | 0.001-1 |

The cleaning compositions of the present invention are advantageously employed for example, in laundry applications, hard surface cleaning, dishwashing applications, as well as cosmetic applications such as dentures, teeth, hair and skin. In addition, due to the unique advantages of increased effectiveness in lower temperature solutions, the enzymes of the present invention are ideally suited for laundry applications. Furthermore, the enzymes of the present invention find use in granular and liquid compositions.

The variant lipolytic enzymes of the present invention also find use in cleaning additive products. In some embodiments, low temperature solution cleaning applications find use. In some embodiments, the present invention provides cleaning additive products including at least one enzyme of the present invention is ideally suited for inclusion in a wash process when additional bleaching effectiveness is desired. Such instances include, but are not limited to low temperature solution cleaning applications. In some embodiments, the additive product is in its simplest form, one or more lipolytic enzymes. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present invention, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to, various salts of sulfate, carbonate and silicate as well as talc, clay and the like. Suitable filler or carrier materials for liquid compositions include, but are not limited to water or low molecular weight primary and secondary alcohols including polyols and diols. Examples of such alcohols include, but are not limited to, methanol, ethanol, propanol and isopropanol. In some embodiments, the compositions contain from about 5% to about 90% of such materials. Acidic fillers find use to reduce pH. Alternatively, in some embodiments, the cleaning additive includes adjunct ingredients, as more fully described below.

The present cleaning compositions and cleaning additives require an effective amount of at least one of the lipolytic enzyme variants provided herein, alone or in combination with other lipolytic enzymes and/or additional enzymes. The required level of enzyme is achieved by the addition of one or more lipolytic enzyme variants of the present invention. Typically the present cleaning compositions comprise at least about 0.0001 weight percent, from about 0.0001 to about 10, from about 0.001 to about 1, or even from about 0.01 to about 0.1 weight percent of at least one of the variant lipolytic enzymes of the present invention.

The cleaning compositions herein are typically formulated such that, during use in aqueous cleaning operations, the wash water will have a pH of from about 5.0 to about 11.5, or about 6.0 to 8.0 or even from about 7.5 to about 10.5. Liquid product formulations are typically formulated to have a neat pH from about 3.0 to about 9.0 or even from about 3 to about 8. Granular laundry products are typically formulated to have a pH from about 6 to about 11, or even from about 8 to about 10. Techniques for controlling pH at recommended usage levels include the use of buffers, alkalis, acids, etc., and are well known to those skilled in the art.

Suitable "low pH cleaning compositions" typically have a neat pH of from about 3 to about 8, and are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine or hydrochloric acid, to provide such cleaning composition with a neat pH of from about 3 to about 8. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the variant lipolytic enzyme(s) is/are employed in a granular composition or liquid, it is desirable for the variant lipolytic enzyme to be in the form of an encapsulated particle to protect the variant lipolytic enzyme from other components of the granular composition during storage. In addition, encapsulation is also a means of controlling the availability of the variant lipolytic enzyme during the cleaning process. In some embodiments, encapsulation enhances the performance of the variant lipolytic enzyme(s) and/or additional enzymes. In this regard, the variant lipolytic enzymes of the present invention are encapsulated with any suitable encapsulating material known in the art. In some embodiments, the encapsulating material typically encapsulates at least part of the catalyst for the variant lipolytic enzyme(s) of the present invention. Typically, the encapsulating material is water-soluble and/or water-dispersible. In some embodiments, the encapsulating material has a glass transition temperature (Tg) of 0° C. or higher. Glass transition temperature is described in more detail in WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See e.g., EP 0 922 499; U.S. Pat. Nos. 4,977,252; 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

As described herein, the variant lipolytic enzymes of the present invention find particular use in the cleaning industry, including, but not limited to laundry and dish detergents. These applications place enzymes under various environmental stresses. The variant lipolytic enzymes of the present invention provide advantages over many currently used enzymes, due to their stability under various conditions.

Indeed, there are a variety of wash conditions including varying detergent formulations, wash water volumes, wash water temperatures, and lengths of wash time, to which lipolytic enzymes involved in washing are exposed. In addition, detergent formulations used in different geographical areas have different concentrations of their relevant components present in the wash water. For example, European detergents typically have about 2000-10000 ppm of detergent components in the wash water, while Asian detergents typically have approximately 300-2500 ppm of detergent components in the wash water. In North America, particularly the United States, detergents typically have about 300 ppm-1500 ppm of detergent components present in the wash water.

A high detergent concentration system includes detergents where greater than about 2000 ppm of the detergent components are present in the wash water. European detergents are generally considered to be high detergent concentration systems as they have approximately 2000-10000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 300 ppm of detergent composition ("low detergent concentration geographies") to 10000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 1000 ppm of detergent within the wash solution about 64.4 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). However, in the interest of saving energy, many consumers are switching to using cold water washing. In addition, in some further regions, cold water is typically used for laundry, as well as dish washing applications. In some embodiments, the "cold water washing" of the present invention utilizes "cold water detergent" suitable for washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm #divided by 17.1 equals grains per gallon) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present invention provides variant lipolytic enzymes that show surprising wash performance in at least one set of wash conditions (e.g., water temperature, water hardness, and/or detergent concentration). In some embodiments, the variant lipolytic enzymes of the present invention are comparable in wash performance to other lipase lipolytic enzymes. In some embodiments, the variant lipolytic enzymes of the present invention exhibit enhanced wash performance as compared to lipase lipolytic enzymes currently commercially available. Thus, in some embodiments of the present invention, the variant lipolytic enzymes provided herein exhibit enhanced oxidative stability, enhanced thermostability, enhanced cleaning capabilities under various conditions, and/or enhanced chelator stability. In addition, the variant lipolytic enzymes of the present invention find use in cleaning compositions that do not include detergents, again either alone or in combination with builders and stabilizers.

In some embodiments of the present invention, the cleaning compositions comprise at least one variant lipolytic enzyme of the present invention at a level from about 0.00001% to about 10% by weight of the composition and the balance (e.g., about 99.999% to about 90.0%) comprising cleaning adjunct materials by weight of composition. In some other embodiments of the present invention, the cleaning compositions of the present invention comprises at least one variant lipolytic enzyme at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In some embodiments, the cleaning compositions of the present invention comprise one or more additional detergent enzymes, which provide cleaning performance and/or fabric care and/or dishwashing benefits. Examples of suitable enzymes include, but are not limited to, hemicellulases, cellulases, peroxidases, lipolytic enzymes, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases, or any combinations or mixtures thereof. In some embodiments, a combination of enzymes is used (i.e., a "cocktail") comprising conventional applicable enzymes like lipolytic enzyme, lipase, cutinase and/or cellulase in conjunction with amylase is used.

For example, a lipolytic enzyme variant of the invention can be combined with a protease. Suitable proteolytic enzymes include those of animal, vegetable or microbial origin. In some embodiments, microbial proteolytic enzymes are used. In some embodiments, the proteolytic enzyme is preferably an alkaline microbial proteolytic enzyme or a trypsin-like proteolytic enzyme. Examples of alkaline lipolytic enzymes include lipases, especially those derived from *Bacillus* (e.g., *lentus, amyloliquefaciens*, Carlsberg, 309, 147 and 168). Additional examples include those mutant proteolytic enzymes described in U.S. Pat. Nos. RE 34,606, 5,955,340, 5,700,676, 6,312,936, and 6,482,628, all of which are incorporated herein by reference. Additional protease examples include, but are not limited to trypsin (e.g., of *porcine* or *bovine* origin), and the *Fusarium* protease enzyme described in WO 89/06270. In some embodiments, commercially available protease enzymes that find use in the present invention include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™ and PURAFAST™ (Genencor); ALCALASE®, SAVINASE®, PRIMASE®, DURAZYM™, POLARZYME®, OVOZYME®, KANNASE®, LIQUA- NASE®, NEUTRASE®, RELASE® and ESPERASE® (Novozymes); BLAP™ and BLAP™ variants (Henkel Kommanditgesellschaft auf Aktien, Duesseldorf, Germany), and KAP (*B. alkalophilus* lipase; Kao Corp., Tokyo, Japan). Various proteolytic enzymes are described in WO95/23221, WO 92/21760, U.S. Pat. Publ. No. 2008/0090747, and U.S. Pat. Nos. 5,801,039, 5,340,735, 5,500,364, 5,855,625, U.S. Pat. Nos. RE 34,606, 5,955,340, 5,700,676, 6,312,936, and 6,482,628, and various other patents. In some further embodiments, metalloprotease enzymes find use in the present invention, including but not limited to the neutral metalloprotease enzyme described in WO 07/044993.

In some embodiments of the present invention, any suitable amylase finds use in the present invention. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present invention, include, but are not limited to α-amylases obtained from *B. licheniformis* (See e.g., GB 1,296, 839). Commercially available amylases that find use in the present invention include, but are not limited to DURAMYL®, TERMAMYL®, FUNGAMYL®, STAINZYME®, STAINZYME PLUS®, STAINZYME ULTRA®, and BAN™ (Novozymes), as well as POWERASE™, RAPIDASE® and MAXAMYL® P (Genencor).

In some embodiments of the present invention, the cleaning compositions of the present invention further comprise amylases at a level from about 0.00001% to about 10% of additional amylase by weight of the composition and the balance of cleaning adjunct materials by weight of composition. In some other embodiments of the present invention, the cleaning compositions of the present invention also comprise amylases at a level of about 0.0001% to about 10%, about 0.001% to about 5%, about 0.001% to about 2%, about 0.005% to about 0.5% amylase by weight of the composition.

In some further embodiments, any suitable cellulase finds used in the cleaning compositions of the present invention. Suitable cellulases include, but are not limited to those of bacterial or fungal origin. Chemically or genetically modified mutants are included in some embodiments. Suitable cellulases include, but are not limited to *Humicola insolens* cellulases (See e.g., U.S. Pat. No. 4,435,307). Especially suitable cellulases are the cellulases having color care benefits (See e.g., EP 0 495 257). Commercially available cellulases that find use in the present include, but are not limited to CELLUZYME®, CAREZYME® (Novozymes), and KAC-500(B)™ (Kao Corporation) PURADAX HA 1200E (Danisco), PURADAX EG 7000L(Danisco). In some embodiments, cellulases are incorporated as portions or fragments of mature wild-type or variant cellulases, wherein a portion of the N-terminus is deleted (See e.g., U.S. Pat. No. 5,874,276). In some embodiments, the cleaning compositions of the present invention further comprise cellulases at a level from about 0.00001% to about 10% of additional cellulase by weight of the composition and the balance of cleaning adjunct materials by weight of composition. In some other embodiments of the present invention, the cleaning compositions of the present invention also comprise cellulases at a level of about 0.0001% to about 10%, about 0.001% to about 5%, about 0.001% to about 2%, about 0.005% to about 0.5% cellulase by weight of the composition.

Any mannanase suitable for use in detergent compositions also finds use in the present invention. Suitable mannanases include, but are not limited to those of bacterial or fungal origin. Chemically or genetically modified mutants are included in some embodiments. Various mannanases are known which find use in the present invention (See e.g., U.S. Pat. Nos. 6,566,114, 6,602,842, and 6,440,991, all of which are incorporated herein by reference). In some embodiments, the cleaning compositions of the present invention further comprise mannanases at a level from about 0.00001% to about 10% of additional mannanase by weight of the composition and the balance of cleaning adjunct materials by weight of composition. In some embodiments of the present invention, the cleaning compositions of the present invention also comprise mannanases at a level of about 0.0001% to about 10%, about 0.001% to about 5%, about 0.001% to about 2%, about 0.005% to about 0.5% mannanase by weight of the composition.

In some embodiments, peroxidases are used in combination with hydrogen peroxide or a source thereof (e.g., a percarbonate, perborate or persulfate) in the compositions of the present invention. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present invention further comprise peroxidase and/or oxidase enzymes at a level from about 0.00001% to about 10% of additional peroxidase and/or oxidase by weight of the composition and the balance of cleaning adjunct materials by weight of composition. In some other embodiments of the present invention, the cleaning compositions of the present invention also comprise, peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See e.g., WO 05/056782). In addition, in some embodiments, mixtures of the above mentioned enzymes are encompassed herein, in particular one or more additional lipolytic enzyme, amylase, protease, mannanase, and/or at least one cellulase. Indeed, it is contemplated that various mixtures of these enzymes will find use in the present invention. It is also contemplated that the varying levels of the variant lipolytic enzyme(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See e.g., U.S. Pat. Nos. 6,610,642, 6,605,458, 5,705,464, 5,710,115, 5,698,504, 5,695,679, 5,686,014 and 5,646,101, all of which are incorporated herein by reference). Embodiments of specific cleaning composition materials are exemplified in detail below. In embodiments in which the cleaning adjunct materials are not compatible with the variant lipolytic enzymes of the present invention in the cleaning compositions, then suitable methods of keeping the cleaning adjunct materials and the lipolytic enzyme(s) separated (i.e., not in contact with each other) until combination of the two components is appropriate are used. Such separation methods include any suitable method known in the art (e.g., gelcaps, encapsulation, tablets, physical separation, etc.).

In some embodiments, an effective amount of one or more variant lipolytic enzyme(s) provided herein is included in compositions useful for cleaning a variety of surfaces in need of lipid stain removal. Such cleaning compositions include cleaning compositions for such applications as cleaning hard surfaces, fabrics, and dishes. Indeed, in some embodiments, the present invention provides fabric cleaning compositions, while in other embodiments, the present invention provides non-fabric cleaning compositions. It is intended that the present invention encompass detergent compositions in any form (i.e., liquid, granular, bar, semi-solid, gels, emulsions, tablets, capsules, etc.).

By way of example, several cleaning compositions wherein the variant lipolytic enzymes of the present invention find use are described in greater detail below. In some embodiments in which the cleaning compositions of the present invention are formulated as compositions suitable for use in laundry machine washing method(s), the compositions of the present invention preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present invention also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the invention preferably contain at least one surfactant and preferably at least one additional cleaning adjunct material selected from organic polymeric compounds, suds enhancing agents, group II metal ions, solvents, hydrotropes and additional enzymes.

In some embodiments, various cleaning compositions such as those provided in U.S. Pat. No. 6,605,458, find use with the variant lipolytic enzymes of the present invention. Thus, in some embodiments, the compositions comprising at least one variant lipolytic enzyme of the present invention is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one variant lipolytic enzyme of the present invention are fabric cleaning compositions such as those described in U.S. Pat. Nos. 6,610,642 and 6,376,450. In addition, the variant lipolytic enzymes of the present invention find use in granular laundry detergent compositions of particular utility under European or Japanese washing conditions (See e.g., U.S. Pat. No. 6,610,642).

In some alternative embodiments, the present invention provides hard surface cleaning compositions comprising at least one variant lipolytic enzyme provided herein. Thus, in some embodiments, the compositions comprising at least one variant lipolytic enzyme of the present invention is a hard surface cleaning composition such as those described in U.S. Pat. Nos. 6,610,642, 6,376,450, and 6,376,450.

In yet further embodiments, the present invention provides dishwashing compositions comprising at least one variant lipolytic enzyme provided herein. Thus, in some embodiments, the compositions comprising at least one variant lipolytic enzyme of the present invention is a hard surface cleaning composition such as those in U.S. Pat. Nos. 6,610,642 and 6,376,450. In some still further embodiments, the present invention provides dishwashing compositions comprising at least one variant lipolytic enzyme provided herein. In some further embodiments, the compositions comprising at least one variant lipolytic enzyme of the present invention comprise oral care compositions such as those in U.S. Pat. No. 6,376,450, and 6,376,450. The formulations and descriptions of the compounds and cleaning adjunct materials contained in the aforementioned U.S. Pat. Nos. 6,376,450, 6,605,458, 6,605,458, and 6,610,642, find use with the variant lipolytic enzymes provided herein.

The cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,565,422, 5,516,448, 5,489,392, and 5,486,303, all of which are incorporated herein by reference. When a low pH cleaning composition is desired, the pH of such composition is adjusted via the addition of a material such as monoethanolamine or an acidic material such as HCl.

While not essential for the purposes of the present invention, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the variant lipolytic enzymes of the present invention. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812, and 6,326,348, incorporated by reference. The aforementioned adjunct ingredients may constitute the balance of the cleaning compositions of the present invention.

In some embodiments, the cleaning compositions according to the present invention comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions the acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition. Builders include, but are not limited to, the alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present invention, including those known in the art (See e.g., EP 2 100 949).

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present invention. In some embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some embodiments, the anti-redeposition agent is a non-ionic surfactant as known in the art (See e.g., EP 2 100 949).

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

In some embodiments, silicates are included within the compositions of the present invention. In some such embodiments, sodium silicates (e.g., sodium disilicate, sodium metasilicate, and crystalline phyllosilicates) find use. In some embodiments, silicates are present at a level of from about 1% to about 20%. In some embodiments, silicates are present at a level of from about 5% to about 15% by weight of the composition.

In some still additional embodiments, the cleaning compositions of the present invention also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), Tin (II), cobalt (II), copper (II), nickel (II), and oxovanadium (IV). Chlorides and sulfates also find use in some embodiments of the present invention. Examples of suitable oligosaccharides and polysaccharides (e.g., dextrins) are known in the art (See e.g., WO 07/145964). In some embodiments, reversible enzyme inhibitors also find use, such as boron-containing compounds (e.g., borate, 4-formyl phenyl boronic acid) and/or a tripeptide aldehyde find use to further improve stability, as desired.

In some embodiments, bleaches, bleach activators and/or bleach catalysts are present in the compositions of the present invention. In some embodiments, the cleaning compositions of the present invention comprise inorganic and/or organic bleaching compound(s). Inorganic bleaches include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present invention (See e.g., EP 2 100 949).

In some embodiments, bleach activators are used in the compositions of the present invention. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from about 1 to about 10 carbon atoms, in particular from about 2 to about 4 carbon atoms, and/or optionally substituted perbenzoic acid. Additional bleach activators are known in the art and find use in the present invention (See e.g., EP 2 100 949).

In addition, in some embodiments and as further described herein, the cleaning compositions of the present invention further comprise at least one bleach catalyst. In some embodiments, the manganese triazacyclononane and related complexes find use, as well as cobalt, copper, manganese, and iron complexes. Additional bleach catalysts find use in the present invention (See e.g., U.S. Pat. Nos. 4,246,612, 5,227,084, 4,810410, WO 99/06521, and EP 2 100 949).

In some embodiments, the cleaning compositions of the present invention contain one or more catalytic metal complexes. In some embodiments, a metal-containing bleach catalyst finds use. In some embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243). In some embodiments, the cleaning compositions of the present invention are catalyzed by means of a manganese compound. Such compounds and levels of use are well known in the art (See e.g., U.S. Pat. No. 5,576,282). In additional embodiments, cobalt bleach catalysts find use in the cleaning compositions of the present invention. Various cobalt bleach catalysts are known in the art (See e.g., U.S. Pat. Nos. 5,597,936 and 5,595,967) and are readily prepared by known procedures.

In some additional embodiments, the cleaning compositions of the present invention include a transition metal complex of a macropolycyclic rigid ligand (MRL). As a practical matter, and not by way of limitation, in some embodiments, the compositions and cleaning processes provided by the present invention are adjusted to provide on the order of at least one part per hundred million of the active MRL species in the aqueous washing medium, and in some embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, transition-metals in the instant transition-metal bleach catalyst include, but are not limited to manganese, iron and chromium. MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 2000/32601, and U.S. Pat. No. 6,225,464).

In some embodiments, the cleaning compositions of the present invention comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 9426860 and WO 94/26859). In some embodiments, the metal care agent is a zinc salt. In some further embodiments, the cleaning compositions of the present invention comprise from about 0.1% to about 5% by weight of one or more metal care agent.

As indicated above, the cleaning compositions of the present invention are formulated into any suitable form and prepared by any process chosen by the formulator, non-limiting examples of which are described in U.S. Pat. Nos. 5,879,584, 5,691,297, 5,574,005, 5,569,645, 5,516,448, 5,489,392, and 5,486,303, all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, item, dishware, or fabric). Typically, at least a portion of the situs is contacted with an embodiment of the present cleaning composition, in neat form or diluted in a wash liquor, and then the situs is optionally washed and/or rinsed. For purposes of the present invention, "washing" includes but is not limited to, scrubbing, and mechanical agitation. In some embodiments, the cleaning compositions are typically employed at concentrations of from about 300 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

Processes of Making and Using Cleaning Compositions

The cleaning compositions of the present invention are formulated into any suitable form and prepared by any suitable process chosen by the formulator, (See e.g., U.S. Pat. Nos. 5,879,584, 5,691,297, 5,574,005, 5,569,645, 5,565,422, 5,516,448, 5,489,392, 5,486,303, 4,515,705, 4,537,706, 4,515,707, 4,550,862, 4,561,998, 4,597,898, 4,968,451, 5,565,145, 5,929,022, 6,294,514 and 6,376,445).

In some embodiments, the cleaning compositions of the present invention are provided in unit dose form, including tablets, capsules, sachets, pouches, and multi-compartment pouches. In some embodiments, the unit dose format is designed to provide controlled release of the ingredients within a multi-compartment pouch (or other unit dose format). Suitable unit dose and controlled release formats are known in the art (See e.g., EP 2 100 949, WO 02/102955, U.S. Pat. Nos. 4,765,916 and 4,972,017, and WO 04/111178 for materials suitable for use in unit dose and controlled release formats). In some embodiments, the unit dose form is provided by tablets wrapped with a water-soluble film or water-soluble pouches. Various formats for unit doses are provided in EP 2 100 947, and are known in the art.

Methods of Use

In some embodiments, the cleaning compositions of the present invention find use in cleaning surfaces (e.g., dishware), laundry, hard surfaces, contact lenses, etc. In some embodiments, at least a portion of the surface is contacted with at least one embodiment of the cleaning compositions of the present invention, in neat form or diluted in a wash liquor, and then the surface is optionally washed and/or rinsed. For purposes of the present invention, "washing" includes, but is not limited to, scrubbing, and mechanical washing. In some embodiments, the cleaning compositions of the present invention are used at concentrations of from about 500 ppm to about 15,000 ppm in solution. In some embodiments in which the wash solvent is water, the water temperature typically ranges from about 5° C. to about 90° C.

The present invention provides methods for cleaning or washing an item or surface (e.g., hard surface) in need of cleaning, including, but not limited to methods for cleaning or washing a dishware item, a tableware item, a fabric item, a laundry item, personal care item, etc., or the like, and methods for cleaning or washing a hard or soft surface (e.g., a hard surface of an item).

In some embodiments, the present invention provides a method for cleaning an item, object, or surface in need of cleaning, the method comprising contacting the item or surface (or a portion of the item or surface desired to be cleaned) with at least one variant lipase lipolytic enzyme of the present invention or a composition of the present invention for a sufficient time and/or under conditions suitable and/or effective to clean the item, object, or surface to a desired degree. Some such methods further comprise rinsing the item, object, or surface with water. For some such methods, the cleaning composition is a dishwashing detergent composition and the item or object to be cleaned is a dishware item or tableware item. As used herein, a "dishware item" is an item generally used in serving or eating food. A dishware item can be, but is not limited to for example, a dish, plate, cup, bowl, etc., and the like. As used herein, "tableware" is a broader term that includes, but is not limited to for example, dishes, cutlery, knives, forks, spoons, chopsticks, glassware, pitchers, sauce boats, drinking vessels, serving items, etc. It is intended that "tableware item" includes any of these or similar items for serving or eating food. For some such methods, the cleaning composition is an automatic dishwashing detergent composition or a hand dishwashing detergent composition and the item or object to be cleaned is a dishware or tableware item. For some such methods, the cleaning composition is a laundry detergent composition (e.g., a power laundry detergent composition or a liquid laundry detergent composition), and the item to be cleaned is a fabric item. In some other embodiments, the cleaning composition is a laundry pre-treatment composition.

In some embodiments, the present invention provides methods for cleaning or washing a fabric item optionally in need of cleaning or washing, respectively. In some embodiments, the methods comprise providing a composition comprising the variant lipolytic enzyme, including but not limited to fabric or laundry cleaning composition, and a fabric item or laundry item in need of cleaning, and contacting the fabric item or laundry item (or a portion of the item desired to be cleaned) with the composition under conditions sufficient or effective to clean or wash the fabric or laundry item to a desired degree.

In some embodiments, the present invention provides a method for cleaning or washing an item or surface (e.g., hard surface) optionally in need of cleaning, the method comprising providing an item or surface to be cleaned or washed and contacting the item or surface (or a portion of the item or surface desired to be cleaned or washed) with at least one lipase variant of the invention or a composition of the invention comprising at least one such lipase variant for a sufficient time and/or under conditions sufficient or effective to clean or wash the item or surface to a desired degree. Such compositions include, but are not limited to for example, a cleaning composition or detergent composition of the invention (e.g., a hand dishwashing detergent composition, hand dishwashing cleaning composition, laundry detergent or fabric detergent or laundry or fabric cleaning composition, liquid laundry detergent, liquid laundry cleaning composition, powder laundry detergent composition, powder laundry cleaning composition, automatic dishwashing detergent composition, laundry booster cleaning or detergent composition, laundry cleaning additive, and laundry pre-spotter composition, etc.). In some embodiments, the method is repeated one or more times, particularly if additional cleaning or washing is desired. For example, in some instance, the method optionally further comprises allowing the item or surface to remain in contact with the at least one variant lipolytic enzyme or composition for a period of time sufficient or effective to clean or wash the item or surface to the desired degree. In some embodiments, the methods further comprise rinsing the item or surface with water and/or another liquid. In some embodiments, the methods further comprise contacting the item or surface with at least one variant lipolytic enzyme of the invention or a composition of the invention again and allowing the item or surface to remain in contact with the at least one variant lipolytic enzyme or composition for a period of time sufficient to clean or wash the item or surface to the desired degree. In some embodiments, the cleaning composition is a dishwashing detergent composition and the item to be cleaned is a dishware or tableware item. In some embodiments of the present methods, the cleaning composition is an automatic dishwashing detergent composition or a hand dishwashing detergent composition and the item to be cleaned is a dishware or tableware item. In some embodiments of the methods, the cleaning composition is a laundry detergent composition and the item to be cleaned is a fabric item.

The present invention also provides methods of cleaning a tableware or dishware item in an automatic dishwashing machine, the method comprising providing an automatic dishwashing machine, placing an amount of an automatic dishwashing composition comprising at least one lipase variant of the present invention or a composition of the invention sufficient to clean the tableware or dishware item in the machine (e.g., by placing the composition in an appropriate or provided detergent compartment or dispenser in the machine), putting a dishware or tableware item in the machine, and operating the machine so as to clean the tableware or dishware item (e.g., as per the manufacturer's instructions). In some embodiments, the methods include any automatic dishwashing composition described herein, which comprises, but is not limited to at least one lipase variant provided herein. The amount of automatic dishwashing composition to be used can be readily determined according to the manufacturer's instructions or suggestions and any form of automatic dishwashing composition comprising at least one variant lipolytic enzyme of the invention (e.g., liquid, powder, solid, gel, tablet, etc.), including any described herein, may be employed.

The present invention also provides methods for cleaning a surface, item or object optionally in need of cleaning, the method comprises contacting the item or surface (or a portion of the item or surface desired to be cleaned) with at least one variant lipase of the present invention or a cleaning composition of the invention in neat form or diluted in a wash liquor for a sufficient time and/or under conditions sufficient or effective to clean or wash the item or surface to a desired degree. The surface, item, or object may then be (optionally) washed and/or rinsed if desired. For purposes of the present invention, "washing" includes, but is not limited to for example, scrubbing and mechanical agitation. In some embodiments, the cleaning compositions are employed at concentrations of from about 500 ppm to about 15,000 ppm in solution (e.g., aqueous solution). When the wash solvent is water, the water temperature typically ranges from about 5° C. to about 90° C. and when the surface, item or object comprises a fabric, the water to fabric mass ratio is typically from about 1:1 to about 30:1.

The present invention also provides methods of cleaning a laundry or fabric item in an washing machine, the method comprising providing an washing machine, placing an amount of a laundry detergent composition comprising at least one variant lipase of the invention sufficient to clean the laundry or fabric item in the machine (e.g., by placing the composition in an appropriate or provided detergent compartment or dispenser in the machine), placing the laundry or fabric item in the machine, and operating the machine so as to clean the laundry or fabric item (e.g., as per the manufacturer's instructions). The methods of the present invention include any laundry washing detergent composition described herein, comprising but not limited to at least one of any variant lipase provided herein. The amount of laundry detergent composition to be used can be readily determined according to manufacturer's instructions or suggestions and any form of laundry detergent composition comprising at least one variant lipolytic enzyme of the invention (e.g., solid, powder, liquid, tablet, gel, etc.), including any described herein, may be employed.

The present invention also provides variants, such as TLL variants, having esterase activity. Esterase activity includes cleavage at esters, for example monomeric, soluble forms of triglycerides. In some embodiments of the invention, variants of the invention can be used in the presence of adjuvants, including non-ionic or zwitterionic adjuvants, for example, n-Dodecyl-beta-D-maltopyranoside (D310), Lyso-Fos Choline 14 (L214), Anzergent 3-12 (AZ312) and CHAPSO (C317). In some embodiments of the invention, variants of the invention can be used with different concentrations of adjuvant levels, including, but not limited to, 1×, 0.5×, and 0.25× critical micelle concentration (CMC).

The present invention also provides variants, such as TLL variants, useful for pulp and paper processing, including controlling organic contaminants in fibers. The fiber can be cellulose fibers and in some instances are recycled fibers from a variety of paper products or fiber containing products, such as old corrugated containers (OCC), old newsprint (ONP), mixed office waste (MOW), or combinations thereof. These types of paper containing products typically contain large amounts of organic contaminants which are present in the paper products. When these types of paper products are recycled, these organic contaminants are present along with the fibers formed during the pulping stage of a papermaking process. These organic contaminants, if not substantially removed, can severely interfere with subsequent stages in the papermaking process by affecting the quality of the resulting sheets of paper formed and/or affecting the machinery used to form the paper. Accordingly, the removal of such organic contaminants is important to the paper making process when such organic contaminants are present in fibers.

For purposes of the present invention, examples of organic contaminants include what is known in the industry as "stickies" and include, but are not limited to, synthetic polymers resulting from adhesives and the like, glues, hot melts, coatings, coating binders, ink residues, de-inking chemicals, wood resins, rosin, and unpulped wet strength resins. These types of materials are typically found in paper containing products, such as newsprint, corrugated container, and/or mixed office waste. These organic contaminants typically will have polymers present, such as styrene butadiene rubber, vinyl acrylates, polyisoprene, polybutadiene, natural rubber, ethyl vinyl acetates, polyvinyl acetates, ethylvinyl alcohols, polyvinyl alcohols, styrene acrylates, and other synthetic type polymers.

In the process of the present invention, these organic contaminants are controlled by contacting the fiber containing the organic contaminants with a composition containing at least one variant of the present invention for a sufficient time and in a sufficient amount to control the organic contaminants present in the fiber. The compositions of the present invention preferably disperse or convert the organic contaminants to organic species that do not affect the paper making process. For instance, the polyvinyl acetates are preferably dispersed and/or converted to polyvinyl alcohols, which do not affect the papermaking process. This preferred manner that the compositions achieve control of organic contaminants is quite different from collecting contaminants by flotation.

For purposes of the present invention, controlling organic contaminants present in fibers having organic contaminants is understood as one or more of the following: reducing the size of contaminant particles, reducing the number or amount of measurable particles present, and/or reducing the tackiness of the organic contaminants. In some embodiments, when controlling organic contaminants using the methods of the present invention, all of these reductions occur. In some embodiments, the reduction of the size of contaminant particles is by at least about 5%, or by from about 10% to about 75% as compared to when no variant of the present invention is present. Similarly, the reduction in the number or amount of organic contaminants present in the fiber is reduced by at least about 5%, or by from about 10% to about 75% when compared to fibers which have not been treated with a variant of the present invention. Also, the reduction of tackiness of the organic contaminants can be reduced by at least about 5%, or by from about 10% to about 75% when compared to fibers which have not been treated with a variant of the present invention.

The compositions containing at least one variant of the present invention can also contain as an option other conventional paper treatment chemicals or ingredients such as, but not limited to, surfactants, solvents, suspension aids, fillers, chelants, preservatives, buffers, water, stabilizers, and the like. These additional ingredients can be present in conventional amounts.

In some embodiments of the invention, a method is provided for treating polyester, including clean, unsoiled polyester, comprising contacting said polyester textile with an enzyme solution having variant of the present invention for a time and under conditions such that the properties of the polyester are modified. Preferably, the polyester is a fiber, yarn, fabric or finished textile product comprising such fiber, yarn or fabric. Further preferably, the properties that are modified comprise those such as improved hand, feel and/or weight of a textile made from such fiber, yarn or article. In some embodiments, the present invention is to provide for a mechanism to modify the textile characteristics of a polyester comprising textile. Thus, in this embodiment of the invention, it is often advantageous to apply the polyesterase to textile products which are unsoiled, i.e., do not comprise stains which are typically subjected to commercial laundry detergents. In other embodiments, the present invention is to provide for a method of laundering stains from polyester fabrics.

In another embodiment of the invention, a method is provided for treating a polyester fiber, yarn or fabric, prior to its incorporation into a textile product or the application of a textile finish with an enzyme variant of the present invention for a time and under conditions such that the properties of the polyester are modified. Accordingly, in the embodiment wherein textile components are treated separately, the treated polyester components (i.e., fibers, yarns, fabrics), can be incorporated into a textile product through standard methods for producing polyester textiles, e.g., processes such as weaving, sewing and cutting and stitching, thus conferring the modifications to the finished textile product.

In yet another method embodiment of the invention, a method is provided for treating a polyester resin or film with an enzyme variant of the present invention for a time and under conditions such that the properties of the polyester are modified. The treated polyester may be a finished resin or film product or may be incorporated into a product through, for example, mechanical construction, thus conferring the modifications to the finished textile product.

In yet another method embodiment of the invention, a polyester waste product is treated with an enzyme variant of the present invention to degrade the polyester waste product to easily dispose of or recycled compounds. This embodiment is particularly useful in the degradation of polyester based plastics which are becoming increasingly problematic in waste disposal and dumping. An alternative of this embodiment is that the present invention may be used to increase the amount of microbially digestible material in a waste product so as to facilitate complete degradation or composting of such waste.

In the method according to the invention, the solution containing an enzyme variant of the present invention as provided herein is contacted with the polyester fiber, yarn, fabric or textile which comprises such fiber, yarn or fabric under conditions suitable for the enzyme to exhibit polyester modification. The present invention is preferably directed to the use of the polyesterase in the manufacture of the textile product, and not necessarily in combination with a detergent for the purpose of removing stains which occur during wear. Thus, in this embodiment, the application of the enzyme variant of the present invention to the polyester article occurs prior to spinning of the fiber into a yarn, prior to the incorporation of the yarn into a fabric and/or prior to the construction of the textile product which comprises the polyester. However, it is within the present invention as well, and also a preferred embodiment hereon, to treat the completed textile product with the enzyme variant of the present invention identified herein.

EXPERIMENTAL

The present invention is described in further detail in the following examples which are not in any way intended to limit the scope of the invention as claimed.

In the experimental disclosure which follows, the following abbreviations apply: PI (Performance Index), ppm (parts per million); M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); rpm (revolutions per minute); GH (degrees German hardness); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); w/w (weight to weight); g (gravity); OD (optical density); ppm (parts per million); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto-Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); $A_{405}$ (absorbance at 405 nm); Vmax (the maximum initial velocity of an enzyme catalyzed reaction); PAGE (polyacrylamide gel electrophoresis); PBS (phosphate buffered saline [150 mM NaCl, 10 mM sodium phosphate buffer, pH 7.2]); PBST (PBS+0.25% TWEEN®-20); PEG (polyethylene glycol); PCR (polymerase chain reaction); RT-PCR (reverse transcription PCR); SDS (sodium dodecyl sulfate); Tris (tris (hydroxymethyl)aminomethane); HEPES (N-[2-Hydroxyethyl]piperazine-N-[2-ethanesulfonic acid]); HBS (HEPES buffered saline); Tris-HCl (tris[Hydroxymethyl]aminomethane-hydrochloride); Tricine (N-[tris-(hydroxymethyl)-methyl]-glycine); CHES (2-(N-cyclo-hexylamino) ethanesulfonic acid); TAPS (3-{[tris-(hydroxymethyl)-methyl]-amino}-propanesulfonic acid); CAPS (3-(cyclohexylamino)-propane-sulfonic acid; DMSO (dimethyl sulfoxide); DTT (1,4-dithio-DL-threitol); SA (sinapinic acid (s,5-dimethoxy-4-hydroxy cinnamic acid); TCA (trichloroacetic acid); Glut and GSH (reduced glutathione); GSSG (oxidized glutathione); TCEP (Tris[2-carboxyethyl] phosphine); Ci (Curies); mCi (milliCuries); µCi (microCuries); HPLC (high pressure liquid chromatography); RP-HPLC (reverse phase high pressure liquid chromatography); TLC (thin layer chromatography); MALDI-TOF (matrix-assisted laser desorption/ionization-time of flight); Ts (tosyl); Bn (benzyl); Ph (phenyl); Ms (mesyl); Et (ethyl), Me (methyl); Taq (*Thermus aquaticus* DNA polymerase); Klenow (DNA polymerase I large (Klenow) fragment); EGTA (ethylene glycol-bis(β-aminoethyl ether) N,N,N',N'-tetraacetic acid); EDTA (ethylenediaminetetracetic acid); bla (β-lactamase or ampicillin-resistance gene); HDL (high density liquid); HDD (heavy duty powder detergent); HSG (high suds granular detergent); CEE (Central and Eastern Europe); WE (Western Europe); NA, when used in reference to detergents (North America); Japan and JPN, when used in reference to detergents (Japan); MJ Research (MJ Research, Reno, Nev.); Baseclear (Baseclear BV, Inc., Leiden, the Netherlands); PerSeptive (PerSeptive Biosystems, Framingham, Mass.); ThermoFinnigan (ThermoFinnigan, San Jose, Calif.); Argo (Argo BioAnalytica, Morris Plains, N.J.); Seitz EKS (SeitzSchenk Filtersystems GmbH, Bad Kreuznach, Germany); Pall (Pall Corp., East Hills, N.Y. and Bad Kreuznach, Germany); Spectrum (Spectrum Laboratories, Dominguez Rancho, Calif.); Molecular Structure (Molecular Structure Corp., Woodlands, Tex.); Accelrys (Accelrys, Inc., San Diego, Calif.); Chemical Computing (Chemical Computing Corp., Montreal, Canada); New Brunswick (New Brunswick Scientific, Co., Edison, N.J.); CFT (Center for Test Materials, Vlaardingen, the Netherlands); P&G and Proctor & Gamble (Proctor & Gamble, Inc., Cincinnati, Ohio); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Finnzymes (Finnzymes Oy, Espoo, Finland); Kelco (CP Kelco, Wilmington, Del.); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); NCBI (National Center for Biotechnology Information); Applied Biosystems (Applied Biosystems, Foster City, Calif.); BD Biosciences and/or Clontech (BD Biosciences CLONTECH Laboratories, Palo Alto, Calif.); Operon Technologies (Operon Technologies, Inc., Alameda, Calif.); MWG Biotech (MWG Biotech, High Point, N.C.); Oligos Etc (Oligos Etc. Inc, Wilsonville, Oreg.); Bachem (Bachem Bioscience, Inc., King of Prussia, Pa.); Difco (Difco Laboratories, Detroit, Mich.); Mediatech (Mediatech, Herndon, Va.; Santa Cruz (Santa Cruz Biotechnology, Inc., Santa Cruz, Calif.); Oxoid (Oxoid Inc., Ogdensburg, N.Y.); Worthington (Worthington Biochemical Corp., Freehold, N.J.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San Diego, Calif.); NEB (New England Biolabs, Beverly, Mass.); Sigma (Sigma Chemical Co., St. Louis, Mo.); Pierce (Pierce Biotechnology, Rockford, Ill.); Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Me.); Aptagen (Aptagen, Inc., Herndon, Va.); Sorvall (Sorvall brand, from Kendro Laboratory Products, Asheville, N.C.); Molecular Devices (Molecular Devices, Corp., Sunnyvale, Calif.); R&D Systems (R&D Systems, Minneapolis, Minn.); Siegfried Handel (Siegfried Handel AG, Zofingen, Switzerland); Stratagene (Stratagene Cloning Systems, La Jolla, Calif.); Marsh (Marsh Biosciences, Rochester, N.Y.); Geneart (Geneart GmbH, Regensburg, Germany); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); New Objective (New Objective brand; Scientific Instrument Services, Inc., Ringoes, N.J.); Waters (Waters, Inc., Milford, Mass.); Matrix Science (Matrix Science, Boston, Mass.); Dionex (Dionex, Corp., Sunnyvale, Calif.); Monsanto (Monsanto Co., St. Louis, Mo.); Wintershall (Wintershall AG, Kassel, Germany); BASF (BASF Co., Florham Park, N.J.); Huntsman (Huntsman Petrochemical Corp., Salt Lake City, Utah); Shell Chemicals (Shell Chemicals, Inc., London, UK); Stepan (Stepan, Northfield, Ill.); Clariant (Clariant, Sulzbach, Germany); Industrial Zeolite (Industrial Zeolite Ltd., Grays, Essex, UK); Jungbunzlauer (Jungbunzlauer, Basel, Switzerland); Solvay (Solvay, Brussels, Belgium); 3V Sigma (3V Sigma, Bergamo, Italy); Innospec (Innospec, Ellesmere Port, UK); Thermphos (Thermphos, Vlissiggen-Ost, the Netherlands); Ciba Specialty (Ciba Specialty Chemicals, Basel, Switzerland); Dow Corning (Dow Corning, Barry, UK); Enichem (Enichem Iberica, Barcelona, Spain); Fluka Chemie AG (Fluka Chemie AG, Buchs, Switzerland); Gist-Brocades (Gist-Brocades, NV, Delft, the Netherlands); Dow Corning (Dow Corning Corp., Midland, Mich.); Mettler-Toledo (Mettler-Toledo Inc, Columbus, Ohio); RB (Reckitt-Benckiser, Slough, UK); and Microsoft (Microsoft, Inc., Redmond, Wash.).

As used herein, in some lists, a leading "0" is indicated, in order to provide a three number designation for each site (e.g., "001" is the same as "1," so "A001C" is the same as "A1C"). In some lists, the leading "0" is not included. In addition, as used herein, "X" refers to any amino acid.

In the exemplified detergent compositions provided herein, the enzymes levels are expressed by pure enzyme by weight of the total composition and unless otherwise specified, the detergent ingredients are expressed by weight of the total compositions. The abbreviated component identifications therein have the following meanings:

| Abbreviation | Ingredient |
| --- | --- |
| LAS | Sodium linear $C_{11-13}$ alkyl benzene sulfonate. |
| NaC16-17HSAS | Sodium $C_{16-17}$ highly soluble alkyl sulfate |
| TAS | Sodium tallow alkyl sulphate. |
| CxyAS | Sodium $C_{1x}$-$C_{1y}$ alkyl sulfate. |
| CxyEz | $C_{1x}$-$C_{1y}$ predominantly linear primary alcohol condensed with an average of z moles of ethylene oxide. |
| CxyAEzS | $C_{1x}$-$C_{1y}$ sodium alkyl sulfate condensed with an average of z moles of ethylene oxide. Added molecule name in the examples. |
| Nonionic | Mixed ethoxylated/propoxylated fatty alcohol e.g. Plurafac LF404 being an alcohol with an average degree of ethoxylation of 3.8 and an average degree of propoxylation of 4.5. |
| QAS | $R_2 \bullet N+(CH_3)_2(C_2H_4OH)$ with $R_2 = C_{12}$-$C_{14}$. |
| Silicate | Amorphous Sodium Silicate ($SiO_2$:$Na_2O$ ratio = 1.6-3.2:1). |
| Metasilicate | Sodium metasilicate ($SiO_2$:$Na_2O$ ratio = 1.0). |
| Zeolite A | Hydrated aluminosilicate of formula $Na_{12}(AlO_2SiO_2)_{12} \bullet 27H_2O$ |
| SKS-6 | Crystalline layered silicate of formula $\delta$-$Na_2Si_2O_5$. |
| Sulfate | Anhydrous sodium sulphate. |
| STPP | Sodium Tripolyphosphate. |
| MA/AA | Random copolymer of 4:1 acrylate/maleate, average molecular weight about 70,000-80,000. |

-continued

| Abbreviation | Ingredient |
| --- | --- |
| AA | Sodium polyacrylate polymer of average molecular weight 4,500. |
| Polycarboxylate | Copolymer comprising mixture of carboxylated monomers such as acrylate, maleate and methyacrylate with a MW ranging between 2,000-80,000 such as Sokolan commercially available from BASF, being a copolymer of acrylic acid, MW 4,500. |
| BB1 | 3-(3,4-Dihydroisoquinolinium)propane sulfonate |
| BB2 | 1-(3,4-dihydroisoquinolinium)-decane-2-sulfate |
| PB1 | Sodium perborate monohydrate. |
| PB4 | Sodium perborate tetrahydrate of nominal formula $NaBO_3 \cdot 4H_2O$. |
| Percarbonate | Sodium percarbonate of nominal formula $2Na_2CO_3 \cdot 3H_2O_2$. |
| TAED | Tetraacetyl ethylene diamine. |
| NOBS | Nonanoyloxybenzene sulfonate in the form of the sodium salt. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Diamine | Dimethyl aminopropyl amine; 1,6-hezane diamine; 1,3-propane diamine; 2-methyl-1,5-pentane diamine; 1,3-pentanediamine; 1-methyl-diaminopropane. |
| DETBCHD | 5,12-diethyl-1,5,8,12-tetraazabicyclo[6,6,2]hexadecane, dichloride, Mn(II) SALT |
| PAAC | Pentaamine acetate cobalt(III) salt. |
| Paraffin | Paraffin oil sold under the tradename Winog 70 by Wintershall. |
| Paraffin Sulfonate | A Paraffin oil or wax in which some of the hydrogen atoms have been replaced by sulfonate groups. |
| Aldose oxidase | Oxidase enzyme sold under the tradename Aldose Oxidase by Novozymes A/S |
| Galactose oxidase | Galactose oxidase from Sigma |
| nprE | The recombinant form of neutral metallolipolytic enzyme expressed in *Bacillus subtilis* (See e.g., WO 07/044993) |
| PMN | Purified neutral metallolipolytic enzyme from *Bacillus amyloliquefacients*. |
| Amylase | A suitable amylolytic enzyme, such as those sold under the tradenames PURAFECT ® Ox described in WO 94/18314, WO96/05295 sold by Genencor; NATALASE ®, TERMAMYL ®, FUNGAMYl ® and DURAMYL ™, all available from Novozymes A/S. |
| Lipase | A suitable lipolytic enzyme such as those sold under the tradenames LIPEX ®, LIPOLASE ®, LIPOLASE ® Ultra by Novozymes A/S and Lipomax ™ by Gist-Brocades. |
| Cellulase | A suitable cellulytic enzyme such as those sold under the tradenames CAREZYME ®, CELLUZYME ®, and/or ENDOLASE ® by Novozymes A/S add ours. |
| Pectin Lyase | A suitable pectin lyase, such as those sold under the tradenames PECTAWAY ® and PECTAWASH ® available from Novozymes A/S. |
| PVP | Polyvinylpyrrolidone with an average molecular weight of 60,000 |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Silicone antifoam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| SRP 1 | Anionically end capped poly esters. |
| PEG X | Polyethylene glycol, of a molecular weight of x. |
| PVP K60 ® | Vinylpyrrolidone homopolymer (average MW 160,000) |
| Jeffamine ® ED-2001 | Capped polyethylene glycol from Huntsman |
| Isachem ® AS | A branched alcohol alkyl sulphate from Enichem |
| MME PEG (2000) | Monomethyl ether polyethylene glycol (MW 2000) from Fluka Chemie AG. |
| DC3225C | Silicone suds suppresser, mixture of Silicone oil and Silica from Dow Corning. |
| TEPAE | Tetraethylenepentaamine ethoxylate. |
| BTA | Benzotriazole. |
| Betaine | $(CH_3)_3N^+CH_2COO^-$ |
| Sugar | Industry grade D-glucose or food grade sugar |
| CFAA | $C_{12}$-$C_{14}$ alkyl N-methyl glucamide |
| TPKFA | $C_{12}$-$C_{14}$ topped whole cut fatty acids. |

| Abbreviation | Ingredient |
|---|---|
| Clay | A hydrated aluminumu silicate in a general formula $Al_2O_3SiO_2 \cdot xH_2O$. Types: Kaolinite, montmorillonite, atapulgite, illite, bentonite, halloysite. |
| pH | Measured as a 1% solution in distilled water at 20° C. |

For North American (NA) and Western European (WE) heavy duty liquid laundry (HDL) detergents, heat inactivation of the enzymes present in commercially-available detergents is performed by placing pre-weighed liquid detergent (in a glass bottle) in a water bath at 95° C. for 2 hours. The incubation time for heat inactivation of NA and WE auto dish washing (ADW) detergents is 8 hours. Both un-heated and heated detergents are assayed within 5 minutes of dissolving the detergent to accurately determine percentage deactivated. Enzyme activity is tested by the AAPF assay.

For testing of enzyme activity in heat-inactivated detergents, working solutions of detergents are made from the heat inactivated stocks. Appropriate amounts of water hardness (e.g., 6 gpg or 12 gpg) and buffer are added to the detergent solutions to match the desired conditions. The solutions are mixed by vortexing or inverting the bottles. The following Table provides information regarding some of the commercially-available detergents and test conditions used herein. In some experiments, additional and/or other commercially available detergents find use in the following Examples.

TABLE A

| Laundry and Dish Washing Conditions | | | | | | | |
|---|---|---|---|---|---|---|---|
| Region | Form | Dose | Detergent* | Buffer | Gpg | pH | T (° C.) |
| Laundry (Heavy Duty Liquid and Granular) | | | | | | | |
| NA | HDL | 0.78 g/l | P&G TIDE ® 2X | 5 mM HEPES | 6 | 8.0 | 20 |
| WE | HDL | 5.0 g/L | Henkel PERSIL ™ | 5 mM HEPES | 12 | 8.2 | 40 |
| WE | HDG | 8.0 g/L | P&G ARIEL ® | 2 mM $Na_2 CO_3$ | 12 | 10.5 | 40 |
| JPN | HDG | 0.7 g/L | P&G TIDE ® | 2 mM $Na_2 CO_3$ | 6 | 10.0 | 20 |
| NA | HDG | 1.0 g/L | P&G TIDE ® | 2 mM $Na_2 CO_3$ | 6 | 10.0 | 20 |
| Automatic Dish Washing | | | | | | | |
| WE | ADW | 3.0 g/L | RB CALGONIT ™ | 2 mM $Na_2 CO_3$ | 21 | 10.0 | 40 |
| NA | ADW | 3.0 g/L | P&G CASCADE ® | 2 mM $Na_2 CO_3$ | 9 | 10.0 | 40 |

In some additional Examples, the following solutions find use:

TABLE B

| Working Detergent Solutions | | | | | |
|---|---|---|---|---|---|
| Detergent | Temp (C.) | Detergent g/L | pH | Buffer | Gpg |
| TIDE ® 2X Cold | 16 | 0.98 | 8 | 5 mM HEPES | 6 |
| TIDE ® 2X Cold | 32 | 0.98 | 8 | 5 mM HEPES | 6 |
| TIDE ® 2X Cold | 16 | 0.98 | 7 | 5 mM MOPS | 6 |

Table C provides granular laundry detergent compositions produced in accordance with the invention suitable for laundering fabrics.

TABLE C

| Granular Laundry Detergent Compositions and Their Components | | | | | | |
|---|---|---|---|---|---|---|
| | Detergent Compositions | | | | | |
| Component | 1 | 2 | 3 | 4 | 5 | 6 |
| Linear alkylbenzenesulfonate with aliphatic carbon chain length $C_{11}$-$C_{12}$ | 15 | 12 | 20 | 10 | 12 | 13 |

TABLE C-continued

Granular Laundry Detergent Compositions and Their Components

| Component | Detergent Compositions |  |  |  |  |  |
|---|---|---|---|---|---|---|
|  | 1 | 2 | 3 | 4 | 5 | 6 |
| Other surfactants | 1.6 | 1.2 | 1.9 | 3.2 | 0.5 | 1.2 |
| Phosphate builder(s) | 2 | 3 | 4 |  |  |  |
| Zeolite |  | 1 |  | 1 | 4 | 1 |
| Silicate | 4 | 5 | 2 | 3 | 3 | 5 |
| Sodium Carbonate | 2 | 5 | 5 | 4 | 0 | 3 |
| Polyacrylate (MW 4500) | 1 | 0.6 | 1 | 1 | 1.5 | 1 |
| Carboxymethylcellulose (Finnfix BDAex CPKelco) | 1 | — | 0.3 | — | 1.1 | — |
| Celluclean® (15.6 mg/g) | 0.23 | 0.17 | 0.5 | 0.2 | 0.2 | 0.6 |
| Lipase (20 mg/g) | 0.2 |  | 0.1 |  | 0.3 |  |
| StainzymePlus® (14 mg/g) | 0.23 | 0.17 | 0.5 | 0.2 | 0.2 | 0.6 |
| Mannaway 4.0 T (4 mg/g) | 0.1 |  |  | 0.1 |  | 0.1 |
| Fluorescent Brightener(s) | 0.16 | 0.06 | 0.16 | 0.18 | 0.16 | 0.16 |
| Diethylenetriamine pentaacetic acid or Ethylene diamine tetraacetic acid | 0.6 |  | 0.6 | 0.25 | 0.6 | 0.6 |
| $MgSO_4$ | 1 | 1 | 1 | 0.5 | 1 | 1 |
| Bleach(es) and Bleach activator(s) | 6.88 |  | 6.12 | 2.09 | 1.17 | 4.66 |
| Ethoxylated thiophene Hueing Dye[5] | 0.002 | 0.001 | 0.003 | 0.003 | — | — |
| Direct Violet 9 ex Ciba Specialty Chemicals |  |  |  | 0.0006 | 0.0004 | 0.0006 |
| Sulfate/Citric Acid/ Sodium Bicarbonate/Moisture/perfume | Balance to 100% | | | | | |

[1]Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2]Polyethylenimine (MW = 600) with 20 ethoxylate groups per —NH.
[3]Amphiphilic alkoxylated grease cleaning polymer is a polyethylenimine (MW = 600) with 24 groups per ethoxylate groups per —NH and 16 propoxylate groups per —NH
[4]Reversible lipolytic enzyme inhibitor of structure:

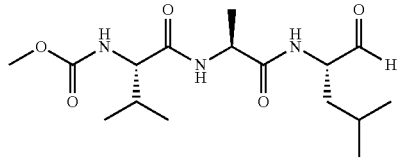 [SMILES: COC(=O)N[C@H](C(=O)N[C@@H](C)C(=O)N[C@H](C=O)CC(C)C)C(C)C]

[5]Ethoxylated thiophene Hueing Dye is as described in U.S. Pat. No. 7,208,459 B2.

In Table C, all enzyme levels expressed as % enzyme raw material, except for lipolytic enzyme (of this invention) which is expressed as % of active protein added to the product.

Table D provides granular laundry detergent compositions suitable for top-loading automatic washing machines (detergent compositions 7-9) and front loading washing machines (detergent compositions 10-11). The lipolytic enzyme variant tested and/or lipolytic enzyme of the present invention is added separately to these formulations so that the final concentration in the wash liquor is between 0.01 ppm and 10 ppm.

TABLE D

Granular Laundry Detergent Compositions and Their Components

| Component | Detergent Composition |  |  |  |  |
|---|---|---|---|---|---|
|  | 7 | 8 | 9 | 10 | 11 |
| Surfactants | | | | | |
| $C_{16-17}$ Branched alkyl sulfate | 3.55 | 15.8 |  |  |  |
| $C_{12-14}$ alkyl sulphate |  |  | 1.5 |  |  |
| Sodium linear alkylbenzenesulfonate with aliphatic chain length $C_{11}$-$C_{12}$ | 9.6 |  | 10.6 | 7.5 | 9 |
| Sodium $C_{14/15}$ alcohol ethoxy - 3 - sulfate | 1.15 |  |  | 2.88 |  |
| Sodium $C_{14/15}$ alkyl sulphate | 2.37 |  |  |  |  |
| $C_{14/15}$ alcohol ethoxylate with average 7 moles of ethoxylation |  |  |  | 1.17 | 1 |
| mono-$C_{8-10}$ alkyl mono-hydroxyethyl di-methyl quaternary ammonium chloride |  |  |  |  | 0.45 |

TABLE D-continued

Granular Laundry Detergent Compositions and Their Components

| Component | 7 | 8 | 9 | 10 | 11 |
|---|---|---|---|---|---|
| Di methyl hydroxyl ethyl lauryl ammonium chloride | | | 0.18 | | |
| Zeolite A | 13.9 | 4.7 | 0.01 | 2.9 | 1.8 |
| Sodium Silicate 1.6.ratio | 4 | 0.2 | | 4 | 4 |
| Sodium Silicate 2.35.ratio | | | 8 | | |
| Citric Acid | | | | 2.5 | 1.4 |
| Sodium tripolyphosphate | | | 5 | | |
| Sodium Carbonate | 24.1 | 30 | 16.9 | 24.4 | 21 |
| Nonanoyloxybenzenesuplhonate | 5.78 | 2.81 | 0.96 | | |
| Oxaziridinium-based bleach booster | | | | 0.03 | 0.017 |
| Tetrasodium S,S,-ethylenediaminedisuccinate | | | | 0.2 | |
| Diethylenetriamine penta (methylene phosphonic acid), heptasodium salt | 0.61 | | | | 0.33 |
| Hydroxyethane dimethylene phosphonic acid | | | | 0.29 | 0.45 |
| Ethylene diamine tetraacetate | | | 0.27 | | |
| MgSO4 | | | 0.47 | 0.5994 | 0.782 |
| Sodium Percarbonate | 7 | 4.4 | | 15.9 | 19.1 |
| Tetra Acetyl Ethylene Diamine | | | | 3.3 | 4.6 |
| Sodium Perborate Monohydrate | | | 1.2 | | |
| Carboxymethyl cellulose (e.g. Finnfix BDA ex CPKelco) | 0.1 | | 0.17 | 1.69 | 0.23 |
| Sodium Acrylic acid/maleic acid co-polymer (70/30) | 0.0236 | 3.8 | | 2 | 2.5 |
| Sodium polyacrylate (Sokalan PA30 CL) | 4 | | 0.84 | | |
| Terephthalate polymer | | | | 0.23 | |
| Polyethylene glycol/vinyl acetate random graft co polymer | | | 0.89 | 0.89 | 0.91 |
| Photobleach- zinc phthalocyanine tetrasulfonate | | | 0.005 | 0.001 | 0.002 |
| C.I. Fluorescent Brightener 260 | 0.11 | 0.15 | 0.04 | 0.23 | 0.15 |
| C.I. Fluorescent Brightener 351 (Tinopal ® CBS) | | | 0.1 | | |
| Suds suppressor granule | | 0.25 | | 0.07 | 0.04 |
| Hydrophobically modified carboxy methyl cellulose (Finnifix ® SH-1) | | | 0.019 | 0.028 | |
| Bentonite | | | 8.35 | | |
| Miscellaneous (Dyes, perfumes, process aids, moisture and sodium sulphate) | Balance | Balance | Balance | Balance | Balance |

In Table D, surfactant ingredients can be obtained from any suitable supplier, including but not limited to BASF (e.g., LUTENSOL®), Shell Chemicals, Stepan, Huntsman, and Clariant (e.g., PRAEPAGEN®). Zeolite can be obtained from sources such as Industrial Zeolite. Citric acid and sodium citrate can be obtained from sources such as Jungbunzlauer. Sodium percarbonate, sodium carbonate, sodium bicarbonate and sodium sesquicarbonate can be obtained from sources such as Solvay. Acrylate/maleate copolymers can be obtained from sources such as BASF. Carboxymethylcellulose and hydrophobically modified carboxymethyl cellulose can be obtained from sources such as CPKelco. C.I. Fluorescent Brightener 260 can be obtained from 3V Sigma (e.g., OPTIBLANC®, OPTIBLANC® 2M/G, OPTIBLANC® 2 MG/LT Extra, or OPTIBLANC® Ecobright. Tetrasodium S,S-ethylenediamine disuccinate can be obtained from sources such as Innospec. Terephthalate co-polymer can be obtained from Clariant (e.g., REPELOTEX SF 2). In addition, 1-Hydroxyethane-1,1-diphosphonic acid can be obtained from Thermphos. Oxaziridinium-based bleach booster has the following structure, where R1=2-butyloctyl, and was produced according to US 2006/0089284A1.

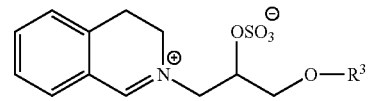

The enzymes NATALASE®, TERMAMYL®, STAINZYME PLUS®, CELLUCLEAN® and MANNAWAY®, can be obtained from Novozymes. Zinc phthalocyanine tetrasulfonate can be obtained from Ciba Specialty Chemicals (e.g., TINOLUX® BMC). Suds suppressor granule can be obtained from Dow Corning. In these detergent compositions, random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

Tables E-G provide additional granular detergent compositions suitable for washing machines (detergents 36a-n). The GG36 lipolytic enzyme variant tested or cold water lipolytic enzyme of the present invention is added separately to these formulations.

TABLE E

Additional Granular Laundry Detergent Compositions and Their Components

| Component | 36a | 36b | 36c | 36d | 36e |
|---|---|---|---|---|---|
| Surfactants | | | | | |
| $C_{10}$ Nonionic | | | | 0.1843 | |
| $C_{16-17}$ Branched alkyl sulfate | 3.53 | 3.53 | 3.53 | | |
| $C_{12-14}$ alkyl sulphate | | | | | |
| Sodium linear alkylbenzenesulfonate with aliphatic chain length $C_{11}$-$C_{12}$ | 8.98 | 8.98 | 8.98 | 13.58 | 14.75 |
| Sodium $C_{14/15}$ alcohol ethoxy - 3 - sulfate | 1.28 | 1.28 | 1.28 | | |
| Sodium $C_{14/15}$ alkyl sulphate | 2.36 | 2.36 | 2.36 | | |
| $C_{14/15}$ alcohol ethoxylate with average 7 moles of ethoxylation | | | | | |
| mono-$C_{8-10}$ alkyl mono-hydroxyethyl di-methyl quaternary ammonium chloride | | | | | |
| Di methyl hydroxyl ethyl lauryl ammonium chloride | | | | 0.1803 | |
| Zeolite A | 15.31 | 15.31 | 15.31 | | 4.47 |
| Bentonite | | | | 8.35 | |
| Sodium Silicate 1.6.ratio | | | | | 0.16 |
| Sodium Silicate 2.0.ratio | 3.72 | 3.72 | 3.72 | 8.41 | |
| Sodium Silicate 2.35.ratio | | | | | |
| Citric Acid | | | | 0.0066 | |
| Sodium tripolyphosphate | | | | 5.06 | |
| Sodium Carbonate | 26.1 | 26.18 | 26.1 | 15.9 | 29.0 |
| Nonanoyloxybenzenesuplhonate | 5.78 | 5.78 | 5.78 | 1.17 | 1.86 |
| Oxaziridinium-based bleach booster | 0.037 | 0.037 | 0.037 | | |
| Tetrasodium S,S,-ethylenediaminedisuccinate | | | | | |
| Diethylenetriamine penta (methylene phosphonic acid), heptasodium salt | 0.62 | 0.62 | 0.62 | | |
| Hydroxyethane dimethylene phosphonic acid | | | | | |
| Ethylene diamine tetraacetate | | | | 0.2701 | |
| MgSO4 | 0.056 | 0.056 | 0.056 | 0.47 | |
| Sodium Percarbonate | | 7.06 | 7.06 | | 3.64 |
| Tetra Acetyl Ethylene Diamine | | | | | |
| Sodium Perborate Monohydrate | | | | 1.47 | |
| Carboxymethyl cellulose (e.g. Finnfix BDA ex CPKelco) | 0.38 | 0.38 | 0.38 | 0.173 | |
| Sodium Acrylic acid/maleic acid co-polymer (70/30) | 3.79 | 3.78 | 3.79 | | 3.64 |
| Sodium polyacrylate (Sokalan PA30 CL) | 3.78 | 3.78 | 3.78 | 0.842 | |
| Terephthalate polymer | | | | | |
| Polyethylene glycol/vinyl acetate random graft co polymer | | | | 0.89 | |
| Photobleach- zinc phthalocyanine tetrasulfonate | | | | | |
| C.I. Fluorescent Brightener 260 | 0.1125 | 0.1125 | 0.1125 | 0.043 | 0.15 |
| C.I. Fluorescent Brightener 351 (Tinopal ® CBS) | | | | 0.0952 | |
| Suds suppressor granule | 0.015 | 0.015 | 0.015 | | 0.031 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE F

Additional Granular Laundry Detergent Compositions and Their Components

| Component | 36f | 36g | 36h | 36i | 36j |
|---|---|---|---|---|---|
| Surfactants | | | | | |
| $C_{10}$ Nonionic | 0.1142 | 0.2894 | 0.1885 | 0.1846 | 0.1885 |
| $C_{16-17}$ Branched alkyl sulfate | | | | | |
| $C_{12-14}$ alkyl sulphate | | | | | |

TABLE F-continued

Additional Granular Laundry Detergent Compositions and Their Components

| Component | Detergent Composition | | | | |
|---|---|---|---|---|---|
| | 36f | 36g | 36h | 36i | 36j |
| Sodium linear alkylbenzenesulfonate with aliphatic chain length $C_{11}$-$C_{12}$ | 12.94 | 15.69 | 9.01 | 8.42 | 9.51 |
| Sodium $C_{14/15}$ alcohol ethoxy-3-sulfate | | | | | |
| Sodium $C_{14/15}$ alkyl sulphate | | | | | |
| $C_{12/14}$ alcohol ethoxylate with average 7 moles of ethoxylation | 2.9 | | | | |
| $C_{12/14}$ alcohol ethoxylate with average 3 moles of ethoxylation | | | | 2.44 | |
| $C_{14/15}$ alcohol ethoxylate with average 7 moles of ethoxylation | | | 0.97 | 1.17 | 0.97 |
| mono-$C_{8-10}$ alkyl mono-hydroxyethyl di-methyl quaternary ammonium chloride | | | 0.45 | | |
| Di methyl hydroxyl ethyl lauryl ammonium chloride | | 0.195 | | | 0.45 |
| Zeolite A | 2.01 | 0.39 | 1.83 | 2.58 | 0.59 |
| Sodium Silicate 1.6.ratio | | | 4.53 | 5.62 | 4.53 |
| Sodium Silicate 2.0.ratio | | 10.1 | | | |
| Sodium Silicate 2.35.ratio | 7.05 | | | | |
| Citric Acid | | | 1.4 | 1.84 | 1.0 |
| Sodium tripolyphosphate | | 5.73 | | | |
| Sodium Carbonate | 12.65 | 15.93 | 21.0 | 27.31 | 20.2 |
| Nonanoyloxybenzenesuplhonate | | 1.73 | | | |
| Oxaziridinium-based bleach booster | | | 0.0168 | 0.0333 | 0.024 |
| Tetrasodium S,S,-ethylenediaminedisuccinate | | | | | |
| Diethylenetriamine penta (methylene phosphonic acid), heptasodium salt | | | 0.327 | | 0.3272 |
| Hydroxyethane dimethylene phosphonic acid | | | 0.45 | 0.2911 | 0.45 |
| Ethylene diamine tetraacetate | | 0.28 | | 0.1957 | |
| MgSO4 | | 0.54 | 0.79 | 0.6494 | 0.793 |
| Sodium Percarbonate | | | 19.1 | 15.85 | 22.5 |
| Tetra Acetyl Ethylene Diamine | | | 4.554 | 3.71 | 5.24 |
| Sodium Perborate Monohydrate | | 5.55 | | | |
| Carboxymethyl cellulose (e.g. Finnfix BDA ex CPKelco) | 0.62 | 0.21 | 0.23 | 1.07 | 0.2622 |
| Sodium Acrylic acid/maleic acid co-polymer (70/30) | 0.40 | 2.61 | 2.5 | 2.00 | 1.75 |
| Sodium polyacrylate (Sokalan PA30 CL) | | | 0.0055 | 0.011 | 0.008 |
| Terephthalate polymer | | | | 0.231 | |
| Polyethylene glycol/vinyl acetate random graft co polymer | 0.55 | 1.40 | 0.911 | 0.8924 | 0.911 |
| Photobleach- zinc phthalocyanine tetrasulfonate | | | | | |
| C.I. Fluorescent Brightener 260 | 0.1174 | 0.048 | 0.1455 | 0.2252 | 0.1455 |
| C.I. Fluorescent Brightener 351 (Tinopal ® CBS) | | 0.1049 | | | |
| Suds suppressor granule | | | 0.04 | 0.0658 | 0.04 |
| Hyrdophobically modified carboxy methyl cellulose (Finnifix ® SH-1) | | | | | |
| Bentonite | | | | | |
| Miscellaneous (Dyes, perfumes, process aids, moisture and sodium sulphate) | Balance | Balance | Balance | Balance | Balance |

TABLE G

Additional Granular Laundry Detergent Compositions and Their Components

| Component | Detergent Composition | | | |
|---|---|---|---|---|
| | 36k | 36l | 36m | 36n |
| Surfactants | | | | |
| $C_{10}$ Nonionic | 0.1979 | 0.1979 | 0.1979 | 0.1979 |
| $C_{16-17}$ Branched alkyl sulfate | | | | |
| $C_{12-14}$ alkyl sulphate | | | | |
| Sodium linear alkylbenzenesulfonate with aliphatic chain length $C_{11}$-$C_{12}$ | 8.92 | 8.92 | 11.5 | 11.5 |

TABLE G-continued

Additional Granular Laundry Detergent Compositions and Their Components

| Component | 36k | 36l | 36m | 36n |
|---|---|---|---|---|
| Sodium $C_{14/15}$ alcohol ethoxy-3-sulfate | 1.62 | 1.62 | 1.125 | 1.125 |
| Sodium $C_{14/15}$ alkyl sulphate | | | | |
| $C_{14/15}$ alcohol ethoxylate with average 7 moles of ethoxylation | 1.0 | 1.0 | 1.5 | 1.5 |
| mono-$C_{8-10}$ alkyl mono-hydroxyethyl di-methyl quaternary ammonium chloride | | | | |
| Di methyl hydroxyl ethyl lauryl ammonium chloride | | | | |
| Zeolite A | 1.63 | 1.63 | 2.0 | 2.0 |
| Sodium Silicate 1.6.ratio | 4.75 | 4.75 | 4.75 | 4.75 |
| Sodium Silicate 2.0.ratio | | | 0.06 | 0.06 |
| Sodium Silicate 2.35.ratio | | | | |
| Citric Acid | 1.10 | 1.10 | 1.1 | 1.1 |
| Sodium tripolyphosphate | | | | |
| Sodium Carbonate | 23.3 | 23.3 | 23.3 | 23.3 |
| Nonanoyloxybenzenesuplhonate | | | | |
| Oxaziridinium-based bleach booster | 0.021 | 0.021 | 0.015 | 0.015 |
| Tetrasodium S,S,-ethylenediaminedisuccinate | 0.26 | 0.26 | 0.26 | 0.26 |
| Diethylenetriamine penta (methylene phosphonic acid), heptasodium salt | | | | |
| Hydroxyethane dimethylene phosphonic acid | 0.47 | 0.47 | 0.47 | 0.47 |
| Ethylene diamine tetraacetate | | | | |
| MgSO4 | 0.83 | 0.83 | 0.82 | 0.82 |
| Sodium Percarbonate | 19.35 | 19.35 | 19.35 | 19.35 |
| Tetra Acetyl Ethylene Diamine | 4.51 | 4.51 | 4.51 | 4.51 |
| Sodium Perborate Monohydrate | | | | |
| Carboxymethyl cellulose (e.g. Finnfix BDA ex CPKelco) | 1.01 | 1.01 | 1.01 | 1.01 |
| Sodium Acrylic acid/maleic acid co-polymer (70/30) | 1.84 | 1.84 | 1.84 | 1.84 |
| Sodium polyacrylate (Sokalan PA30 CL) | 0.007 | 0.007 | 0.005 | 0.005 |
| Terephthalate polymer | 0.179 | 0.179 | 0.179 | 0.179 |
| Polyethylene glycol/vinyl acetate random graft co polymer | 0.96 | 0.96 | 0.96 | 0.96 |
| Photobleach- zinc phthalocyanine tetrasulfonate | | | | |
| C.I. Fluorescent Brightener 260 | 0.153 | 0.153 | 0.171 | 0.171 |
| C.I. Fluorescent Brightener 351 (Tinopal ® CBS) | | | | |
| Suds suppressor granule | 0.042 | 0.042 | 0.042 | 0.042 |
| Hyrdophobically modified carboxy methyl cellulose (Finnifix ® SH-1) | | | | |
| Bentonite | | | | |
| Miscellaneous (Dyes, perfumes, process aids, moisture and sodium sulphate) | Balance | Balance | Balance | Balance |

Notes for detergent compositions 36a-n in Tables E, F, G:

Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®).

Zeolite can be obtained from Industrial Zeolite (UK) Ltd, Grays, Essex, UK.

Citric acid and sodium citrate can be obtained from Jungbunzlauer, Basel, Switzerland.

Sodium percarbonate, sodium carbonate, sodium bicarbonate and sodium sesquicarbonate can be obtained from Solvay, Brussels, Belgium.

Acrylate/maleate copolymers can be obtained from BASF, Ludwigshafen, Germany.

Carboxymethylcellulose and hydrophobically modified carboxymethyl cellulose can be obtained from CPKelco, Arnhem, The Netherlands.

C.I. Fluorescent Brightener 260 can be obtained from 3V Sigma, Bergamo, Italy as Optiblanc® Optiblanc® 2M/G, Optiblanc® 2 MG/LT Extra, or Optiblanc® Ecobright.

Tetrasodium S,S-ethylenediamine disuccinate can be obtained from Innospec, Ellesmere Port, UK.

Terephthalate co-polymer can be obtained from Clariant under the tradename Repelotex SF 2. 1-Hydroxyethane-1,1-diphosphonic acid can be obtained from Thermphos, Vlissingen-Oost, The Netherlands.

Oxaziridinium-based bleach booster has the following structure, where R1=2-butyloctyl, and was produced according to US 2006/0089284A1.

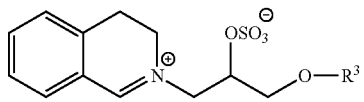

Enzymes Natalase®, Termamyl®, Stainzyme Plus®, Celluclean® and Mannaway®, can be obtained from Novozymes, Bagsvaerd, Denmark.

Zinc phthalocyanine tetrasulfonate can be obtained from Ciba Specialty Chemicals, Basel, Switzerland, as Tinolux® BMC.

Suds suppressor granule can be obtained from Dow Corning, Barry, UK.

Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.

EXAMPLE 1

Methods

The following assays are standard assays used in the examples described below. Occasionally specific protocols call for deviations from these standard assays. In those cases, deviations from these standard assay protocols below are identified in the examples.

A. Performance Index

The performance index (PI) of an enzyme compares the performance of the variant (measured value) and the standard enzyme (theoretical value or measured value) at the same protein concentration. In addition, the theoretical values can be calculated, using the parameters of the Langmuir equation of the standard enzyme.

A performance index (PI) that is greater than 1 (PI>1) indicates improved performance by a variant as compared to the standard (e.g., TLL, SEQ ID NO:2), while a PI of 1 (PI=1) identifies a variant that performs the same as the standard, and a PI that is less than 1 (PI<1) identifies a variant that performs worse than the standard.

B. Hydrolysis of p-Nitrophenyl Esters Assay

The TLL variants are assayed for lipase activity on three different para-nitrophenyl (pNP) ester substrates of varying alkyl chain lengths to determine the chain length preference of TLL variants. Table 1-1 provides details of the pNP ester substrates.

TABLE 1-1 pNP Ester Substrates

| Substrate | Abbr | Chain-length | Source |
|---|---|---|---|
| p-nitrophenyl butyrate | pNPB | C4 | Sigma (CAS 2635-84-9) |
| p-nitrophenyl caprylate (octanoate) | pNPO | C8 | Fluka (CAS 1956-10-1) |
| p-nitrophenyl palmitate | pNPP | C16 | Sigma (CAS 1492-30-4) |

A reaction emulsion with pNP ester substrates is prepared using 0.8 mM pNP ester pre-suspended in ethanol (5%) in 0.05 M HEPES adjusted to pH 8.2 or in 0.05 M MES, adjusted to pH 6.0.

The pNP-ester/buffer suspensions are mixed and transferred to a 96-well microtiter plate (MTP) containing the enzyme sample, in a total volume of 200 µL. Dilution of the enzyme samples and their transfer volumes are adjusted to keep the reaction within a linear range. The generation of liberated pNP is monitored over a period of 3 minutes at $OD_{405}$ nm and corrected using blank values (no enzyme). The pNP product generated per second is calculated using a pNP standard curve and then normalized to the added enzyme sample in the well (µmol pNP/s per added mg enzyme). When using the p-nitrophenyl caprylate at pH 6.0 pNP-ester/buffer suspensions are mixed and transferred to a 96-well microtiter plate (MTP) containing the enzyme sample, in a total volume of 150 µL. The plates are sealed and shaken for 10 minutes at 900 rpm at 25° C. in an iEMS shaker (Thermo scientific). After incubation 50 µl of 0.2M HEPES pH8.2 including 0.5% Triton X-100 is added. The generation of liberated pNP is read at $OD_{405}$ nm and corrected using blank values (no enzyme).

The performance index for hydrolysis is determined by comparing the hydrolysis of the variant enzyme on a particular pNP ester substrate with that of the TLL enzyme (SEQ ID NO:2).

C. Detergent Stability Assay

Accelerated detergent stability of the TLL variants is monitored by stressing the variants in a 10% (v/v) solution of the heavy duty liquid (HDL) detergent known commercially as Tide coldwater liquid (P&G, US; heat treated) at elevated temperature.

The raw ferment of the lipases are diluted 50× with 10% (v/v) solution of Tide coldwater liquid in a 96-well PCR plate. Following mixing, 7.5 µl is transferred to 96 well plate wells containing 192.5 µL pNP octanoate substrate and activity is measured as described in B to generate the unstressed value.

The PCR plate is sealed and incubated in a PCR machine for 30 min at 41° C. After end incubation the plate is cooled 3 min at 4° C. prior to measuring activity again. Activity of the variant enzymes is determined by transferring 15 ul of the incubated mixtures to a 96 well plate containing 185 µl of pNP octanoate/buffer suspension, and activity is measured as described in section B to generate the stressed value.

The performance index for detergent stability is determined by comparing the activity ratio of stressed vs. unstressed for the variant enzyme with that of the TLL enzyme SEQ ID NO:2).

D. Thermostability Assay

Accelerated thermostability of the TLL variants is monitored by stressing the variants in 50 mM HEPES, pH 8.2, with 1 ppm subtilisin BPN'-Y217L protease at elevated temperature. 80 µL of 50 mM HEPES, pH 8.2 with protease is transferred to 96-well PCR plate wells containing 20 µL of the enzyme sample. Following mixing, activity of the variant enzymes is determined by transferring 2 µl of the buffer/lipase mixtures to a 96 well plate containing 198 µl of pNP octanoate/buffer suspension, and activity is measured as described in section B.

The PCR plate is sealed and incubated in a PCR machine for 30 min at 64° C. After incubation the plate is cooled at 4° C. for 3 min prior to measuring activity. Activity of the variant enzymes is determined by transferring 4 ul of the incubated mixtures to a 96 well plate containing 196 µl of pNP octanoate/buffer suspension, activity is measured as described in section B.

A thermostability activity ratio is calculated based on enzyme activity after heating, divided by enzyme activity before heating, and is expressed as percentage remaining activity. The performance index for accelerated thermostability is determined by comparing the activity ratio of the variant enzyme, with that of the similarly treated TLL enzyme (SEQ ID NO:2).

D. LAS-Stability Assay

Accelerated LAS (linear alkylbenzene sulphonate, specifically sodium dodecyl benzene sulphonate, Sigma Cat. No. 289957) stability of the TLL variants is monitored by stressing the variants in 0.1% LAS diluted in HEPES buffer, pH 8.

80 µL of 0.1% LAS (w/v) at pH 8.2 is transferred to 96-well PCR plate wells containing 20 µL of the enzyme sample. Following mixing, activity of the variant enzymes is determined by transferring 2 ul of the buffer/lipase mixtures to a 96 well plate containing 198 µl of pNP octanoate/buffer suspension, and activity is measured as described in section B.

The PCR plate is sealed and incubated in a PCR machine for 30 min at 25° C. After incubation the plate is cooled at 4° C. for 3 min prior to measuring activity. Activity of the variant enzymes is determined by transferring 4 µl of the incubated mixtures to a 96 well plate containing 196 µl of pNP octanoate/buffer suspension, activity is measured as described in section B.

A LAS-stability activity ratio is calculated based on enzyme activity after incubation in LAS, divided by enzyme activity in the absence of LAS, and is expressed as percentage remaining activity. The performance index for LAS-stability is determined by comparing the activity ratio of the variant enzyme, with that of the similarly treated TLL enzyme SEQ ID NO:2).

E. CS-61 Microswatch Assay

Cleaning performance of the lipase variants is tested in a microswatch assay. CS-61 swatches, which are pre-stained cotton swatches stained with beef fat and a red dye (Center for Testmaterial, CFT, The Netherlands) are used in a 96-well plate format. Swatches are cut into 5 mm diameter pieces and placed in each well of the MTP. The performance of the lipase variants are tested in three detergent backgrounds, full dosage Tide coldwater liquid (heat treated for three hours at 95° C., final dosage: 0.92 g/l), half dose Tide coldwater liquid (heat treated for three hours at 95° C., final dosage: 0.46 g/l) and half dose Tide coldwater liquid (heat treated for three hours at 95° C.), plus adjuvant (n-dodecyl-β-D-Maltopyranoside) (final dosage detergent: 0.46 g/L, adjuvant: 0.272 µM).

Samples of lipase variants to be tested are obtained from Millipore filtered culture broth of cultures grown in MTP plates. The buffers used are 20 mM HEPES (final concentration) pH 8.2 and the water hardness is adjusted to 6 gpg 2:1 Ca:Mg.

A volume of 247.5 µl of the HDL detergent solution (described above) is added to each swatch-containing well of the 96-well plate. To initiate the reaction, enzyme samples are added at a volume of 3.5 µL into each well. The plates are sealed and shaken for 30 minutes at 900 rpm at 30° C. in an iEMS shaker (Thermo scientific). After incubation, the fabrics are rinsed 3 times with de-ionized water using a Hydrospeed plate washer (Tecan, Austria) and dried at 50° C. over night. Stain removal is quantified using RGB measurements of the rinsed and dried fabrics, taken with a scanner (MiCrotek Scan Maker 900). Images are imported into Photoshop CSII where RGB values are extracted from the swatch containing areas using IPTK 5.0 from Reindeer Graphics. Percent Soil removal (SRI) values of the washed fabric are calculated in relation to the unwashed fabrics using the formula:

$$\% \text{ Soil Removal } (SRI) = (\Delta E / \Delta E_{initial}) * 100$$

Where $$\Delta E = \sqrt{(R_{after} - R_{before})^2 + (G_{after} - G_{before})^2 + (B_{after} - B_{before})^2}$$

Where $$\Delta E_{initial} = \sqrt{(R_{white} - R_{before})^2 + (G_{white} - G_{before})^2 + (B_{white} - B_{before})^2}$$

The performance index for cleaning performance is calculated by comparing the SRI of the variant enzyme with the SRI of the TLL standard enzyme (SEQ ID NO:2) at the same enzyme dose as the variant. A Langmuir fit is used to calculate what the SRI for the TLL would be at the same enzyme dose as the variant.

F. Detergents

Commercially available detergent is used:
Tide coldwater liquid (P&G). Purchased commercially August 2010 and heat treated (three hours at 95° C.) to inactivate enzymes in the product formulation.

G. Protein Determination Assay

The protein concentration of TLL variants is determined for filtered ferment broth of cultures grown in MTP plates using a fluorescent excitation transfer immunoassay. Fluorescein-labeled TLL antigen is mixed with rhodamine-labeled anti-TLL rabbit antibody at an antigen-antibody ratio where fluorescein emission is quenched. When added to the mixture, TLL variant protein will compete for binding to the labeled anti-TLL antibody leading to an increase in fluorescein emission. The increase in fluorescein emission is directly proportional to the TLL variant protein concentration.

20 µl of TLL variant filtered ferment broth is transferred to a black, flat bottom, 96-well plate containing 140 µl phosphate buffered saline and mixed. 20 µl each of fluorescein-labeled TLL and rhodamine-labeled anti-TLL rabbit antibody are then transferred to the plate and mixed. Following 30 minute incubation in the dark at room temperature, the fluorescence of each well is measured using an excitation wavelength of 495 nm and an emission wavelength of 520 nm. A linear fit of fluorescein emission for TLL enzyme standards (SEQ ID NO:2) was used to determine the protein concentration for each TLL variant.

EXAMPLE 2

Cloning and Expression in *Bacillus subtilis* of Lipase-3 from *Thermomyces Lanuginosus*

The *Thermomyces lanuginosus* Lipase-3 (TLL) corresponds to Family abH23.01, *Rhizomucor mihei* lipase like (Lipase Engineering Database) with the amino acid sequence of the mature lipase set forth as PDB: 1DT3.

A TLL synthetic gene (SEQ ID NO. 1) was designed for expression in *B. subtilis* based on the amino acid sequence of TLL. The TLL gene was subcloned into a replicating pBN based *Bacillus* expression vector as a BmtI-HindIII fragment, which contains the aprE promoter, aprE signal sequence and BPN' subtilisin gene (*B. amyloliquefaciens*) terminator (Babe et al. (1998), Biotechnol. Appl. Biochem. 27: 117-124). Ligation of this vector with the synthetic gene resulted in the fusion of the N-terminus of the TLL polypeptide to the third amino acid of the *B. subtilis* AprE pro-peptide encoded by the expression vector (in the pBN based vector, the -2 amino acid in the signal peptide was previously mutagenized to introduce the BmtI site). Following the natural signal peptidase cleavage in the host, the recombinant TLL protein produced in this manner has three additional amino acids (Ala-Gly-Lys) at its amino-terminus. The predicted signal cleavage site was determined by the Signal P 3.0 program, set to Signal P-NN system, (Emanuelsson et al., (2007), Nature Protocols, 2: 953-971).

For expression of the TLL gene in *B. subtilis*, a pHY300PLK based vector (Takara) was used with a transcriptional terminator introduced after the tetracycline gene by ligating an oligonucleotide cassette (5'-GTTACCTT-GAATGTATATAAACATTCTCAAAGGGAT-TTCTAATAAAAAACGCTCGGTTGCCG CCGGGCGTTTTTTATGCATCGATGG (SEQ ID NO: 5) annealed with 5'-AATTCCATCGATGCAT-AAAAAACGCCCGGCGGCAACCGAGCGTTTTTTATT-AGAAATCCCTT TGAGAATGTTTATATACATTCAAG (SEQ ID NO: 6)) into the BstEII and EcoRI sites of a pHY300PLK based vector.

Figure 2:
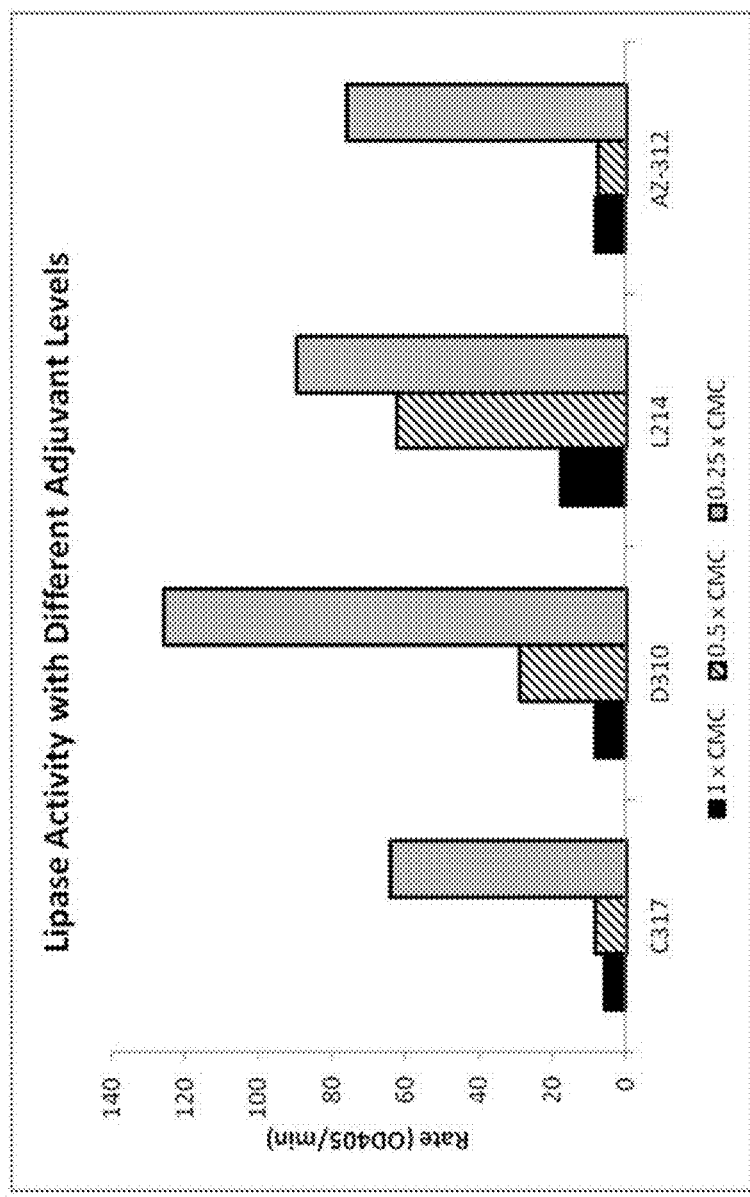
FIG. 2 shows lipase activity in the TLL lipase enzyme with different adjuvant levels.

The entire TLL expression cassette from the pBN based vector was then cloned as an EcoRI-BamHI fragment into the EcoRI and HindIII sites of this pHY300PLK based vector using a BamHI-HindIII linker (5-GATCCTGACTGCCTG (SEQ ID NO: 7) annealed with 5'-AGCTCAGGCAGTCAG (SEQ ID NO: 8)) that after cloning eliminates the original HindIII site in the pHY300PLK based vector. The resulting vector was called pHYT-TLLwt (FIG. 2-1).

SEQ ID NO: 1 sets forth the nucleotide sequence of the synthetic TLL gene

GCTAGCGCAGCTGGCAAAGAAGTTAGCCAAGATCTGTTCAACCAATT

CAACCTTTTCGCTCAATACTCTGCAGCTGCTTACTGCGGAAAGAACA

ACGATGCACCTGCTGGTACTAACATCACTTGCACAGGTAACGCATGT

CCTGAAGTAGAAAAAGCTGATGCTACATTTCTTTACTCTTTTGAAGA

TAGCGGCGTCGGCGATGTTACCGGTTTCTTAGCTCTGGATAACACAA

ACAAACTTATCGTCCTTAGCTTCAGAGGCTCTCGCTCAATCGAAAAC

TGGATCGGTAACCTTAATTTTGACTTGAAAGAAATCAACGATATCTG

CTCTGGTTGCCGTGGCCATGACGGATTCACATCATCTTGGAGAAGCG

TCGCAGACACGCTTCGCCAAAAAGTAGAAGATGCCGTACGCGAACAC

CCAGATTACAGAGTAGTTTTCACAGGTCACTCTCTTGGCGGAGCTTT

AGCAACAGTAGCAGGCGCTGATCTCCGCGGTAACGGATACGACATTG

ATGTCTTCTCTTACGGCGCTCCGCGCGTCGGTAACAGAGCGTTTGCT

GAATTTTTAACTGTACAAACAGGCGGAACTCTTTATCGCATCACTCA

CACAAACGATATTGTCCCGCGCTTACCTCCGAGAGAATTTGGTTACT

CACACAGCTCTCCTGAATACTGGATCAAAAGCGGTACATTGGTACCT

GTTACTCGAAACGATATCGTCAAAATTGAAGGAATTGACGCCACCGG

CGGCAACAACCAACCGAACATCCCTGACATCCCGGCACACCTTTGGT

ACTTCGGCTTAATCGGAACATGCCTTTAAAAGCTT

SEQ ID NO:2 sets forth the amino acid sequence of TLL produced from expression plasmid pHYT-TLLwt (AprE signal sequence is underlined, cleavage site as predicted by Signal P):

MRSKKLWISLLFALTLIFTMAFSNMSASAAGKEVSQDLFNQFNLFAQ

YSAAAYCGKNNDAPAGTNITCTGNACPEVEKADATFLYSFEDSGVGD

VTGFLALDNTNKLIVLSFRGSRSIENWIGNLNFDLKEINDICSGCRG

HDGFTSSWRSVADTLRQKVEDAVREHPDYRVVFTGHSLGGALATVAG

ADLRGNGYDIDVFSYGAPRVGNRAFAEFLTVQTGGTLYRITHTNDIV

PRLPPREFGYSHSSPEYWIKSGTLVPVTRNDIVKIEGIDATGGNNQP

NIPDIPAHLWYFGLIGTCL

SEQ ID NO: 3 sets forth the amino acid sequence of the TLL mature protein produced from expression plasmid pHYT-TLLwt with a three amino acid amino-terminal extension:

AGKEVSQDLFNQFNLFAQYSAAAYCGKNNDAPAGTNITCTGNACPEV

EKADATFLYSFEDSGVGDVTGFLALDNTNKLIVLSFRGSRSIENWIG

NLNFDLKEINDICSGCRGHDGFTSSWRSVADTLRQKVEDAVREHPDY

RVVFTGHSLGGALATVAGADLRGNGYDIDVFSYGAPRVGNRAFAEFL

TVQTGGTLYRITHTNDIVPRLPPREFGYSHSSPEYWIKSGTLVPVTR

NDIVKIEGIDATGGNNQPNIPDIPAHLWYFGLIGTCL

SEQ ID NO: 4 sets forth the amino acid sequence of the TLL mature protein based on the naturally occurring gene sequence:

EVSQDLFNQFNLFAQYSAAAYCGKNNDAPAGTNITCTGNACPEVEKA

DATFLYSFEDSGVGDVTGFLALDNTNKLIVLSFRGSRSIENWIGNLN

FDLKEINDICSGCRGHDGFTSSWRSVADTLRQKVEDAVREHPDYRVV

FTGHSLGGALATVAGADLRGNGYDIDVFSYGAPRVGNRAFAEFLTVQ

TGGTLYRITHTNDIVPRLPPREFGYSHSSPEYWIKSGTLVPVTRNDI

VKIEGIDATGGNNQPNIPDIPAHLWYFGLIGTCL

EXAMPLE 3

Generation of TLL Site Evaluation Libraries

Site evaluation libraries (SELs) were created by GENEART using a proprietary process (WO 2004/059556A3) and the manufacture of DNA molecules utilized technology owned by or licensed to GENEART (European Patent Nos. 0 200 362 and 0 201 184; and U.S. Pat. Nos. 4,683,195, 4,683,202 and 6,472,184). The construction of TLL SELs described in this example was performed by GENEART using their technology platform for library generation under proprietary GENEART know-how and/or intellectual property. The sequential permutation approach of GENEART, to produce SELs, is described in general on the company's web site.

The pHYT-TLLwt plasmid DNA served as template to produce SELs at all of the sites in the native TLL mature region (SEQ ID NO: 4). First three amino acids (Ala-Gly-Lys) from the AprE pro-region in the recombinant TLL protein (SEQ ID NO: 3) were not mutagenized. GENEART was commissioned to create the SELs at all of the native TLL positions using their standard protocols (numbering starts from the first amino acid of the native TLL mature protein). The positional library for each of the 269 residues constructed by GENEART contained approximately 16 amino acid substitutions per site. The libraries consisted of transformed *B. subtilis* cells containing the expression plasmid encoding TLL variant sequences at the 269 positions described. GENEART provided the libraries as 96 well plates, one variant per well, with the cultures frozen in glycerol.

The *B. subtilis* transformants containing TLL substitution variants were cultured in 96 well plates for 16 hours in Tryptic Soy Broth (TSB) with 10 mg/L tetracycline, and 10 µl of this pre-culture was added to Corning 3599 MTP's filled with 190 µl of MBD Medium (described below) supplemented with 25 mg/L tetracycline. The plates were incubated for 60-65 hours at 37° C. at 80% humidity with constant rotational mixing at 300 rpm. Cells were harvested by centrifugation at 2500 rpm for 10 minutes and filtered through Millipore Multiscreen filterplate using a Millipore vacuum system. The culture supernatants were used for assays. The cultivation medium (MBD Medium) was an enriched semi-defined medium based on MOPs buffer, with urea as major nitrogen source, glucose as the main carbon source, and supplemented with 1% soytone for robust cell growth.

EXAMPLE 4

Productive Positions and Combinable Mutations

Productive positions are described as those positions within a molecule that are most useful for making combinatorial variants exhibiting an improved characteristic, where the position itself allows for at least one combinable mutation. Combinable mutations can be described as those substitutions in a molecule that can be used to make combinatorial variants. Combinable mutations are ones that improve at least one desired property of the molecule, while not significantly decreasing either: expression, activity, or stability.

Combinable mutations are ones that improve at least one desired property of the molecule while not significantly decreasing either: expression, activity, or stability. Combinable mutations in TLL polypeptide were determined using performance index (PI) values resulting from the assays described in Example 1: CS-61 micro-swatch assay, hydrolysis of p-nitrophenyl esters, stability in detergents, stability in LAS, and thermostability.

Combinable mutations have been grouped according to the following criteria:

A variant where the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.9, and in addition have a PI for any one of these tests that is greater than or equal to 1.0 (Group A).

A variant where the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.8, and in addition have a PI for any one of these tests that is greater than or equal to 1.2 (Group B).

A variant where the minimum performance indices (PI) relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.5, and in addition have a PI for any one of these tests that is greater than or equal to 1.5 (Group C).

Groups A, B, and C further contain amino acid positions that have differing degrees of tolerance for multiple substitutions. To identify productive positions, we measure the degree of substitutions tolerated at each position, and assign a Productivity Score to each position. The Productivity Score was assigned according to the percentage of substitutions within each position that fall within groups A, B, or C, using the criteria set forth below.

Productive positions are defined as the positions which have shown a certain degree of tolerance for multiple substitutions, while at the same time meeting a set of criteria for combinability as set forth below.

The criteria to determine the Productivity Score for productive positions are as follows:

Positions where 50% or more of the substitutions at a given position fall within groups A, B, or C are given a Productivity Score of "4". These positions include 1, 2, 3, 4, 5, 6, 8, 9, 13, 23, 24, 25, 26, 27, 28, 29, 33, 37, 38, 39, 46, 51, 52, 54, 58, 64, 66, 68, 69, 71, 72, 75, 90, 93, 94, 111, 120, 122, 123, 130, 131, 137, 140, 162, 163, 189, 250, 252, and 264.

Positions where less than 50%, but greater than, or equal to 30% of the substitutions at a given position fall within groups A, B, or C are given a Productivity Score of "3". These positions include 18, 19, 20, 30, 31, 32, 47, 48, 49, 50, 53, 56, 60, 73, 74, 85, 86, 91, 95, 96, 97, 98, 99, 101, 105, 108, 115, 125, 127, 128, 132, 133, 151, 159, 164, 179, 183, 187, 188, 190, 216, 223, 232, 237, 244, 251, 254, 263, 267, and 269.

Positions where less than 30%, but greater than, or equal to 15% of the substitutions at a given position fall within groups A, B, or C are given a Productivity Score of "2". These positions include
7, 11, 12, 15, 22, 35, 40, 42, 43, 44, 45, 61, 63, 65, 67, 76, 77, 84, 87, 114, 117, 119, 121, 134, 135, 136, 143, 154, 155, 156, 158, 165, 166, 168, 176, 180, 191, 199, 200, 202, 209, 211, 214, 217, 221, 224, 225, 228, 229, 231, 233, 248, 249, 253, 255, 256, 265, and 268.

Positions where less than 15% of the substitutions at a given position fall within groups A, B, or C are given a Productivity Score of "1". These positions include 14, 16, 17, 34, 41, 55, 57, 59, 62, 70, 79, 92, 100, 102, 103, 106, 109, 110, 112, 118, 126, 138, 139, 142, 149, 152, 153, 167, 169, 170, 181, 184, 192, 193, 196, 198, 205, 206, 208, 210, 212, 213, 218, 226, 227, 230, 236, 238, 239, 242, 243, 246, 257, 259, 260, 262, and 266.

Productive positions in TLL that fall within the previously described Productivity Scores of "1, 2, 3, and 4" are listed below. Position numbering based on mature TLL listed in SEQ ID NO. 3.
1, 2, 3, 4, 5, 6, 7, 8, 9, 11, 12, 13, 14, 15, 16, 17, 18, 19, 20, 22, 23, 24, 25, 26, 27, 28, 29, 30, 31, 32, 33, 34, 35, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 79, 84, 85, 86, 87, 90, 91, 92, 93, 94, 95, 96, 97, 98, 99, 100, 101, 102, 103, 105, 106, 108, 109, 110, 111, 112, 114, 115, 117, 118, 119, 120, 121, 122, 123, 125, 126, 127, 128, 130, 131, 132, 133, 134, 135, 136, 137, 138, 139, 140, 142, 143, 149, 151, 152, 153, 154, 155, 156, 158, 159, 162, 163, 164, 165, 166, 167, 168, 169, 170, 176, 179, 180, 181, 183, 184, 187, 188, 189, 190, 191, 192, 193, 196, 198, 199, 200, 202, 205, 206, 208, 209, 210, 211, 212, 213, 214, 216, 217, 218, 221, 223, 224, 225, 226, 227, 228, 229, 230, 231, 232, 233, 236, 237, 238, 239, 242, 243, 244, 246, 248, 249, 250, 251, 252, 253, 254, 255, 256, 257, 259, 260, 262, 263, 264, 265, 266, 267, 268, and 269.

Productive positions in TLL that fall within the previously described Productivity Scores of "2, 3, and 4" are listed below. Position numbering based on mature TLL listed in SEQ ID NO. 3.

1, 2, 3, 4, 5, 6, 7, 8, 9, 11, 12, 13, 15, 18, 19, 20, 22, 23, 24, 25, 26, 27, 28, 29, 30, 31, 32, 33, 35, 37, 38, 39, 40, 42, 43, 44, 45, 46, 47, 48, 49, 50, 51, 52, 53, 54, 56, 58, 60, 61, 63, 64, 65, 66, 67, 68, 69, 71, 72, 73, 74, 75, 76, 77, 84, 85, 86, 87, 90, 91, 93, 94, 95, 96, 97, 98, 99, 101, 105, 108, 111, 114, 115, 117, 119, 120, 121, 122, 123, 125, 127, 128, 130, 131, 132, 133, 134, 135, 136, 137, 140, 143, 151, 154, 155, 156, 158, 159, 162, 163, 164, 165, 166, 168, 176, 179, 180, 183, 187, 188, 189, 190, 191, 199, 200, 202, 209, 211, 214, 216, 217, 221, 223, 224, 225, 228, 229, 231, 232, 233, 237, 244, 248, 249, 250, 251, 252, 253, 254, 255, 256, 263, 264, 265, 267, 268, and 269.

Productive positions in TLL that fall within the previously described Productivity Scores of "3 and 4" are listed below. Position numbering based on mature TLL listed in SEQ ID NO. 3.

1, 2, 3, 4, 5, 6, 8, 9, 13, 18, 19, 20, 23, 24, 25, 26, 27, 28, 29, 30, 31, 32, 33, 37, 38, 39, 46, 47, 48, 49, 50, 51, 52, 53, 54, 56, 58, 60, 64, 66, 68, 69, 71, 72, 73, 74, 75, 85, 86, 90, 91, 93, 94, 95, 96, 97, 98, 99, 101, 105, 108, 111, 115, 120, 122, 123, 125, 127, 128, 130, 131, 132, 133, 137, 140, 151, 159, 162, 163, 164, 179, 183, 187, 188, 189, 190, 216, 223, 232, 237, 244, 250, 251, 252, 254, 263, 264, 267, and 269.

Productive positions in TLL that fall within the previously described Productivity Scores of "4" are listed below. Position numbering based on mature TLL listed in SEQ ID NO. 3.

1, 2, 3, 4, 5, 6, 8, 9, 13, 23, 24, 25, 26, 27, 28, 29, 33, 37, 38, 39, 46, 51, 52, 54, 58, 64, 66, 68, 69, 71, 72, 75, 90, 93, 94, 111, 120, 122, 123, 130, 131, 137, 140, 162, 163, 189, 250, 252, and 264.

The productive positions in TLL that fall within the previously described Productivity Scores of "1, 2, 3, and 4" and the substitutions within those positions that are combinable are listed below. Position numbering based on mature TLL listed in SEQ ID NO. 3.

1(E,A,C,D,F,I,L,N,P,Q,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S,W,Y); 5(D,H,I,K,L,S,T,V,W,Y); 6(L,A,E,H,I,K,M,Q,T,V,Y); 7(F,H,M,V,Y); 8(N,A,E,G,H,I,K,L,M,T,V,W,Y); 9(Q,A,D,E,G,H,I,K,N,R,W,Y); 11(N,H,K,V,Y); 12(L,F,H,V,W); 13(F,A,H,K,M,N,Q,T,V,Y); 14(A,S,V); 15(Q,G,H,M,S); 16(Y,H,W); 17(S,E); 18(A,C,H,K,M,N,Q,S,W); 19(A,C,G,I,L,T,V,W); 20(A,G,I,P,Q,S,T); 22(C,H,L,M); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M,N,P,Q,R,S); 29(P,C,E,G,H,I,K,L,M,Q,R,S,T,V,W,Y); 30(A,D,H,L,N,R,V,W); 31(G,D,E,H,M,P,Q,S,V); 32(T,A,I,M,Q,R,S); 33(N,D,E,F,K,L,M,Q,R,S); 34(I,P); 35(T,E,K,R); 37(T,A,C,D,E,F,G,H,I,K,L,M,P,Q,R,W,Y); 38(G,A,D,E,F,H,I,K,L,M,NT,V,W,Y); 39(N,C,E,H,I,L,P,Q,S,T,V,W,Y); 40(A,F,M,S,W); 41(C,V); 42(P,C,G,I,V,W); 43(E,D,I,M,R,T); 44(V,H,I,T); 45(E,F,Q,V); 46(K,D,E,F,G,L,M,V,W); 47(A,D,E,F,H,M,T,W); 48(D,E,G,H,L,P,Q); 49(A,G,H,K,L,V,W); 50(T,A,D,F,K,L,R,S,W); 51(F,A,D,E,G,I,L,M,N,P,R,S,T,Y); 52(L,A,E,G,I,M,R,T,V,W); 53(Y,E,G,H,K,L,S,W); 54(S,E,F,G,H,K,M,P,R,T,V,W,Y); 55(F,G,W); 56(E,H,K,R,T,V); 57(D,S); 58(S,D,G,H,I,K,M,Q,R,W); 59(G,D); 60(V,G,K,L,Y); 61(G,A,D,L,R); 62(D,N); 63(V,K,Q,T); 64(T,C,D,E,G,I,K,L,N,R,V,Y); 65(G,L,V,Y); 66(F,A,G,H,I,L,M,N,Q,R,S,T,VW,Y); 67(L,H,I,Q,V); 68(A,C,G,I,S,T,V,W,Y); 69(L,A,D,G,H,I,K,N,S,T,W); 70(D,S); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T,V,Y); 76(I,H,S,V); 77(V,A,I,L,N,T); 79(S,A,M); 84(R,H,Q,W); 85(S,F,H,I,N,Q,T); 86(I,L,M,P,Q,T,V,Y); 87(E,A,D,G,P,V); 90(I,A,E,F,N,Q,T,V,Y); 91(G,E,F,H,I,M,Q,R); 92(N,A,T); 93(L,D,H,I,K,N,P,Q,R,V,W); 94(N,D,G,K,M,P,R,S,T,V); 95(F,G,H,K,L,Q,T,V,W); 96(D,A,K,P,R,V); 97(L,A,D,I,M,Q,T); 98(K,D,E,H,I,M,Q); 99(E,D,K,P,Q,S,T,W); 100(I,M); 101(N,C,D,E,H,M,Y); 102(D,H); 103(I,Y); 105(S,A,D,E,F,K,P,W); 106(G,H); 108(R,E,F,K,M,Q,Y); 109(G,T); 110(H,N,S); 111(D,A,E,F,L,Q,T,V,W); 112(G,F,Q); 114(T,F,I,M,V); 115(S,G,I,L,M,N,R,T,V); 117(W,H,K,Q,V); 118(R,P); 119(S,D,I,Q,T,V); 120(V,G,H,I,N,S,W,Y); 121(A,K,Q); 122(D,A,E,F,H,I,N,S,T,Y); 123(T,E,G,I,K,L,M,N,Q,W); 125(R,C,G,I,N,Q,T,Y); 126(Q,I,M); 127(K,D,E,F,G,R,T); 128(V,C,H,I,L,N,S,W,Y); 130(D,A,C,E,F,G,H,Q,R,T,V,W,Y); 131(A,C,H,I,K,N,Q,R,S,T,W,Y); 132(V,C,D,H,I,K,Q,R,W); 133(R,E,F,I,N,Q,V); 134(E,L,P,V); 135(H,F,K,T); 136(P,D,Q,R); 137(D,A,E,F,G,H,I,K,L,M,N,P,Q,R,S,T,V,W,Y); 138(Y,F); 139(RLT); 140(V,C,E,F,I,L,M,N,Q,T); 142(F,H,Y); 143(T,A,G,N,S); 149(G,A); 151(L,I,M,N,P,T,V,W); 152(A,I,V); 153(T,S); 154(V,F,I,L,M,Y); 155(A,G,S,T); 156(G,F,M,T,W); 158(D,E,F,Y); 159(L,E,M,Q,R,W); 162(N,D,E,F,G,H,I,K,M,P,Q,R,S,Y); 163(G,A,F,L,M,N,P,R,S,W,Y); 164(Y,D,N,R,S,V); 165(D,I,P,Y); 166(I,D,G,W); 167(D,N); 168(V,G,L,Q); 169(F,S,Y); 170(S,G); 176(V,F,I,L,N,W); 179(R,E,H,I,K,L,Q,V); 180(A,D,K,Q,T); 181(F,L); 183(E,H,M,Q,S,T,V,Y); 184(F,W,Y); 187(V,G,H,L,N,Q,S,T,W); 188(Q,C,E,F,H,R,T); 189(T,D,E,G,K,M,N,Q,R,S,V); 190(G,D,H,R,S,Y); 191(G,F,L,V); 192(T,N,P); 193(L,T); 196(I,V); 198(H,G,S); 199(T,G,N,V); 200(N,A,P,S); 202(I,L,M,P,V); 205(R,D); 206(L,N); 208(P,E,N); 209(R,H,S,T); 210(E,S); 211(F,I,R,T,W); 212(G,Q); 213(Y,S); 214(S,A,D,M); 216(S,D,G,N,Q,V,W); 217(S,H,K,V); 218(P,T); 221(W,F,G,Y); 223(K,A,H,L,M,Q,S,T,V); 224(S,A,F,P); 225(G,C,E,K,R); 226(T,D,N); 227(L,C,H,M); 228(V,A,E,R); 229(P,I,K,M,S); 230(V,W); 231(T,G,H,K,L,M); 232(R,C,D,I,L,M,P,T,W); 233(N,D,G,H,Q); 236(V,W); 237(K,E,H,I,L,T,W,Y); 238(I,V); 239(E,K); 242(D,T); 243(A,S); 244(T,A,F,I,L,M,P,Q,S); 246(G,I); 248(N,D,L,Y); 249(Q,E,G,T); 250(P,D,E,G,K,Q,R,S,T); 251(N,D,M,Q,S,T,W,Y); 252(I,A,C,D,E,F,G,H,K,L,N,Q,R,S,T,W); 253(P,F,H,N,R); 254(D,A,H,K,N,P,T); 255(I,F,L,W); 256(P,A,D,S,T); 257(A,W,Y); 259(L,W,Y); 260(W,P); 262(F,D,K); 263(G,C,H,I,K,M,V); 264(L,C,E,G,H,M,N,P,Q,R,S,T); 265(I,L,M,Q,R,W); 266(G,E); 267(T,G,I,L,M,P,W); 268(C,D,H,N); and 269(L,D,F,M,Q,V,W).

The productive positions in TLL that fall within the previously described Productivity Scores of "2, 3, and 4" and the substitutions within those positions that are combinable are listed below. Position numbering based on mature TLL listed in SEQ ID NO. 3.

1(E,A,C,D,F,I,L,N,P,Q,R,S,T,V,W,Y); 2(V,F,G,H,I,K,L,M,P,T); 3(S,A,D,E,G,H,K,Q,R,T,Y); 4(Q,A,D,F,G,I,K,L,M,N,P,R,S,W,Y); 5(D,H,I,K,L,S,T,V,W,Y); 6(L,A,E,H,I,K,M,Q,T,V,Y); 7(F,H,M,V,Y); 8(N,A,E,G,H,I,K,L,M,T,V,W,Y); 9(Q,A,D,E,G,H,I,K,N,R,W,Y); 11(N,H,K,V,Y); 12(L,F,H,V,W); 13(F,A,H,K,M,N,Q,T,V,Y); 15(Q,G,H,M,S); 18(A,C,H,K,M,N,Q,S,W); 19(A,C,G,I,L,T,V,W); 20(A,G,I,P,Q,S,T); 22(C,H,L,M); 23(G,C,D,E,F,H,I,K,L,M,N,P,Q,R,S,T,V,W); 24(K,A,D,E,F,H,I,L,M,N,P,R,T,V,W,Y); 25(N,A,C,D,E,G,H,I,K,L,S,T,V,W); 26(N,C,G,K,L,M,Q,S,T,V,W,Y); 27(D,A,E,F,G,H,I,N,Q,R,S,T,V,Y); 28(A,D,E,F,G,H,I,L,M,N,P,Q,R,S); 29(P,C,E,G,H,I,K,L,M,Q,R,S,T,V,W,Y); 30(A,D,H,L,N,R,V,W); 31(G,D,E,H,M,P,Q,S,V); 32(T,A,I,M,Q,R,S);

33(N,D,E,F,K,L,M,Q,R,S); 35(T,E,K,R); 37(T,A,C,D,E,F, G,H,I,K,L,M,P,Q,R,W,Y); 38(G,A,D,E,F,H,I,K,L,M,NT,V, W,Y); 39(N,C,E,H,I,L,P,Q,S,T,V,W,Y); 40(A,F,M,S,W); 42(P,C,G,I,V,W); 43(E,D,I,M,R,T); 44(V,H,I,T); 45(E,F,Q, V); 46(K,D,E,F,G,L,M,V,W); 47(A,D,E,F,H,M,T,W); 48(D, E,G,H,L,P,Q); 49(A,G,H,K,L,V,W); 50(T,A,D,F,K,L,R,S, W); 51(F,A,D,E,G,I,L,M,N,P,R,S,T,Y); 52(L,A,E,G,I,M,R, T,V,W); 53(Y,E,G,H,K,L,S,W); 54(S,E,F,G,H,K,M,P,R,T, VW,Y); 56(E,H,K,R,T,V); 58(S,D,G,H,I,K,M,Q,R,W); 60(V,G,K,L,Y); 61(G,A,D,L,R); 63(V,K,Q,T); 64(T,C,D,E, G,I,K,L,N,R,V,Y); 65(G,L,V,Y); 66(F,A,G,H,I,L,M,N,Q,R, S,T,VW,Y); 67(L,H,I,Q,V); 68(A,C,G,I,S,T,V,W,Y); 69(L, A,D,G,H,I,K,N,S,T,W); 71(N,D,E,H,K,Q,R,S,T,V,W,Y); 72(T,A,D,E,F,H,I,K,L,N,P,R,S,V,Y); 73(N,E,G,H,K,R,S); 74(K,A,D,E,G,H,N,Q,S); 75(L,A,D,E,G,H,I,M,N,Q,R,S,T, V,Y); 76(I,H,S,V); 77(V,A,I,L,N,T); 84(R,H,Q,W); 85(S,F, H,I,N,Q,T); 86(I,L,M,P,Q,T,V,Y); 87(E,A,D,G,P,V); 90(I,A, E,F,N,Q,T,V,Y); 91(G,E,F,H,I,M,Q,R); 93(L,D,H,I,K,N,P, Q,R,V,W); 94(N,D,G,K,M,P,R,S,T,V); 95(F,G,H,K,L,Q,T, V,W); 96(D,A,K,P,R,V); 97(L,A,D,I,M,Q,T); 98(K,D,E,H, I,M,Q); 99(E,D,K,P,Q,S,T,W); 101(N,C,D,E,H,M,Y); 105 (S,A,D,E,F,K,P,W); 108(R,E,F,K,M,Q,Y); 111(D,A,E,F,L, Q,T,V,W); 114(T,F,I,M,V); 115(S,G,I,L,M,N,R,T,V); 117 (W,H,K,Q,V); 119(S,D,I,Q,T,V); 120(V,G,H,I,N,S,W,Y); 121(A,K,Q); 122(D,A,E,F,H,I,N,S,T,Y); 123(T,E,G,I,K,L, M,N,Q,W); 125(R,C,G,I,N,Q,T,Y); 127(K,D,E,F,G,R,T); 128(V,C,H,I,L,N,S,W,Y); 130(D,A,C,E,F,G,H,Q,R,T,V,W, Y); 131(A,C,H,I,K,N,Q,R,S,T,W,Y); 132(V,C,D,H,I,K,Q,R, W); 133(R,E,F,I,N,Q,V); 134(E,L,P,V); 135(H,F,K,T); 136 (P,D,Q,R); 137(D,A,E,F,G,H,I,K,L,M,N,P,Q,R,S,T,V,W,Y); 140(V,C,E,F,I,L,M,N,Q,T); 143(T,A,G,N,S); 151(L,I,M,N, P,T,V,W); 154(V,F,I,L,M,Y); 155(A,G,S,T); 156(G,F,M,T, W); 158(D,E,F,Y); 159(L,E,M,Q,R,W); 162(N,D,E,F,G,H, I,K,M,P,Q,R,S,Y); 163(G,A,F,L,M,N,P,R,S,W,Y); 164(Y,D, N,R,S,V); 165(D,I,P,Y); 166(I,D,G,W); 168(V,G,L,Q); 176 (V,F,I,L,N,W); 179(R,E,H,I,K,L,Q,V); 180(A,D,K,Q,T); 183(E,H,M,Q,S,T,V,Y); 187(V,G,H,L,N,Q,S,T,W); 188(Q, C,E,F,H,R,T); 189(T,D,E,G,K,M,N,Q,R,S,V); 190(G,D,H, R,S,Y); 191(G,F,L,V); 199(T,G,N,V); 200(N,A,P,S); 202(I, L,M,P,V); 209(R,H,S,T); 211(F,I,R,T,W); 214(S,A,D,M); 216(S,D,G,N,Q,V,W); 217(S,H,K,V); 221(W,F,G,Y); 223 (K,A,H,L,M,Q,S,T,V); 224(S,A,F,P); 225(G,C,E,K,R); 227 (L,C,H,M); 228(V,A,E,R); 229(P,I,K,M,S); 231(T,G,H,K,L, M); 232(R,C,D,I,L,M,P,T,W); 233(N,D,G,H,Q); 237(K,E, H,I,L,T,W,Y); 244(T,A,F,I,L,M,P,Q,S); 248(N,D,L,Y); 249 (Q,E,G,T); 250(P,D,E,G,K,Q,R,S,T); 251(N,D,M,Q,S,T,W, Y); 252(I,A,C,D,E,F,G,H,K,L,N,Q,R,S,T,W); 253(P,F,H,N, R); 254(D,A,H,K,N,P,T); 255(I,F,L,W); 256(P,A,D,S,T); 263(G,C,H,I,K,M,V); 264(L,C,E,G,H,M,N,P,Q,R,S,T); 265 (I,L,M,Q,R,W); 267(T,G,I,L,M,P,W); 268(C,D,H,N); and 269(L,D,F,M,Q,V,W).

The productive positions in TLL that fall within the previously described Productivity Scores of "3 and 4" and the substitutions within those positions that are combinable are listed below. Position numbering based on mature TLL listed in SEQ ID NO. 3.

1(E,A,C,D,F,I,L,N,PQ,R,S,T,V,W,Y); 2(V,F,G,H,I,K,L, M,P,T); 3(S,A,D,E,G,H,K,Q,R,T,Y); 4(Q,A,D,F,G,I,K,L,M, N,P,R,S,W,Y); 5(D,H,I,K,L,S,T,V,W,Y); 6(L,A,E,H,I,K,M, Q,T,V,Y); 8(N,A,E,G,H,I,K,L,M,T,V,W,Y); 9(Q,A,D,E,G, H,I,K,N,R,W,Y); 13(F,A,H,K,M,N,Q,T,V,Y); 18(A,C,H,K, M,N,Q,S,W); 19(A,C,G,I,L,T,V,W); 20(A,G,I,P,Q,S,T); 23(G,C,D,E,F,H,I,K,L,M,N,P,Q,R,S,T,V,W); 24(K,A,D,E,F, H,I,L,M,N,P,R,T,V,W,Y); 25(N,A,C,D,E,G,H,I,K,L,S,T,V, W); 26(N,C,G,K,L,M,Q,S,T,V,W,Y); 27(D,A,E,F,G,H,I,N, Q,R,S,T,V,Y); 28(A,D,E,F,G,H,I,L,M,N,P,Q,R,S); 29(P,C,E, G,H,I,K,L,M,Q,R,S,T,V,W,Y); 30(A,D,H,L,N,R,V,W); 31(G,D,E,H,M,P,Q,S,V); 32(T,A,I,M,Q,R,S); 33(N,D,E,F, K,L,M,Q,R,S); 37(T,A,C,D,E,F,G,H,I,K,L,M,P,Q,R,W,Y); 38(G,A,D,E,F,H,I,K,L,M,NT,V,W,Y); 39(N,C,E,H,I,L,P,Q, S,T,V,W,Y); 46(K,D,E,F,G,L,M,V,W); 47(A,D,E,F,H,M,T, W); 48(D,E,G,H,L,P,Q); 49(A,G,H,K,L,V,W); 50(T,A,D,F, K,L,R,S,W); 51(F,A,D,E,G,I,L,M,N,P,R,S,T,Y); 52(L,A,E, G,I,M,R,T,V,W); 53(Y,E,G,H,K,L,S,W); 54(S,E,F,G,H,K, M,P,R,T,VW,Y); 56(E,H,K,R,T,V); 58(S,D,G,H,I,K,M,Q,R, W); 60(V,G,K,L,Y); 64(T,C,D,E,G,I,K,L,N,R,V,Y); 66(F,A, G,H,I,L,M,N,Q,R,S,T,VW,Y); 68(A,C,G,I,S,T,V,W,Y); 69(L,A,D,G,H,I,K,N,S,T,W); 71(N,D,E,H,K,Q,R,S,T,V,W, Y); 72(T,A,D,E,F,H,I,K,L,N,P,R,S,V,Y); 73(N,E,G,H,K,R, S); 74(K,A,D,E,G,H,N,Q,S); 75(L,A,D,E,G,H,I,M,N,Q,R, S,T,V,Y); 85(S,F,H,I,N,Q,T); 86(I,L,M,P,Q,T,V,Y); 90(I,A, E,F,N,Q,T,V,Y); 91(G,E,F,H,I,M,Q,R); 93(L,D,H,I,K,N,P, Q,R,V,W); 94(N,D,G,K,M,P,R,S,T,V); 95(F,G,H,K,L,Q,T, V,W); 96(D,A,K,P,R,V); 97(L,A,D,I,M,Q,T); 98(K,D,E,H, I,M,Q); 99(E,D,K,P,Q,S,T,W); 101(N,C,D,E,H,M,Y); 105 (S,A,D,E,F,K,P,W); 108(R,E,F,K,M,Q,Y); 111(D,A,E,F,L, Q,T,V,W); 115(S,G,I,L,M,N,R,T,V); 120(V,G,H,I,N,S,W, Y); 122(D,A,E,F,H,I,N,S,T,Y); 123(T,E,G,I,K,L,M,N,Q, W); 125(R,C,G,I,N,Q,T,Y); 127(K,D,E,F,G,R,T); 128(V,C, H,I,L,N,S,W,Y); 130(D,A,C,E,F,G,H,Q,R,T,V,W,Y); 131 (A,C,H,I,K,N,Q,R,S,T,W,Y); 132(V,C,D,H,I,K,Q,R,W); 133(R,E,F,I,N,Q,V); 137(D,A,E,F,G,H,I,K,L,M,N,P,Q,R,S, T,V,W,Y); 140(V,C,E,F,I,L,M,N,Q,T); 151(L,I,M,N,P,T,V, W); 159(L,E,M,Q,R,W); 162(N,D,E,F,G,H,I,K,M,P,Q,R,S, Y); 163(G,A,F,L,M,N,P,R,S,W,Y); 164(Y,D,N,R,S,V); 179 (R,E,H,I,K,L,Q,V); 183(E,H,M,Q,S,T,V,Y); 187(V,G,H,L, N,Q,S,T,W); 188(Q,C,E,F,H,R,T); 189(T,D,E,G,K,M,N,Q, R,S,V); 190(G,D,H,R,S,Y); 216(S,D,G,N,Q,V,W); 223(K, A,H,L,M,Q,S,T,V); 232(R,C,D,I,L,M,P,T,W); 237(K,E,H,I, L,T,W,Y); 244(T,A,F,I,L,M,P,Q,S); 250(P,D,E,G,K,Q,R,S, T); 251(N,D,M,Q,S,T,W,Y); 252(I,A,C,D,E,F,G,H,K,L,N, Q,R,S,T,W); 254(D,A,H,K,N,P,T); 256(P,A,D,S,T); 263(G, C,H,I,K,M,V); 264(L,C,E,G,H,M,N,P,Q,R,S,T); 267(T,G,I, L,M,P,W); and 269(L,D,F,M,Q,V,W).

The productive positions in TLL that fall within the previously described Productivity Scores of "4" and the substitutions within those positions that are combinable are listed below. Position numbering based on mature TLL listed in SEQ ID NO. 3.

1(E,A,C,D,F,I,L,N,PQ,R,S,T,V,W,Y); 2(V,F,G,H,I,K,L, M,P,T); 3(S,A,D,E,G,H,K,Q,R,T,Y); 4(Q,A,D,F,G,I,K,L,M, N,P,R,S,W,Y); 5(D,H,I,K,L,S,T,V,W,Y); 6(L,A,E,H,I,K,M, Q,T,V,Y); 8(N,A,E,G,H,I,K,L,M,T,V,W,Y); 9(Q,A,D,E,G, H,I,K,N,R,W,Y); 13(F,A,H,K,M,N,Q,T,V,Y); 23(G,C,D,E, F,H,I,K,L,M,N,P,Q,R,S,T,V,W); 24(K,A,D,E,F,H,I,L,M,N, P,R,T,V,W,Y); 25(N,A,C,D,E,G,H,I,K,L,S,T,V,W); 26(N,C, G,K,L,M,Q,S,T,V,W,Y); 27(D,A,E,F,G,H,I,N,Q,R,S,T,V, Y); 28(A,D,E,F,G,H,I,L,M,N,P,Q,R,S); 29(P,C,E,G,H,I,K, L,M,Q,R,S,T,V,W,Y); 33(N,D,E,F,K,L,M,Q,R,S); 37(T,A, C,D,E,F,G,H,I,K,L,M,P,Q,R,W,Y); 38(G,A,D,E,F,H,I,K,L, M,NT,V,W,Y); 39(N,C,E,H,I,L,P,Q,S,T,V,W,Y); 46(K,D,E, F,G,L,M,V,W); 51(F,A,D,E,G,I,L,M,N,P,R,S,T,Y); 52(L,A, E,G,I,M,R,T,V,W); 54(S,E,F,G,H,K,M,P,R,T,VW,Y); 58(S, D,G,H,I,K,M,Q,R,W); 64(T,C,D,E,G,I,K,L,N,R,V,Y); 66(F, A,G,H,I,L,M,N,Q,R,S,T,VW,Y); 68(A,C,G,I,S,T,V,W,Y); 69(L,A,D,G,H,I,K,N,S,T,W); 71(N,D,E,H,K,Q,R,S,T,V,W, Y); 72(T,A,D,E,F,H,I,K,L,N,P,R,S,V,Y); 75(L,A,D,E,G,H,I, M,N,Q,R,S,T,V,Y); 90(I,A,E,F,N,Q,T,V,Y); 93(L,D,H,I,K, N,P,Q,R,V,W); 94(N,D,G,K,M,P,R,S,T,V); 111(D,A,E,F,L, Q,T,V,W); 120(V,G,H,I,N,S,W,Y); 122(D,A,E,F,H,I,N,S,T, Y); 123(T,E,G,I,K,L,M,N,Q,W); 130(D,A,C,E,F,G,H,Q,R, T,V,W,Y); 131(A,C,H,I,K,N,Q,R,S,T,W,Y); 137(D,A,E,F,G, H,I,K,L,M,N,P,Q,R,S,T,V,W,Y); 140(V,C,E,F,I,L,M,N,Q, T); 162(N,D,E,F,G,H,I,K,M,P,Q,R,S,Y); 163(G,A,F,L,M,N,

P,R,S,W,Y); 189(T,D,E,G,K,M,N,Q,R,S,V); 250(P,D,E,G,K,Q,R,S,T); 252(I,A,C,D,E,F,G,H,K,L,N,Q,R,S,T,W); and 264(L,C,E,G,H,M,N,P,Q,R,S,T).

In a subsequent study, additional substitutions of productive positions in TLL were tested and found to be combinable. The additional substitutions within those positions that are combinable are listed below. Position numbering based on mature TLL listed in SEQ ID NO. 3.

11(A,E,I), 23(A), 24(Q,S), 27(K,L), 29(N), 30(E,G,I,S,Y), 31(T), 33(C,I,P,T,V), 45(A,G,S,T), 48(N,R,T,V), 49(C,Y), 50(M), 51(H,V), 56(A,M,N,S), 58(A,F), 71(C,F,P), 73(Q,T), 74(I,M,T,W), 75(K), 91(K,N,Y), 94(A,H), 101(A), 108(A), 111(G,H,I,K,M,S,Y), 122(K,L,Q), 128(T,V), 130(K,M), 133(D,H,L,W), 135(A,D,M,N,Y), 140(Y), 159(G), 163(Q), 183(C), 187(C,I), 188(A,M,W), 190(W), 227(A,I,S), 233(F,I,V), 251(V), 252(M,V).

EXAMPLE 5

Combinable Mutations and Suitability Scores

As shown in Example 3, combinable mutations in TLL were determined using performance index (PI) values resulting from the assays described in Example 1: CS-61 micro-swatch assay, hydrolysis of p-Nitrophenyl esters, (activity), detergent stability, LAS stability, and thermostability assays, and protein determination (expression). Combinable mutations were assigned to groups A, B or C according to criteria set forth in Example 3. These substitutions are further assigned a Suitability Score based on the group(s) (A, B, C) where the substitution appears, and where higher suitability scores represents a substitution more suitable for use in making combinatorial variants. Suitability scores are defined in Table 5.1. Suitability scores for individual substitutions of TLL that fit the above criteria are reported in Table 5.2. Table 5.1 defines each Suitability Score as it relates to groups of combinable mutations and productive positions.

TABLE 5.1

Suitability Score

| Substitutions Occur in Group(s) | Suitability Score |
| --- | --- |
| A, B and C | +++++ |
| A and B | ++++ |
| A or (B and C) | +++ |
| B | ++ |
| C | + |

Table 5.2 identifies the Suitability Score of individual substitutions in TLL. Position numbering based on mature TLL listed in SEQ ID NO: 3.

TABLE 5.2

Suitability Score of individual substitutions in TLL

| POS | (+) | (++) | (+++) WT AA 1ST | (++++) | (+++++) |
| --- | --- | --- | --- | --- | --- |
| 1 | CL | | ERV | QT | ADFINPSWY |
| 2 | | K | VHT | FGMP | IL |
| 3 | R | AH | SEQ | KT | DGY |

TABLE 5.2-continued

Suitability Score of individual substitutions in TLL

| POS | (+) | (++) | (+++) WT AA 1ST | (++++) | (+++++) |
| --- | --- | --- | --- | --- | --- |
| 4 | | P | QY | AGIKLMNRS | DFW |
| 5 | | | D | KW | HILSTVY |
| 6 | AH | KY | LQV | EM | IT |
| 7 | MV | H | F | | Y |
| 8 | K | | N | AE | GHILMTVWY |
| 9 | Y | DW | QAI | EGNR | HK |
| 11 | | | N | HKY | V |
| 12 | | W | L | FHV | |
| 13 | KTV | AMY | F | Q | HN |
| 14 | V | | A | | S |
| 15 | GH | M | Q | S | |
| 16 | | H | Y | | W |
| 17 | | | S | | E |
| 18 | MNW | | ACHS | Q | K |
| 19 | ILVW | | AT | C | G |
| 20 | I | Q | AP | GS | T |
| 22 | LM | H | C | | |
| 23 | | R | GP | CFLMSW | DEHIKNQTV |
| 24 | MR | | KF | Y | ADEHILNPTVW |
| 25 | E | S | NADGVW | CHK | ILT |
| 26 | | | NLQ | C | GKMSTVWY |
| 27 | | | D | F | AEGHINQRSTVY |
| 28 | | | AFGL | HMPQR | DEINS |
| 29 | | GS | PCI | QWY | EHKLMRTV |
| 30 | | LN | AHRW | DV | |
| 31 | MPV | | G | EQ | DHS |
| 32 | | | TQ | AIMRS | |
| 33 | | M | NK | | DEFLQRS |
| 34 | | | I | | P |
| 35 | | | TER | K | |
| 37 | RY | H | TAFLM | C | DEGIKPQW |
| 38 | AE | | GT | VW | DFHIKLMNY |
| 39 | CW | Q | N | PTY | EHILSV |
| 40 | | F | A | W | MS |
| 41 | V | | C | | |

TABLE 5.2-continued

Suitability Score of individual substitutions in TLL

| POS | (+) | (++) | (+++) WT AA 1ST | (++++) | (+++++) |
|---|---|---|---|---|---|
| 42 | C | | P | V | GIW |
| 43 | | | EI | DM | RT |
| 44 | | | VHT | | I |
| 45 | | | E | Q | FV |
| 46 | | | KE | FGVW | DLM |
| 47 | | W | ADEFM | T | H |
| 48 | L | G | D | | EHPQ |
| 49 | GLW | | AHK | | V |
| 50 | | FK | TDW | A | LRS |
| 51 | | DPY | F | NRT | AEGILMS |
| 52 | | M | LT | ERW | AGIV |
| 53 | | | YLW | EGHKS | |
| 54 | EHM | FGKW | S | RY | PTV |
| 55 | | W | F | G | |
| 56 | | | E | V | HKRT |
| 57 | S | | D | | |
| 58 | DR | I | SGHKQW | | M |
| 59 | D | | G | | |
| 60 | KY | | L | V | G |
| 61 | ADR | | GL | | |
| 62 | N | | D | | |
| 63 | KQ | | V | | T |
| 64 | | KRY | TDIL | CENV | G |
| 65 | Y | | L | GV | |
| 66 | AST | GY | FILV | NQR | HMW |
| 67 | | H | L | Q | IV |
| 68 | | Y | ACW | | GISTV |
| 69 | | D | L | AGHNW | IKST |
| 70 | | | D | | S |
| 71 | | | NE | VWY | DHKQRST |
| 72 | | | TK | P | ADEFHILNRSVY |
| 73 | | | N | EGK | HRS |
| 74 | E | | KADG | NQ | HS |
| 75 | | M | L | DNRY | AEGHIQSTV |
| 76 | S | | IV | H | |
| 77 | | | VA | ILNT | |
| 79 | M | | S | | A |
| 84 | QW | H | R | | |
| 85 | FI | | SHNQ | | T |
| 86 | | Q | IVY | LM | PT |
| 87 | A | | ED | PV | G |
| 90 | | Y | IV | QT | AEFN |
| 91 | | | G | F | EHIMQR |
| 92 | | A | N | | T |
| 93 | HNW | IPV | LDKQR | | |
| 94 | KMP | S | NGTV | D | R |
| 95 | | HT | FKL | | GQVW |
| 96 | PR | V | D | | AK |
| 97 | I | | LAM | Q | DT |
| 98 | | M | KH | DEI | Q |
| 99 | PQ | | E | K | DSTW |
| 100 | | M | I | | |
| 101 | CEM | | N | | DHY |
| 102 | H | | D | | |
| 103 | Y | | I | | |
| 105 | F | | SW | ADEP | K |
| 106 | H | | G | | |
| 108 | | | RF | EM | KQY |
| 109 | T | | G | | |
| 110 | N | | HS | | |
| 111 | FW | | D | | AELQTV |
| 112 | FQ | | G | | |
| 114 | | | T | | FIMV |
| 115 | IL | N | SGMRV | | T |
| 117 | K | Q | WHV | | |
| 118 | | | R | | P |
| 119 | QV | | SDI | | T |
| 120 | I | | VGHNSW | | Y |
| 121 | Q | | A | | K |
| 122 | | STY | DAF | EN | HI |
| 123 | IK | | T | ELQ | GMNW |

TABLE 5.2-continued

Suitability Score of individual substitutions in TLL

| POS | VARIANTS SUITABILITY SCORE (+) | (++) | (+++) WT AA 1ST | (++++) | (+++++) |
|---|---|---|---|---|---|
| 125 | C | I | RY | NT | GQ |
| 126 | | M | Q | I | |
| 127 | | D | K | EFR | GT |
| 128 | LNW | Y | VCI | HS | |
| 130 | E | CR | DVWY | FQ | AGHT |
| 131 | CN | | AKST | RWY | HIQ |
| 132 | C | I | VQ | DKW | HR |
| 133 | FNV | | RI | EQ | |
| 134 | | P | E | | LV |
| 135 | | | H | FT | K |
| 136 | R | | P | DQ | |
| 137 | AFLMNP | | DIRW | SV | EGHKQTY |
| 138 | F | | Y | | |
| 139 | | | R | L | T |
| 140 | EILN | C | V | FMQT | |
| 142 | | | FHY | | |
| 143 | N | | T | AGS | |
| 149 | | | G | A | |
| 151 | | P | LMW | N | ITV |
| 152 | I | V | A | | |
| 153 | | | TS | | |
| 154 | MY | | V | F | IL |
| 155 | T | | A | | GS |
| 156 | | T | GM | FW | |
| 158 | | | D | Y | EF |
| 159 | MW | | LQR | E | |
| 162 | MPY | | NDEFHIKQS | | GR |
| 163 | AMR | | GFL | SW | NPY |
| 164 | | DR | Y | NS | V |
| 165 | P | Y | D | I | |
| 166 | | | I | DW | G |
| 167 | | | D | N | |
| 168 | Q | | VG | L | |
| 169 | Y | | FS | | |
| 170 | G | | S | | |
| 176 | FNW | | V | | IL |

TABLE 5.2-continued

Suitability Score of individual substitutions in TLL

| POS | VARIANTS SUITABILITY SCORE (+) | (++) | (+++) WT AA 1ST | (++++) | (+++++) |
|---|---|---|---|---|---|
| 179 | | | RHK | EI | LQV |
| 180 | DQ | | AT | | K |
| 181 | | | F | | L |
| 183 | HMQSTY | | E | V | |
| 184 | W | | FY | | |
| 187 | | | V | | GHLNQSTW |
| 188 | ER | F | Q | H | CT |
| 189 | EM | | T | KV | DGNQRS |
| 190 | DHRSY | | G | | |
| 191 | | | G | | FLV |
| 192 | NP | | T | | |
| 193 | | | LT | | |
| 196 | | | I | | V |
| 198 | | | HGS | | |
| 199 | NV | | T | | G |
| 200 | P | | NS | A | |
| 202 | M | | IL | | PV |
| 205 | | | R | D | |
| 206 | N | | L | | |
| 208 | | N | P | | E |
| 209 | | | RH | ST | |
| 210 | S | | E | | |
| 211 | | | FRT | | IW |
| 212 | Q | | G | | |
| 213 | | S | Y | | |
| 214 | M | | SA | D | |
| 216 | | D | SV | GQ | NW |
| 217 | | | SV | H | K |
| 218 | | | P | T | |
| 221 | FGY | | W | | |
| 223 | HL | | KA | M | QSTV |
| 224 | AFP | | S | | |
| 225 | C | | G | | EKR |
| 226 | D | | T | N | |
| 227 | | C | LH | | M |
| 228 | A | | V | E | R |

TABLE 5.2-continued

Suitability Score of individual substitutions in TLL

| POS | (+) | (++) | (+++) WT AA 1ST | (++++) | (+++++) |
|---|---|---|---|---|---|
| 229 | MS | I | P | K | |
| 230 | | | VW | | |
| 231 | G | | TH | KLM | |
| 232 | DW | CL | RP | | IMT |
| 233 | | | N | | DGHQ |
| 236 | W | | V | | |
| 237 | | E | KHTW | | ILY |
| 238 | V | | I | | |
| 239 | K | | E | | |
| 242 | | | D | | T |
| 243 | S | | A | | |
| 244 | AFLMP | | TQS | | I |
| 246 | I | | G | | |
| 248 | DLY | | N | | |
| 249 | GT | E | Q | | |
| 250 | DGKT | E | PS | | QR |
| 251 | MQSTY | | N | | DW |
| 252 | W | F | ICE | KLN | ADGHQRST |
| 253 | FHN | | PR | | |
| 254 | NP | AK | DT | H | |
| 255 | W | | I | F | L |
| 256 | D | | P | T | AS |
| 257 | | W | A | | Y |
| 259 | WY | | L | | |
| 260 | P | | W | | |
| 262 | K | | F | | D |
| 263 | CHM | | GK | IV | |
| 264 | | | LCG | HST | EMNPQR |
| 265 | LRW | | I | | MQ |
| 266 | E | | G | | |
| 267 | | I | TGM | P | LW |
| 268 | DN | | CH | | |
| 269 | | | L | F | DMQVW |

EXAMPLE 6

Surface Modifications

Positions and substitutions contributing to favorable surface modifications, such as altered charge or hydrophobicity of TLL are set forth in Table 5.1. Productive positions containing all combinable substitutions were determined using the criteria for productive positions as described in Example 3. The data were further analyzed to determine substitutions which change hydrophobicity or charge, and maintain all important properties. Hydrophobicity of each substitution was determined using the methods of White and Wimley (White, S. H. and Wimley, W. C., Annu. Rev. Biophys. Biomol. Strut. 28:319-65, (1999)). A subgroup of combinable positions and substitutions demonstrating favorable surface modifications in TLL is shown in Table 6.1.

Table 6.1 sets forth substitutions which demonstrate favorable surface modifications. Position numbering based on mature TLL listed in SEQ ID NO: 3

TABLE 6.1

Combinable positions and substitutions with favorable surface modifications.

| VARIANT | TYPE |
|---|---|
| A018K | HYDRO, CHARGE |
| D027N | HYDRO, CHARGE |
| D027S | HYDRO, CHARGE |
| D027T | HYDRO, CHARGE |
| D027V | HYDRO, CHARGE |
| P029E | HYDRO, CHARGE |
| N033D | HYDRO, CHARGE |
| N033E | HYDRO, CHARGE |
| N033R | HYDRO, CHARGE |
| F051T | HYDRO |
| S058M | HYDRO |
| T072R | HYDRO, CHARGE |
| L075Q | HYDRO |
| N101D | HYDRO, CHARGE |
| R108K | HYDRO |
| R108Q | HYDRO, CHARGE |
| R108Y | HYDRO, CHARGE |
| T114F | HYDRO |
| T114I | HYDRO |
| A121K | HYDRO, CHARGE |
| H135F | HYDRO |
| D137V | HYDRO, CHARGE |
| G156W | HYDRO |
| G163Y | HYDRO |
| V187N | HYDRO |
| V187W | HYDRO |
| P250E | HYDRO, CHARGE |
| I252A | HYDRO |
| I252T | HYDRO |
| L264P | HYDRO |

EXAMPLE 7

Combinable Mutations Based on Detergent Performance

Additional combinable mutations in TLL were identified using performance index (PI) values resulting from the CS-61 micro-swatch assay (performed with either half dose, half dose+adjuvant, or full dose), detergent stability, and protein determination (expression). Table 7.1 identifies combinable positions and substitutions demonstrating performance indices (PI) relative to TLL parent for expression≥0.8, detergent stability≥0.8 and detergent performance≥1.1 at half dose, half-dose+adjuvant, or full dose. Position numbering based on mature TLL listed in SEQ ID NO: 3.

| Performance Index (PI) [Detergent Performance] | | | | |
|---|---|---|---|---|
| | | | Cleaning performance | |
| Group | Expression | Detergent stability | Half dose | Half dose + adjuvant | Full dose |
| I | ≥0.8 | ≥0.8 | ≥1.1 | | |
| II | ≥0.8 | ≥0.8 | | ≥1.1 | |
| III | ≥0.8 | ≥0.8 | | | ≥1.1 |

TABLE 7.1

| Detergent performance | | | | | |
|---|---|---|---|---|---|
| Group I | | Group II | | Group III | |
| POS | Substitution | POS | Substitution | POS | Substitution |
| 1 | S | 1 | S | 1 | S |
| 5 | H, I, S, T | 3 | T | 5 | H, I, T |
| 8 | H | 4 | F | 23 | E, Q |
| 9 | K, N | 5 | H, I, S, T | 29 | H, I, R, T |
| 11 | H, K | 8 | H, T, V | 39 | H, I |
| 13 | N | 9 | G, H, K | 43 | R, T |
| 19 | G | 11 | K | 54 | T |
| 23 | K, N, Q R | 12 | V, W | 58 | Q |
| 27 | Q, R | 18 | K | 115 | T |
| 29 | K, R | 19 | G | 130 | A, R |
| 32 | A | 23 | K, Q, R | 154 | L |
| 33 | D | 27 | R, S | 158 | E |
| 37 | G, H, Q | 32 | I | 180 | K |
| 38 | F, L, M, W, Y | 38 | F, L, M, W, Y | 187 | T |
| 39 | I, L | 39 | I, P | 228 | R |
| 42 | W | 43 | I, R, T | 269 | W |
| 43 | D, I, R, T | 45 | F, Q | | |
| 45 | F, Q, V | 53 | K | | |
| 51 | M | 54 | P | | |
| 53 | E | 56 | K, R | | |
| 54 | P | 58 | H, Q | | |
| 56 | H, K, R | 75 | G, Q, R | | |
| 58 | H, K, Q, W | 77 | I | | |
| 69 | R | 90 | T | | |
| 73 | R | 91 | I, Q | | |
| 75 | A, R | 105 | P | | |
| 75 | T | 123 | N | | |
| 77 | I, L, T | 127 | F | | |
| 90 | F, T | 130 | A, F, H, Q, R | | |
| 91 | I, Q | 131 | R | | |
| 94 | R | 136 | Q | | |
| 105 | P | 137 | R, S | | |
| 108 | K | 143 | S | | |
| 122 | F | 156 | T | | |
| 125 | T | 162 | G | | |
| 130 | A, R | 163 | S | | |
| 132 | K, R | 164 | R, V | | |
| 134 | L | 166 | G | | |
| 137 | R | 180 | K | | |
| 151 | T | 187 | G, H, N, Q, S, T, W | | |
| 155 | S | 188 | F | | |
| 156 | W | 189 | D, G | | |
| 163 | F, P | 199 | G | | |
| 164 | R | 228 | R | | |
| 180 | K | 252 | N | | |
| 183 | V | 264 | R | | |
| 184 | Y | 265 | Q | | |
| 187 | G, H, N, Q, S, T, W | | | | |
| 189 | G, Q | | | | |
| 211 | I | | | | |
| 214 | A | | | | |
| 228 | R | | | | |
| 232 | P | | | | |

TABLE 7.1-continued

| Detergent performance | | | | | |
|---|---|---|---|---|---|
| Group I | | Group II | | Group III | |
| POS | Substitution | POS | Substitution | POS | Substitution |
| 233 | Q | | | | |
| 244 | I | | | | |
| 252 | N | | | | |
| 265 | Q | | | | |

EXAMPLE 8

Combinable Mutations Based on Stability

Additional combinable mutations in TLL were identified using performance index (PI) values resulting from thermostability, detergent stability or LAS stability assays, hydrolysis of pNPO substrate at pH 8, and protein determination (expression). Table 8.1 identifies combinable positions and substitutions demonstrating performance indices (PI) relative to TLL parent for expression≥0.8, hydrolysis of pNPO substrate at pH 8≥0.8, and either theromostability, detergent or LAS stability≥1.1. Position numbering based on mature TLL listed in SEQ ID NO: 3.

| Performance Index (PI) [Stability] | | | | | |
|---|---|---|---|---|---|
| | | pNPO | Stability | | |
| Group | Expression | hydrolysis (pH 8) | Thermo-stability | Detergent Stability | LAS stability |
| IV | ≥0.8 | ≥0.8 | ≥1.1 | | |
| V | ≥0.8 | ≥0.8 | | ≥1.1 | |
| VI | ≥0.8 | ≥0.8 | | | ≥1.1 |

TABLE 8.1

| Stability | | | | | |
|---|---|---|---|---|---|
| Group IV | | Group V | | Group VI | |
| POS | Substitution | POS | Substitution | POS | Substitution |
| 2 | I | 12 | F | 1 | F, R |
| 11 | K | 13 | Q | 4 | K, L, N, W |
| 15 | S | 15 | S | 5 | K |
| 18 | K | 19 | C, G | 11 | K |
| 23 | C, D, E, F, H, I, K, M, N, Q, S, T, V | 20 | P | 23 | K |
| 24 | H | 23 | D, E, F, I, V | 27 | A, H, N, R, S, T, V |
| 26 | T | 24 | W | 37 | P |
| 27 | A, G, H, N, Q, R, S, T, V | 26 | C, T, W, Y | 38 | H, K, L, W, Y |
| 29 | E | 28 | D, P | 42 | V |
| 37 | P | 31 | E | 43 | I, R |
| 48 | E, Q | 34 | P | 45 | F, Q, V |
| 50 | S | 37 | C, D | 47 | T |
| 51 | A, I, L, S, T | 39 | E, L, P | 49 | V |
| 56 | K, V, | 42 | I, V | 51 | I, M, S |
| 58 | M | 45 | F, V | 56 | H, K, S, T |
| 66 | N, Q | 46 | F, G, L, W | 58 | M, Q |
| 75 | A, G, Q, R | 47 | F, M, T, W | 73 | S |
| 77 | I, T | 49 | H, V | 75 | D, E, G, Q, R |
| 91 | E, Q | 51 | A, G, I, L, M, S, T | 91 | Q |
| 94 | R | 60 | L | 94 | R |
| 96 | K | 64 | V | 101 | D |

TABLE 8.1-continued

| Stability | | | | | |
|---|---|---|---|---|---|
| Group IV | | Group V | | Group VI | |
| POS | Substitution | POS | Substitution | POS | Substitution |
| 99 | D, S | 66 | Q | 108 | K |
| 101 | D, H | 68 | S, T, V | 111 | A |
| 108 | K, M, Y | 73 | E, G, R, S | 119 | D, T |
| 111 | A, E, Q | 75 | E, G, Q, R | 120 | Y |
| 114 | F, I, V | 77 | A, L, N, T | 154 | I |
| 117 | Q | 91 | E, Q | 179 | L |
| 120 | N | 94 | D | 187 | T |
| 121 | K | 108 | E, F, M, Q, Y | 189 | D, Q |
| 135 | F | 114 | F, I, V | 200 | A |
| 137 | I, Q, R | 127 | T | 209 | S |
| 154 | F, I, L | 128 | H, S, Y | 211 | W |
| 155 | G, S | 131 | R, W, Y | 226 | N |
| 156 | W | 132 | D | 250 | E, Q |
| 163 | F | 133 | E, Q | 251 | W |
| 169 | S | 136 | D, Q | 252 | A |
| 176 | I | 139 | M | 256 | T |
| 187 | H, N, W | 140 | F, M, Q | | |
| 226 | N | 142 | Y | | |
| 250 | E | 154 | I | | |
| 252 | A | 155 | S | | |
| 256 | T | 156 | W | | |
| 264 | C, H, M, P, Q, S | 159 | E, R | | |
| 265 | M | 163 | F, L, P, Y | | |
| 269 | Q | 168 | G, L | | |
| | | 179 | L | | |
| | | 187 | H, N, Q, T | | |
| | | 188 | F | | |
| | | 189 | D | | |
| | | 205 | D | | |
| | | 208 | E | | |
| | | 209 | S | | |
| | | 214 | D | | |
| | | 223 | T | | |
| | | 225 | E | | |
| | | 228 | E | | |
| | | 237 | L, Y | | |
| | | 250 | E | | |
| | | 251 | D | | |
| | | 252 | A | | |
| | | 256 | T | | |
| 264 | C, H, P, Q, S | | | | |
| 265 | M | | | | |

EXAMPLE 9

Combinable Mutations Based on Ester Hydrolysis

Additional combinable mutations in TLL were identified using performance index (PI) values resulting from hydrolysis of pNPB, pNPO and pNPP substrates at pH 8, thermostability, and protein determination (expression). Table 9.1 identifies combinable positions and substitutions demonstrating performance indices (PI) relative to TLL parent for expression≥0.8, thermostability≥0.8, and pNPB hydrolysis≥1.1, or pNPO hydrolysis≥1.1, or pNPP hydrolysis≥1.1, or pNPB and pNPO hydrolysis≥1.1, or pNPO and pNPP hydrolysis≥1.1 or pNPB, pNPO, and pNPP hydrolysis≥1.1. Position numbering based on mature TLL listed in SEQ ID NO: 3.

| Performance Index (PI) [Hydrolysis] | | | | | |
|---|---|---|---|---|---|
| | | | Ester hydrolysis | | |
| Group | Expression | Thermostability | pNPB | pNPO | pNPP |
| VII | ≥0.8 | ≥0.8 | ≥1.1 | | |
| VIII | ≥0.8 | ≥0.8 | | ≥1.1 | |
| IX | ≥0.8 | ≥0.8 | | | ≥1.1 |
| X | ≥0.8 | ≥0.8 | ≥1.1 | ≥1.1 | |
| XI | ≥0.8 | ≥0.8 | | ≥1.1 | ≥1.1 |
| XII | ≥0.8 | ≥0.8 | ≥1.1 | ≥1.1 | ≥1.1 |

TABLE 9.1

| Ester Hydrolysis | | | | | | | | | | | |
|---|---|---|---|---|---|---|---|---|---|---|---|
| Group VII | | Group VIII | | Group IX | | Group X | | Group XI | | Group XII | |
| POS | SUB | POS | SUB | POS | SUB | POS | SUB | POS | SUB | POS | SUB |
| 2 | I, L | 1 | D | 1 | Q, S | 2 | L | 3 | D, T | 3 | D |
| 3 | D | 2 | L | 3 | D, T | 3 | D | 4 | A, D, L, M | 4 | D, L |
| 4 | D, I, L, W | 3 | D, T | 4 | A, D, L, M | 4 | D, L | 5 | H, Y | 5 | H |
| 5 | H, Y | 4 | A, D, L, M | 5 | H, S, Y | 5 | H, Y | 23 | F | 5 | Y |
| 8 | H, M | 5 | H, Y | 9 | M | 8 | M | 27 | E, N, Q, T | 27 | Q, T |
| 9 | K | 8 | A, E, M | 11 | K | 18 | K | 29 | R | 29 | R |
| 11 | H, K | 9 | R | 12 | F | 24 | A, T | 33 | D, Q | 40 | M |
| 18 | K | 18 | K | 15 | S | 26 | K | 40 | M | 108 | K |
| 23 | K | 23 | D, E, F, N, Q | 23 | F | 27 | A, I, Q, T | 48 | Q | 111 | L |
| 24 | A, T | 24 | A, D, E, H, N, T | 27 | E, N, Q, T | 29 | R | 51 | I, L, T | 134 | L |
| 26 | K, T | 26 | G, K | 29 | R | 40 | M | 56 | H, K, R, T | 137 | H, K, S, Y |
| 27 | A, I, Q, T | 27 | A, E, I, N, Q, T | 32 | A, Q, S | 75 | M | 58 | M, Q | 162 | G |
| 29 | H, I, K, R, T, V | 29 | E, Q, R | 33 | D, Q | 108 | K, Y | 75 | R | 163 | Y |
| 30 | R, V | 33 | D, E, F, M, Q, R, S | 35 | E, K, R | 111 | L, T | 77 | LT | 187 | H, S, W |
| 32 | S | 37 | D, E, P, Q | 40 | M | 122 | Y | 87 | P | 232 | P |
| 35 | K | 38 | D, N | 48 | Q | 123 | Q | 108 | K | | |

TABLE 9.1-continued

| Ester Hydrolysis | | | | | | | | | | | |
|---|---|---|---|---|---|---|---|---|---|---|---|
| Group VII | | Group VIII | | Group IX | | Group X | | Group XI | | Group XII | |
| POS | SUB | POS | SUB | POS | SUB | POS | SUB | POS | SUB | POS | SUB |
| 37 | G | 40 | M | 51 | I, L, M, T | 125 | Q | 111 | A, L | | |
| 40 | M | 48 | E, Q | 56 | H, K, R, T | 130 | F, H | 114 | M | | |
| 54 | V | 49 | V | 58 | M, Q | 134 | L | 115 | R | | |
| 69 | A, K | 50 | E, F | 71 | E | 137 | H, K, S, T, W, Y | 127 | E, F | | |
| 71 | R | 51 | I, L, T | 75 | R | 155 | G | 130 | A | | |
| 72 | L | 54 | F, R | 77 | I, T | 156 | W | 132 | Q, R | | |
| 74 | A | 56 | H, K, R, T | 87 | P | 162 | G | 134 | L | | |
| 75 | M, S | 58 | M, Q | 105 | A | 163 | Y | 137 | E, G, H, I, K, Q, R, S, Y | | |
| 91 | I | 64 | N | 108 | K | 176 | I | 155 | S | | |
| 94 | R | 66 | Q | 111 | A, L | 180 | K | 162 | G | | |
| 101 | Y | 74 | Q | 114 | M | 187 | H, S, T, W | 163 | F, P, S, W, Y | | |
| 108 | K, Y | 75 | E, M, N, Q, R | 115 | R | 232 | P | 187 | H, N, Q, S, W | | |
| 111 | L, T, V | 77 | A, I, L, T | 127 | E, F | 233 | D | 189 | R | | |
| 114 | I | 87 | P | 130 | A | 265 | M | 225 | E | | |
| 122 | T, Y | 90 | E, F, Q | 132 | Q, R, W | 269 | M | 227 | M | | |
| 123 | Q | 101 | D | 134 | L | | | 232 | P | | |
| 125 | Q | 105 | D, P | 137 | E, G, H, I, K, Q, R, S, Y | | | 233 | Q | | |
| 130 | F, H | 108 | K, Q, Y | 143 | A | | | 264 | R, T | | |
| 132 | H, W | 111 | A, E, L, Q, T | 155 | S | | | | | | |
| 134 | L, V | 114 | F, M | 162 | G | | | | | | |
| 137 | H, K, S, T, W, Y | 115 | R | 163 | F, P, S, W, Y | | | | | | |
| 151 | T, W | 117 | Q | 164 | D, R | | | | | | |
| 155 | G | 120 | N | 165 | I, Y | | | | | | |
| 156 | W | 122 | Y | 187 | H, N, Q, S, W | | | | | | |
| 162 | G | 123 | E, L, M, N, Q | 189 | R | | | | | | |
| 163 | Y | 125 | Q | 225 | E | | | | | | |
| 166 | G | 127 | E, F, R | 227 | A, M | | | | | | |
| 176 | I | 130 | A, F, H, Q | 232 | P | | | | | | |
| 180 | K | 132 | K, Q, R | 233 | Q | | | | | | |
| 187 | H, S, T, W | 134 | L | 244 | I | | | | | | |
| 189 | K | 137 | E, G, H, I, K, Q, R, S, T, V, W, Y | 252 | A, K, L, R | | | | | | |
| 232 | L, P | 154 | F, L | 263 | LV | | | | | | |
| 233 | D, H | 155 | G, S | 264 | H, R, T | | | | | | |
| 237 | L, Y | 156 | F, W | 269 | V | | | | | | |
| 244 | I | 158 | E, F, Y | | | | | | | | |
| 252 | L, T | 162 | G, R | | | | | | | | |
| 255 | L | 163 | F, P, S, W, Y | | | | | | | | |
| 263 | LV | 169 | S | | | | | | | | |
| 265 | M | 176 | I | | | | | | | | |
| 269 | M | 180 | K | | | | | | | | |
| | | 187 | H, N, Q, S, T, W | | | | | | | | |
| | | 189 | D, Q, R | | | | | | | | |
| | | 225 | E | | | | | | | | |
| | | 227 | M | | | | | | | | |
| | | 228 | E | | | | | | | | |
| | | 232 | P | | | | | | | | |
| | | 233 | D, G, Q | | | | | | | | |
| | | 264 | E, M, N, P, Q, R, S, T | | | | | | | | |
| | | 265 | M | | | | | | | | |
| | | 269 | M, Q | | | | | | | | |

EXAMPLE 10

Combinable Mutations Based on Altering Ratio of Hydrolysis of C4:C16 Substrates Additional combinable mutations in TLL were identified using performance index (PI) values resulting from hydrolysis of pNPB and pNPP substrates at pH 8, thermostability, and protein determination (expression). Table 10.1 identifies combinable positions and substitutions demonstrating performance indices (PI) relative to TLL parent for expression≥0.8, thermostability≥0.8, and pNPB hydrolysis≤0.8 and pNPP hydrolysis≥1. Position numbering based on mature TLL listed in SEQ ID NO: 3.

| | Performance Index (PI) | | | |
|---|---|---|---|---|
| | | | Ester hydrolysis | |
| Group | Expression | Thermostability | pNPB | pNPP |
| XIII | ≥0.8 | ≥0.8 | ≤.8 | ≥1 |

TABLE 10.1

Combinable Mutations based on altering ratio of hydrolysis of C4:C16 substrates
Group XIII

| Pos | Substitution |
|---|---|
| 1 | Q |
| 9 | M |
| 12 | F |
| 15 | S |
| 23 | F |
| 27 | E |
| 32 | Q |
| 35 | E |
| 48 | Q |
| 58 | M, Q |
| 71 | E |
| 75 | R |
| 115 | R |
| 130 | A |
| 132 | Q, R |
| 137 | E, I, Q, R |
| 143 | A |
| 155 | S |
| 163 | F, P, S |
| 164 | D |
| 165 | I, Y |
| 187 | Q |
| 225 | E |
| 227 | A, M |
| 233 | Q |
| 252 | A, K, R |
| 264 | H, R, T |
| 269 | V |

EXAMPLE 11

Combinable Mutations Based on Hydrolysis at Low pH

Additional combinable mutations in TLL were identified using performance index (PI) values resulting from hydrolysis of pNPO at pH 6, thermostability, and protein determination (expression). Table 11.1 identifies combinable positions and substitutions demonstrating performance indices (PI) relative to TLL parent for expression≥0.8, thermostability≥0.8, and pNPO hydrolysis at pH 6≥1.1. Position numbering based on mature TLL listed in SEQ ID NO: 3.

| | Performance Index (PI) [Low pH hydrolysis] | | |
|---|---|---|---|
| Group | Expression | Thermostability | pNPO at pH 6 |
| XIV | ≥0.8 | ≥0.8 | ≥1.1 |

TABLE 11.1

Hydrolysis at low pH
Group XIV

| POS | Substitution |
|---|---|
| 1 | Q, S |
| 2 | L |
| 3 | T |
| 4 | A, D, L, M |
| 5 | H, Y |
| 9 | K |
| 11 | K |
| 12 | F |
| 15 | S |
| 24 | A, D, E, H, N |
| 27 | A, E, Q, T |
| 29 | R |
| 32 | A |
| 33 | D, F, Q |
| 38 | D |
| 40 | M |
| 48 | Q |
| 49 | V |
| 51 | I, L, M, T |
| 56 | H, K, T |
| 58 | M, Q |
| 69 | A |
| 75 | R |
| 77 | T |
| 91 | Q |
| 94 | R |
| 98 | I |
| 105 | A |
| 108 | K, Y |
| 111 | A, L |
| 114 | I, M, V |
| 121 | K |
| 123 | E, L, M, N, Q |
| 125 | Q |
| 127 | E, F |
| 130 | A, H |
| 132 | R |
| 134 | L |
| 137 | E, G, H, I, K, Q, R, S, V, Y |
| 143 | A |
| 151 | P |
| 154 | F, I, L |
| 155 | S |
| 156 | W |
| 158 | Y |
| 162 | G |
| 163 | F, P, W, Y |
| 164 | D, R |
| 165 | I, Y |
| 180 | K |
| 187 | H, N, Q, S, T, W |
| 189 | R |
| 227 | M |
| 228 | R |
| 232 | P |
| 252 | L |
| 263 | I, V |
| 265 | M |
| 269 | M |

EXAMPLE 12

Test for Lipase Activity in Different Levels of Adjuvant

The esterase activity of TLL parent enzyme was determined in the presence of different levels of four adjuvant compounds (Table 12.1). Each adjuvant was mixed at concentrations corresponding to their critical micelle concentration (CMC), half the CMC, or one-quarter the CMC in 0.05M HEPES buffer, pH 8.2, and with 6 gpg water hardness added. The rate of hydrolysis for pNP octanoate was measured as described above in Example 1B. For all four adjuvant compounds, the esterase activity of TLL parent enzyme is significantly higher at the one-quarter CMC level compared to the full or one-half CMC level (FIG. 1).

TABLE 12.1

| Type | Examples | CMC (mM) |
|---|---|---|
| Non-ionic | n-Dodecyl-β-D-maltopyranoside (D310) | 0.17 |
| Zwitterionic | LysoFos Choline 14 (L214) | 0.036 |
| | Anzergent 3-12 (AZ312) | 2.8 |
| | CHAPSO (C317) | 8 |

---

We claim:

1. A cleaning composition comprising at least one surfactant and a lipolytic enzyme variant, wherein said lipolytic enzyme variant comprises an amino acid modification to a parent lipolytic enzyme, wherein the modification is at a productive position of the lipolytic enzyme variant, wherein at least one modification of the modifications tested at the productive position meet at least one of the following criteria:

a) a position wherein the minimum performance indices (PI) relative to *Thermomyces lanuginosus* lipase (TLL) parent for expression, Cotton Soils 61 (CS-61) micro-swatch activity at pH 8.2, activity on p-Nitrophenyl ester substrates at pH 6 or pH 8.2, and detergent stability, Sodium linear $C_{11-13}$ alkyl benzene sulfonate (LAS) stability or thermostability are greater than or equal to 0.9, and in addition have a PI for any one of these tests that is greater than or equal to 1.0;

b) a position wherein the minimum PI relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.8, and in addition have a PI for any one of these tests that is greater than or equal to 1.2; or c) a position wherein the minimum PI relative to TLL parent for expression, CS-61 micro-swatch activity at pH 8.2, activity on p-Nitrophenyl ester substrates at pH 6 or pH 8.2, and detergent stability, LAS stability or thermostability are greater than or equal to 0.5, and in addition have a PI for any one of these tests that is greater than or equal to 1.5;

wherein the productive position is selected from the group consisting of 23, 130, 154, and 187, wherein the variant has at least 93% amino acid sequence identity to SEQ ID NO:4, with the proviso that the modification at productive position 187 is not an I, with the proviso that the modification at position 23 is not a C, and wherein the amino acid positions of the lipolytic enzyme variant are numbered by correspondence with the amino acid sequence of TLL set forth in SEQ ID NO:4.

2. The cleaning composition of claim 1, wherein said at least one surfactant comprises a combination of an anionic surfactant and nonionic surfactant with 70-100% by surfactant weight of anionic surfactant and 0-30% by surfactant weight of nonionic surfactant.

3. The cleaning composition of claim 1, wherein said at least one surfactant comprises 70-100% by surfactant weight of anionic surfactant.

4. The cleaning composition of claim 1, wherein said at least one surfactant comprises 0-30% by surfactant weight of nonionic surfactant.

5. The cleaning composition of claims 2-4, wherein said anionic surfactant is selected from the group consisting of linear alkylbenzenesulfonate, alcohol ethoxysulfate, and soap.

6. The cleaning composition of claim 2 and claim 4, wherein said nonionic surfactant is selected from the group consisting of alcohol ethoxylate and alkylpolyglycoside.

7. The cleaning composition of claim 2, wherein said anionic surfactant comprises 16-27% by weight of the cleaning composition.

8. The cleaning composition of claim 2, wherein said nonionic surfactant comprises 1-7% by weight of the cleaning composition.

9. The cleaning composition of claims 1-8, wherein said cleaning composition is a laundry detergent composition, a dish detergent composition, or a hard surface cleaning composition.

10. The cleaning composition of claim 9, wherein said cleaning composition is a laundry detergent composition.

11. The cleaning composition of claim 1, wherein said lipolytic enzyme variant comprises an amino acid modification to a parent lipolytic enzyme, wherein the modification is at a productive position of the lipolytic enzyme variant, wherein the productive modification is selected from the group consisting of 23 (D, E, F, H, I, K, L, M, N, P, Q, R, S, T, V, W); 130 (A, C, E, F, G, H, Q, R, T, V, W, Y); 154 (F, I, L, M,Y); and 187 (G, H, L, N, O, S, T, W), wherein the amino acid positions of the lipolytic enzyme variant are numbered by correspondence with the amino acid sequence of TLL set forth in SEQ ID NO:4.

12. The cleaning composition of claim 1, wherein said lipolytic enzyme variant comprises an amino acid modification to a parent lipolytic enzyme, wherein the modification is at a productive position of the lipolytic enzyme variant, wherein the productive modification is selected from the group consisting of 23 (A); 130 (K, M); and 187 (C), wherein the amino acid positions of the lipolytic enzyme variant are numbered by correspondence with the amino acid sequence of TLL set forth in SEQ ID NO:4.

13. The cleaning composition of claim 1, wherein said lipolytic enzyme variant comprises an amino acid modification to a parent lipolytic enzyme, wherein the modification is at a productive position of the lipolytic enzyme variant wherein the lipolytic enzyme variant meets all of the criteria a), b), and c), wherein the modification is selected from the group consisting of 23 (D, E, H, I, K, N, Q, T, V); 130 (A, G, H, T); 154 (I, L); and 187 (G, H, L, N, O, S, T, W), wherein the amino acid positions of the lipolytic enzyme variant are numbered by correspondence with the amino acid sequence of TLL set forth in SEQ ID NO:4.

14. The cleaning composition of claim 1, wherein said lipolytic enzyme variant comprises an amino acid modification to a parent lipolytic enzyme, wherein the modification is at a productive position of the lipolytic enzyme variant, wherein the lipolytic enzyme variant meets the criteria a) and b) but not c) and wherein the modification is selected from the group consisting of 23 (F, L, M, S, W); 130 (F, Q); and 154 (F), wherein the amino acid positions of the lipolytic enzyme variant are numbered by correspondence with the amino acid sequence of TLL set forth in SEQ ID N0:4.

15. The cleaning composition of claim 1, further comprising at least one additional enzyme selected from the group consisting of hemicellulases, cellulases, peroxidases, lipolytic enzymes, metallolipolytic enzymes, xylanases, lipases, phospholipases, esterases, perhydrolases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidases, chondroitinases, laccases, and amylases.

16. A method of cleaning, comprising contacting a surface or an item with a cleaning composition of claim 1.

* * * * *

SEQUENCE LISTING

<160> NUMBER OF SEQ ID NOS: 8

<210> SEQ ID NO 1
<211> LENGTH: 834
<212> TYPE: DNA
<213> ORGANISM: Artificial Sequence
<220> FEATURE:
<223> OTHER INFORMATION: Nucleotide sequence of the synthetic TLL gene

<400> SEQUENCE: 1

```
gctagcgcag ctggcaaaga agttagccaa gatctgttca accaattcaa cctttcgct       60 caatactctg cagctgctta ctgcggaaag aacaacgatg cacctgctgg tactaacatc      120
acttgcacag gtaacgcatg tcctgaagta gaaaagctg atgctacatt tctttactct      180
tttgaagata gcggcgtcgg cgatgttacc ggtttcttag ctctggataa cacaaacaaa      240
cttatcgtcc ttagcttcag aggctctcgc tcaatcgaaa actggatcgg taaccttaat      300
tttgacttga agaaatcaa cgatatctgc tctggttgcc gtggccatga cggattcaca      360
tcatcttgga gaagcgtcgc agacacgctt cgccaaaaag tagaagatgc cgtacgcgaa      420
cacccagatt acagagtagt tttcacaggt cactctcttg gcggagcttt agcaacagta      480
gcaggcgctg atctccgcgg taacggatac gacattgatg tcttctctta cggcgctccg      540
cgcgtcggta acagagcgtt tgctgaattt ttaactgtac aaacaggcgg aactctttat      600
cgcatcactc acacaaacga tattgtcccg cgcttacctc cgagagaatt tggttactca      660
cacagctctc ctgaatactg gatcaaaagc ggtacattgg tacctgttac tcgaaacgat      720
atcgtcaaaa ttgaaggaat tgacgccacc ggcggcaaca accaaccgaa catccctgac      780
atcccggcac acctttggta cttcggctta atcggaacat gcctttaaaa gctt            834
```

<210> SEQ ID NO 2
<211> LENGTH: 301
<212> TYPE: PRT
<213> ORGANISM: Artificial Sequence
<220> FEATURE:
<223> OTHER INFORMATION: Synthetic amino acid sequence of TLL produced
      from expression plasmid pHYT-TLLwt

<400> SEQUENCE: 2

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Ser Ala Ala Gly Lys
            20                  25                  30

Glu Val Ser Gln Asp Leu Phe Asn Gln Phe Asn Leu Phe Ala Gln Tyr
        35                  40                  45

Ser Ala Ala Ala Tyr Cys Gly Lys Asn Asn Asp Ala Pro Ala Gly Thr
    50                  55                  60
```

Asn Ile Thr Cys Thr Gly Asn Ala Cys Pro Glu Val Glu Lys Ala Asp
 65                  70                  75                  80

Ala Thr Phe Leu Tyr Ser Phe Glu Asp Ser Gly Val Gly Asp Val Thr
                 85                  90                  95

Gly Phe Leu Ala Leu Asp Asn Thr Asn Lys Leu Ile Val Leu Ser Phe
            100                 105                 110

Arg Gly Ser Arg Ser Ile Glu Asn Trp Ile Gly Asn Leu Asn Phe Asp
        115                 120                 125

Leu Lys Glu Ile Asn Asp Ile Cys Ser Gly Cys Arg Gly His Asp Gly
130                 135                 140

Phe Thr Ser Ser Trp Arg Ser Val Ala Asp Thr Leu Arg Gln Lys Val
145                 150                 155                 160

Glu Asp Ala Val Arg Glu His Pro Asp Tyr Arg Val Val Phe Thr Gly
                165                 170                 175

His Ser Leu Gly Gly Ala Leu Ala Thr Val Ala Gly Ala Asp Leu Arg
            180                 185                 190

Gly Asn Gly Tyr Asp Ile Asp Val Phe Ser Tyr Gly Ala Pro Arg Val
        195                 200                 205

Gly Asn Arg Ala Phe Ala Glu Phe Leu Thr Val Gln Thr Gly Gly Thr
210                 215                 220

Leu Tyr Arg Ile Thr His Thr Asn Asp Ile Val Pro Arg Leu Pro Pro
225                 230                 235                 240

Arg Glu Phe Gly Tyr Ser His Ser Ser Pro Glu Tyr Trp Ile Lys Ser
                245                 250                 255

Gly Thr Leu Val Pro Val Thr Arg Asn Asp Ile Val Lys Ile Glu Gly
            260                 265                 270

Ile Asp Ala Thr Gly Gly Asn Asn Gln Pro Asn Ile Pro Asp Ile Pro
        275                 280                 285

Ala His Leu Trp Tyr Phe Gly Leu Ile Gly Thr Cys Leu
    290                 295                 300

<210> SEQ ID NO 3
<211> LENGTH: 272
<212> TYPE: PRT
<213> ORGANISM: Artificial Sequence
<220> FEATURE:
<223> OTHER INFORMATION: Synthetic amino acid sequence of the TLL mature
      protein produced from expression plasmid pHYT-TLLwt with a three
      amino acid amino-terminal extension

<400> SEQUENCE: 3

Ala Gly Lys Glu Val Ser Gln Asp Leu Phe Asn Gln Phe Asn Leu Phe
1               5                   10                  15

Ala Gln Tyr Ser Ala Ala Ala Tyr Cys Gly Lys Asn Asn Asp Ala Pro
            20                  25                  30

Ala Gly Thr Asn Ile Thr Cys Thr Gly Asn Ala Cys Pro Glu Val Glu
        35                  40                  45

Lys Ala Asp Ala Thr Phe Leu Tyr Ser Phe Glu Asp Ser Gly Val Gly
    50                  55                  60

Asp Val Thr Gly Phe Leu Ala Leu Asp Asn Thr Asn Lys Leu Ile Val
65                  70                  75                  80

Leu Ser Phe Arg Gly Ser Arg Ser Ile Glu Asn Trp Ile Gly Asn Leu
                85                  90                  95

Asn Phe Asp Leu Lys Glu Ile Asn Asp Ile Cys Ser Gly Cys Arg Gly
            100                 105                 110

His Asp Gly Phe Thr Ser Ser Trp Arg Ser Val Ala Asp Thr Leu Arg
            115                 120                 125

Gln Lys Val Glu Asp Ala Val Arg Glu His Pro Asp Tyr Arg Val Val
    130                 135                 140

Phe Thr Gly His Ser Leu Gly Gly Ala Leu Ala Thr Val Ala Gly Ala
145                 150                 155                 160

Asp Leu Arg Gly Asn Gly Tyr Asp Ile Asp Val Phe Ser Tyr Gly Ala
                165                 170                 175

Pro Arg Val Gly Asn Arg Ala Phe Ala Glu Phe Leu Thr Val Gln Thr
                180                 185                 190

Gly Gly Thr Leu Tyr Arg Ile Thr His Thr Asn Asp Ile Val Pro Arg
                195                 200                 205

Leu Pro Pro Arg Glu Phe Gly Tyr Ser His Ser Ser Pro Glu Tyr Trp
    210                 215                 220

Ile Lys Ser Gly Thr Leu Val Pro Val Thr Arg Asn Asp Ile Val Lys
225                 230                 235                 240

Ile Glu Gly Ile Asp Ala Thr Gly Gly Asn Asn Gln Pro Asn Ile Pro
                245                 250                 255

Asp Ile Pro Ala His Leu Trp Tyr Phe Gly Leu Ile Gly Thr Cys Leu
                260                 265                 270

<210> SEQ ID NO 4
<211> LENGTH: 269
<212> TYPE: PRT
<213> ORGANISM: Thermomyces lanuginosus
<220> FEATURE:
<221> NAME/KEY: misc_feature
<223> OTHER INFORMATION: amino acid sequence of the TLL mature protein
      based on the naturally occurring gene sequence

<400> SEQUENCE: 4

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
                20                  25                  30

Asn Ile Thr Cys Thr Gly Asn Ala Cys Pro Glu Val Glu Lys Ala Asp
            35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
                180                 185                 190

Leu Tyr Arg Ile Thr His Thr Asn Asp Ile Val Pro Arg Leu Pro Pro

```
                    195                 200                 205
Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 5
<211> LENGTH: 87
<212> TYPE: DNA
<213> ORGANISM: Artificial Sequence
<220> FEATURE:
<223> OTHER INFORMATION: Synthetic oligonucleotide

<400> SEQUENCE: 5
gttaccttga atgtatataa acattctcaa agggatttct aataaaaaac gctcggttgc      60
cgccgggcgt tttttatgca tcgatgg                                          87

<210> SEQ ID NO 6
<211> LENGTH: 86
<212> TYPE: DNA
<213> ORGANISM: Artificial Sequence
<220> FEATURE:
<223> OTHER INFORMATION: Synthetic oligonucleotide

<400> SEQUENCE: 6
aattccatcg atgcataaaa aacgcccggc ggcaaccgag cgttttttat tagaaatccc      60
tttgagaatg tttatataca ttcaag                                           86

<210> SEQ ID NO 7
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 7
gatcctgact gcctg                                                       15

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
agctcaggca gtcag                                                       15
```